US010577418B2

(12) United States Patent
Campbell et al.

(10) Patent No.: US 10,577,418 B2
(45) Date of Patent: *Mar. 3, 2020

(54) MONOCLONAL ANTI-GPC-1 ANTIBODIES AND USES THEREOF

(71) Applicant: GLYP HOLDINGS PTY LIMITED, Macquarie Park, NSW (AU)

(72) Inventors: Douglas Campbell, North Sydney (AU); Irene Justiniano Fuenmayor, St. Ives (AU); Aline Nocon, Leichardt (AU); Julie Soon, North Bondi (AU); Quach Truong, Leichardt (AU); Bradley Walsh, Turramurra (AU); Sandra Wissmueller, Currans Hill (AU)

(73) Assignee: Minomic International LTD., Macquarie Park, NSW (AU)

( * ) Notice: Subject to any disclaimer, the term of this patent is extended or adjusted under 35 U.S.C. 154(b) by 99 days.

This patent is subject to a terminal disclaimer.

(21) Appl. No.: 15/520,722

(22) PCT Filed: Oct. 23, 2014

(86) PCT No.: PCT/AU2014/000999
§ 371 (c)(1),
(2) Date: Apr. 20, 2017

(87) PCT Pub. No.: WO2016/061608
PCT Pub. Date: Apr. 28, 2016

(65) Prior Publication Data
US 2018/0072803 A1    Mar. 15, 2018

(51) Int. Cl.
*C07K 16/28* (2006.01)
*C12N 5/16* (2006.01)

(52) U.S. Cl.
CPC .............. *C07K 16/28* (2013.01); *C12N 5/16* (2013.01); *C07K 2317/14* (2013.01); *C07K 2317/24* (2013.01); *C07K 2317/52* (2013.01); *C07K 2317/53* (2013.01); *C07K 2317/54* (2013.01); *C07K 2317/55* (2013.01); *C07K 2317/56* (2013.01); *C07K 2317/565* (2013.01); *C07K 2317/567* (2013.01); *C07K 2317/622* (2013.01)

(58) Field of Classification Search
CPC ..................................... C07K 16/28
USPC ..................................... 530/387.3
See application file for complete search history.

(56) References Cited

U.S. PATENT DOCUMENTS 5,622,835 A    4/1997    Walker et al.

FOREIGN PATENT DOCUMENTS

| WO | 1990014433 A1 | 11/1990 |
| WO | 2015106311 A1 | 7/2015 |
| WO | 2016112423 A1 | 7/2016 |
| WO | 2016168885 A1 | 10/2016 |

OTHER PUBLICATIONS

Carter, et al., "Biodistributions of intact monoclonal antibodies and fragments of BLCA-38, a new prostate cancer directed antibody", Cancer Immunol Immunother 53, 533-542 (2004).
Khatri, et al., "Promise of BLCA38 as a Targeting Antibody for Tissue-Specific Gene Delivery to Prostate Cancer", Austral-Asian J Cancer 9(3), 195-203 (2010).
Patent Cooperation Treaty, International Searching Authority, Search Report and Written Opinion for PCT/ AU2014/000999, 10 pages, Dec. 3, 2014.
Russell, et al., "Immunohistochemical characterisation of the monoclonal antibody BLCA-38 for the detection of prostate cancer", Cancer Immunol Immunother 53, 995-1004 (2004).
Budapest Treaty, "MIL-38 Hybridoma Clone™1F5C11—Accession No. CBA20140026", Budapest Treaty on the International Recognition of The Deposit of Microorganisms for the Purposes of Patent Procedure—Receipt in the case of an Original Deposit issued pursuant to Rule 7.1 by the International Depository Authority, 3 pg, Sep. 26, 2014.

*Primary Examiner* — Sean E Aeder
(74) *Attorney, Agent, or Firm* — Viksnins Harris Padys Malen LLP

(57) ABSTRACT

The present application is directed to an invention based on the discovery that the BLCA-38 antibody is actually an antibody population comprising two distinct monoclonal antibodies. The claims define an isolated antibody population comprising first antibodies and/or antigen binding fragments thereof defined by specific heavy chain and light chain variable regions and wherein the antibody population does not contain second antibodies defined by specific light chain variable regions. The claims also define hybridoma cells, cultures capable of producing such antibody populations, compositions comprising such antibody populations, nucleic acid molecules encoding such antibodies, vectors, host cells thereof, and processes for production of the antibody populations of the invention.

13 Claims, 14 Drawing Sheets

Specification includes a Sequence Listing.

SEQUENCE LISTING

```
<160> NUMBER OF SEQ ID NOS: 10

<210> SEQ ID NO 1
<211> LENGTH: 1386
<212> TYPE: DNA
<213> ORGANISM: Mus musculus

<400> SEQUENCE: 1
atggcttggg tgtggaccct gctattcctg atggctgctg cccaaagtat ccaagcacag      60
atccagttgg tgcagtctgg acctgagctg aagaagcctg gagagacagt caagatctcc     120
tgcaaggctt ctggttatgc cttcacagac tattcaatga actgggtgaa gcaggctcca     180
ggaaagggtt taaggtggat gggctggata aacactgaga ctggtgagcc aacatataca     240
gatgacttca agggacggtt tgccttctct ttggaaacct ctgccagcac tgccttttg      300
```

| | | |
|---|---|---|
| cagatcaaca acctcagaaa tgaagacacg gctacatatt tctgtgctag acactatgat | 360 | |
| tacgggggt ttccttactg gggccaaggg actctggtca ctgtctctgc agccaaaacg | 420 | |
| acacccccat ctgtctatcc actggcccct ggatctgctg cccaaactaa ctccatggtg | 480 | |
| accctgggat gcctggtcaa gggctatttc cctgagccag tgacagtgac ctggaactct | 540 | |
| ggatccctgt ccagcggtgt gcacaccttc ccagctgtcc tgcagtctga cctctacact | 600 | |
| ctgagcagct cagtgactgt ccctccagc acctggccca gcgagaccgt cacctgcaac | 660 | |
| gttgcccacc cggccagcag caccaaggtg gacaagaaaa ttgtgcccag ggattgtggt | 720 | |
| tgtaagcctt gcatatgtac agtcccagaa gtatcatctg tcttcatctt ccccccaaag | 780 | |
| cccaaggatg tgctcaccat tactctgact cctaaggtca cgtgtgttgt ggtagacatc | 840 | |
| agcaaggatg atcccgaggt ccagttcagc tggtttgtag atgatgtgga ggtgcacaca | 900 | |
| gctcagacgc aaccccggga ggagcagttc aacagcactt ccgctcagt cagtgaactt | 960 | |
| cccatcatgc accaggactg gctcaatggc aaggagttca atgcagggt caacagtgca | 1020 | |
| gctttccctg cccccatcga gaaaaccatc tccaaaacca aggcagacc gaaggctcca | 1080 | |
| caggtgtaca ccattccacc tcccaaggag cagatggcca aggataaagt cagtctgacc | 1140 | |
| tgcatgataa cagacttctt ccctgaagac attactgtgg agtggcagtg gaatgggcag | 1200 | |
| ccagcggaga actacaagaa cactcagccc atcatggaca cagatggctc ttacttcgtc | 1260 | |
| tacagcaagc tcaatgtgca aagagcaac tgggaggcag gaatacttt cacctgctct | 1320 | |
| gtgttacatg agggcctgca caaccaccat actgagaaga gcctctccca ctctcctggt | 1380 | |
| aaatga | 1386 | |

<210> SEQ ID NO 2
<211> LENGTH: 705
<212> TYPE: DNA
<213> ORGANISM: Mus musculus

<400> SEQUENCE: 2

| | | |
|---|---|---|
| atgagtgtgc tcactcaggt cctggcgttg ctgctgctgt ggcttacagg tgccagatgt | 60 | |
| gacatccaga tgactcagtc tccagcctcc ctatctgcat ctgtgggaga aactgtcacc | 120 | |
| atcacatgtc gagcaagtgg gaatgttcac aattatttag catggtatca gcagaaacag | 180 | |
| ggaaaatctc ctcaactcct ggtctatact gcaaaaacct tagcagatgg tgtgccatca | 240 | |
| aggttcagtg gcagtggatc aggaacacaa tattctctca gatcaatag cctgcagcct | 300 | |
| gaagattttg ggacttatta ctgtcaacat ttttggagta tccgtggac gttcggtgga | 360 | |
| ggcaccaagc tggaaatcaa acgggctgat gctgcaccaa ctgtatccat cttcccacca | 420 | |
| tccagtgagc agttaacatc tggaggtgcc tcagtcgtgt gcttcttgaa caacttctac | 480 | |
| cccaaagaca tcaatgtcaa gtggaagatt gatggcagtg aacgacaaaa tggcgtcctg | 540 | |
| aacagttgga ctgatcagga cagcaaagac agcacctaca gcatgagcag cacctcacg | 600 | |
| ttgaccaagg acgagtatga acgacataac agctatacct gtgaggccac tcacaagaca | 660 | |
| tcaacttcac ccattgtcaa gagcttcaac aggaatgagt gttag | 705 | |

<210> SEQ ID NO 3
<211> LENGTH: 461
<212> TYPE: PRT
<213> ORGANISM: Mus musculus

<400> SEQUENCE: 3

Met Ala Trp Val Trp Thr Leu Leu Phe Leu Met Ala Ala Ala Gln Ser

```
1               5                   10                  15
Ile Gln Ala Gln Ile Gln Leu Val Gln Ser Gly Pro Glu Leu Lys Lys
                20                  25                  30

Pro Gly Glu Thr Val Lys Ile Ser Cys Lys Ala Ser Gly Tyr Ala Phe
                35                  40                  45

Thr Asp Tyr Ser Met Asn Trp Val Lys Gln Ala Pro Gly Lys Gly Leu
        50                  55                  60

Arg Trp Met Gly Trp Ile Asn Thr Glu Thr Gly Glu Pro Thr Tyr Thr
65                  70                  75                  80

Asp Asp Phe Lys Gly Arg Phe Ala Phe Ser Leu Glu Thr Ser Ala Ser
                85                  90                  95

Thr Ala Phe Leu Gln Ile Asn Asn Leu Arg Asn Glu Asp Thr Ala Thr
                100                 105                 110

Tyr Phe Cys Ala Arg His Tyr Asp Tyr Gly Gly Phe Pro Tyr Trp Gly
                115                 120                 125

Gln Gly Thr Leu Val Thr Val Ser Ala Ala Lys Thr Thr Pro Pro Ser
        130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
                180                 185                 190

Val Leu Gln Ser Asp Leu Tyr Thr Leu Ser Ser Ser Val Thr Val Pro
                195                 200                 205

Ser Ser Thr Trp Pro Ser Glu Thr Val Thr Cys Asn Val Ala His Pro
210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
                260                 265                 270

Val Thr Cys Val Val Asp Ile Ser Lys Asp Asp Pro Glu Val Gln
        275                 280                 285

Phe Ser Trp Phe Val Asp Asp Val Glu Val His Thr Ala Gln Thr Gln
        290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
                340                 345                 350

Thr Lys Gly Arg Pro Lys Ala Pro Gln Val Tyr Thr Ile Pro Pro Pro
        355                 360                 365

Lys Glu Gln Met Ala Lys Asp Lys Val Ser Leu Thr Cys Met Ile Thr
        370                 375                 380

Asp Phe Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Thr Asp Gly
                405                 410                 415

Ser Tyr Phe Val Tyr Ser Lys Leu Asn Val Gln Lys Ser Asn Trp Glu
                420                 425                 430
```

Ala Gly Asn Thr Phe Thr Cys Ser Val Leu His Glu Gly Leu His Asn
        435                 440                 445

His His Thr Glu Lys Ser Leu Ser His Ser Pro Gly Lys
    450                 455                 460

<210> SEQ ID NO 4
<211> LENGTH: 234
<212> TYPE: PRT
<213> ORGANISM: Mus musculus

<400> SEQUENCE: 4

Met Ser Val Leu Thr Gln Val Leu Ala Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Gly Asn
        35                  40                  45

Val His Asn Tyr Leu Ala Trp Tyr Gln Gln Lys Gln Gly Lys Ser Pro
    50                  55                  60

Gln Leu Leu Val Tyr Thr Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Thr Tyr Tyr Cys Gln His Phe Trp
            100                 105                 110

Ser Asn Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 5
<211> LENGTH: 717
<212> TYPE: DNA
<213> ORGANISM: Mus musculus

<400> SEQUENCE: 5
atgggcatca agatggagtc acagactcag gtctttgtat acatgttgct gtggttgtct      60
ggtgttgatg agacattgt gatgacccag tctcaaaagt tcatgtccac atcaatagga     120
gacagggtca gcgtcaccctg caaggccagt cagaatgtgg gttctcatgt agcctggttt     180
cagcagaaac cagggcaatc tcctaaagca ctgatttact cggcatccta ccggtacagc     240
ggagtcactg atcgcttcac aggcagtgga tctgggacag atttcactct caccatcaac     300
aatgtgcagt ctgaagactt ggcagagtat ttctgtcagc aatataacag ttttccattc     360

```
acgttcggtt cggggacaaa gttggaaata aaacgggctg atgctgcacc aactgtatcc    420
atcttcccac catccagtga gcagttaaca tctggaggtg cctcagtcgt gtgcttcttg    480
aacaacttct accccaaaga catcaatgtc aagtggaaga ttgatggcag tgaacgacaa    540
aatggcgtcc tgaacagttg gactgatcag gacagcaaag acagcaccta cagcatgagc    600
agcaccctca cgttgaccaa ggacgagtat gaacgacata cagctatacc tgtgaggcc    660 actcacaaga catcaacttc acccattgtc aagagcttca caggaatga gtgttag       717
```

<210> SEQ ID NO 6
<211> LENGTH: 238
<212> TYPE: PRT
<213> ORGANISM: Mus musculus

<400> SEQUENCE: 6

```
Met Gly Ile Lys Met Glu Ser Gln Thr Gln Val Phe Val Tyr Met Leu
1               5                   10                  15

Leu Trp Leu Ser Gly Val Asp Gly Asp Ile Val Met Thr Gln Ser Gln
                20                  25                  30

Lys Phe Met Ser Thr Ser Ile Gly Asp Arg Val Ser Val Thr Cys Lys
            35                  40                  45

Ala Ser Gln Asn Val Gly Ser His Val Ala Trp Phe Gln Gln Lys Pro
        50                  55                  60

Gly Gln Ser Pro Lys Ala Leu Ile Tyr Ser Ala Ser Tyr Arg Tyr Ser
65                  70                  75                  80

Gly Val Thr Asp Arg Phe Thr Gly Ser Gly Ser Gly Thr Asp Phe Thr
                85                  90                  95

Leu Thr Ile Asn Asn Val Gln Ser Glu Asp Leu Ala Glu Tyr Phe Cys
            100                 105                 110

Gln Gln Tyr Asn Ser Phe Pro Phe Thr Phe Gly Ser Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

<210> SEQ ID NO 7
<211> LENGTH: 1404
<212> TYPE: DNA
<213> ORGANISM: Artificial Sequence
<220> FEATURE:
<223> OTHER INFORMATION: Chimeric Antibody Sequence

<400> SEQUENCE: 7

```
atggcttggg tgtggacact gctgttcctg atgctgctg cccagagtat tcaggctcag    60
attcagctgg tccagagcgg tcccgagctg aagaagccag gcgagaccgt gaagatctcc   120
```

```
tgcaaggcca gcggctacgc tttcacagac tattctatga actgggtgaa gcaggcccca    180
ggcaagggcc tgaggtggat gggctggatc aataccgaga caggcgagcc cacctacaca    240
gacgatttca agggccggtt cgcttttttcc ctggagacct ctgcctccac agctttttctg   300
cagatcaaca atctgagaaa cgaggacacc gccacatact ctgcgctag gcactacgat     360
tatggcggct ttccttattg gggccagggc accctggtga cagtgtccag cgcctctacc    420
aagggcccat ccgtgtttcc actggctccc tcttccaaga gcacctctgg cggcacagcc    480
gctctgggct gtctggtgaa ggattacttc ccagagcccg tgacagtgtc ttggaactcc    540
ggcgccctga cctccggagt gcatacattt cccgctgtgc tgcagagctc tggcctgtac    600
agcctgtcca gcgtggtgac cgtgccttct ccagcctgg gcacccagac atatatctgc    660
aacgtgaatc acaagccatc caatacaaag gtggacaaga aggtggagcc caagagctgt    720
gataagaccc atacatgccc cccttgtcct gctccagagc tgctgggagg acctagcgtg    780
ttcctgtttc cacccaagcc taaggacacc ctgatgatct ctaggacccc cgaggtgaca    840
tgcgtggtgg tggacgtgtc ccacgaggat cctgaggtga agttcaactg gtacgtggat    900
ggcgtggagg tgcataatgc taagaccaag cctaggagg agcagtacaa cagcaccctat   960
cgggtggtgt ctgtgctgac agtgctgcac caggactggc tgaacggcaa ggagtataag   1020
tgcaaggtga gcaataaggc cctgcccgct cctatcgaga agaccatctc taaggccaag   1080
ggccagcctc gggagccaca ggtgtacaca ctgcctccaa gcagagacga gctgaccaag   1140
aaccaggtgt ctctgacatg tctggtgaag ggcttctatc cttctgatat cgctgtggag   1200
tgggagtcca atggccagcc agagaacaat tacaagacca cccccctgt gctggacagc   1260
gatggctctt tctttctgta ttccaagctg accgtggata gagcaggtg gcagcagggc   1320
aacgtgttct cctgtagcgt gatgcacgag gcactgcaca accactacac tcagaaatcc   1380
ctgtccctgt cacctggcaa atga                                          1404

<210> SEQ ID NO 8
<211> LENGTH: 705
<212> TYPE: DNA
<213> ORGANISM: Artificial Sequence
<220> FEATURE:
<223> OTHER INFORMATION: Chimeric Antibody Sequence

<400> SEQUENCE: 8
atgagcgtgc tgacccaggt gctggccctg ctgctgctgt ggctgaccgg agcccgttgc    60
gacatccaga tgacccagtc ccctgcctct ctgtccgcca gcgtgggcga gaccgtgaca    120
atcacctgca gagcctctgg caacgtgcac aattacctgg cttggtatca gcagaagcag    180
ggcaagtccc cacagctgct ggtgtacaca gccaagaccc tggctgacgg cgtgcccagc    240
aggttctctg gctccggcag cggcacacag tatagcctga agatcaactc tctgcagcct    300
gaggattttg gcacctacta ttgccagcat ttctggtcta atccatggac atttggcggc    360
ggcaccaagc tggagatcaa aggacagtg gccgctccct ccgtgttcat ctttccccct    420
agcgacgagc agctgaagtc tggcaccgct tccgtggtgt gcctgctgaa caatttctac    480
cctcgggagg ccaaggtgca gtggaaggtg gataacgctc tgcagtctgg caattcccag    540
gagagcgtga cagagcagga ctctaaggat tccacctata gcctgtccag cacactgacc    600
ctgtccaagg ccgactacga gaagcacaag gtgtatgctt gtgaggtcac tcaccagggg   660
ctgtcaagtc cagtcacaaa gtccttcaat agggggggaat gctga                  705
```

<210> SEQ ID NO 9
<211> LENGTH: 467
<212> TYPE: PRT
<213> ORGANISM: Artificial Sequence
<220> FEATURE:
<223> OTHER INFORMATION: Chimeric Antibody Sequence

<400> SEQUENCE: 9

```
Met Ala Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Ala Phe
        35                  40                  45

Thr Asp Tyr Ser Met Asn Trp Val Lys Gln Ala Pro Gly Lys Gly Leu
    50                  55                  60

Arg Trp Met Gly Trp Ile Asn Thr Glu Thr Gly Glu Pro Thr Tyr Thr
65                  70                  75                  80

Asp Asp Phe Lys Gly Arg Phe Ala Phe Ser Leu Glu Thr Ser Ala Ser
                85                  90                  95

Thr Ala Phe Leu Gln Ile Asn Asn Leu Arg Asn Glu Asp Thr Ala Thr
            100                 105                 110

Tyr Phe Cys Ala Arg His Tyr Asp Tyr Gly Gly Phe Pro Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365
```

```
Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Lys
465

<210> SEQ ID NO 10
<211> LENGTH: 234
<212> TYPE: PRT
<213> ORGANISM: Artificial Sequence
<220> FEATURE:
<223> OTHER INFORMATION: Chimeric Antibody Sequence

<400> SEQUENCE: 10

Met Ser Val Leu Thr Gln Val Leu Ala Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Gly Asn
        35                  40                  45

Val His Asn Tyr Leu Ala Trp Tyr Gln Gln Lys Gln Gly Lys Ser Pro
    50                  55                  60

Gln Leu Leu Val Tyr Thr Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Thr Tyr Tyr Cys Gln His Phe Trp
            100                 105                 110

Ser Asn Pro Trp Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

MONOCLONAL ANTI-GPC-1 ANTIBODIES AND USES THEREOF

TECHNICAL FIELD

The present invention relates generally to the fields of immunology and medicine. More specifically, the present invention relates to monoclonal antibodies and uses thereof.

BACKGROUND

Cancer is a leading cause of death worldwide with lung, breast, colorectal, stomach, and prostate cancer causing the majority of deaths. Prostate cancer is the most commonly occurring tumour in males and is second only to lung cancer in mortality. Treatment with surgery and/or radiotherapy is successful in many patients if prostate cancer is diagnosed early. However, many patients with advanced disease and a sizeable proportion of all prostate cancer patients eventually develop metastatic disease following localised therapy.

Antibodies (Abs) are a primary tool in the field of targeted therapy and diagnosis due to their binding specificity/affinity and potential for effector properties upon interaction with their cognate antigens. Increasing numbers of Abs have been approved for medical use and many are under clinical evaluation. Antibodies can be effective diagnostics to identify individuals with a predisposition to diseases such as prostate cancer and/or to diagnose such diseases. In addition, the therapeutic use of some antibodies has been shown to reduce tumour size and extend the survival of afflicted patients.

U.S. Pat. No. 5,622,836 to Walker et al. discloses an antibody named BLCA-38 (BLCA—"bladder cancer"). The document teaches that BLCA-38 is a monoclonal antibody specific for an unknown antigen expressed by bladder carcinoma cells. BLCA-38 is also taught to show specificity for human ovarian and colonic cancer cell lines, as well as some melanoma cell lines, but not to lymphoid (T lymphoid or B lymphoid) and leukemic cell lines.

Subsequently, Russell et al. (2004) (Russell et al., "Cytotoxic properties of immunoconjugates containing melittin-like peptide 101 against prostate cancer: in vitro & in vivo studies". Cancer Immunol Immunother 2004: 53(5): 411-421) published a study in which BLCA-38 was used to target a cytotoxic peptide to prostate cancer cells. The authors indicate that BLCA-38 is a murine monoclonal antibody raised against the human bladder cancer cell line UCRU-BL-17CL.

A further publication by Russell et al. in 2004 (Russell et al., "Immunohistochemical characterization of the monoclonal antibody, BLCA38, for the detection of prostate cancer". Cancer Immunol Immunother 2004: 53: 995-1004) also teaches that BLCA-38 is a murine monoclonal antibody raised against a human bladder cell line which is capable of binding to bladder carcinoma cells, prostate cancer cells, and vulval epidermoid cells, but not to breast cancer cells. The article indicates that BLCA-38 is specific for an antigen of approximately 30 kDa in size that is difficult to characterise or identify.

Carter et al. (2004) (Carter et al., "Biodistributions of intact monoclonal antibodies and fragments of BLCA38, a new prostate cancer directed antibody". Cancer Immunol Immunother 2004: 53:533-542) analysed timing and dosage for targeting therapeutic agents to prostate cancer cells using BLCA-38, also indicating that it is a murine monoclonal antibody targeting an antigen of around 30 kDa expressed on the cell surface and in the cytoplasm. The authors state that the nature of the antigen is elusive, and indicate that it is expressed on bladder and prostate cancer cells.

An article by Khatri et al. published in 2010 (Khatri et al. "Promise of BLCA38 as a Targeting Antibody for Tissue-Specific Gene Delivery to Prostate Cancer". Austral-Asian J. Cancer 2010: 9(3): 195-203) reiterated that BLCA-38 is a murine monoclonal antibody specific for prostate cancer cells. The authors reveal that although BLCA-38 is not internalised upon binding to its antigen, conjugation with a virus facilitated internalisation of the antibody resulting in increased expression of the reporter gene.

Despite the promise that antibodies offer as diagnostic and therapeutic agents, a need continues to exist for more effective agents to diagnose and/or treat various forms of cancer, including prostate cancer.

SUMMARY OF THE INVENTION

The present inventors have surprisingly identified that the BLCA-38 antibody referred to and used in the aforementioned prior art is not a discrete monoclonal antibody as indicated, but rather a combination of two distinct monoclonal antibodies in a mixed population. The present inventors have determined that the hybridoma used to generate the BLCA-38 antibody, a representative sample of which was deposited at the American Tissue Type Culture Collection under accession number HB11785, is a mixed population of hybridoma cells, which produces at least two discrete antibody species. Only one of these antibody species is capable of binding to the relevant target antigen present on some forms of cancer cells, whilst the second species cannot.

The unexpected determination that BLCA-38 as referred to in the prior art represents a mixed hybridoma/antibody population has facilitated the generation of a monoclonal hybridoma capable of producing a single population of monoclonal antibodies with binding specificity for the target antigen on various forms of cancer cells. Apart from circumventing the unnecessary production and application of an ineffectual antibody, data provided in the Examples of the present specification indicates that use of the monoclonal hybridoma/single monoclonal antibody according to the present invention can allow for the generation of a stronger signal compared to the mixed population of the prior art when equivalent amounts of antibody are applied.

In a first embodiment the present invention provides an isolated antibody or antigen binding fragment thereof comprising a heavy chain variable region and a light chain variable region, wherein: (a) the heavy chain variable region comprises: a complementarity determining region 1 (CDR1) comprising or consisting of an amino acid sequence defined by positions 50-54 of SEQ ID NO: 3; a complementarity determining region 2 (CDR2) comprising or consisting of an amino acid sequence defined by positions 69-85 of SEQ ID NO: 3; a complementarity determining region 3 (CDR3) comprising or consisting of an amino acid sequence defined by positions 118-126 of SEQ ID NO: 3; and (b) the light chain variable region comprises: a complementarity determining region 1 (CDR1) comprising or consisting of an amino acid sequence defined by positions 44-54 of SEQ ID NO: 4; a complementarity determining region 2 (CDR2) comprising or consisting of an amino acid sequence defined by positions 70-76 of SEQ ID NO: 4; a complementarity determining region 3 (CDR3) comprising or consisting of an amino acid sequence defined by positions 109-117 of SEQ ID NO: 4.

The isolated antibody or antigen binding fragment thereof may further comprise: (a) one or more heavy chain variable region FR (framework regions) as defined by a sequence selected from any one or more of: residues 20-49 of SEQ ID NO: 3, residues 55-68 of SEQ ID NO: 3, residues 86-117 of SEQ ID NO: 3, and/or residues 127-137 of SEQ ID NO: 3; and/or (b) one or more light chain variable region FR (framework regions) as defined by a sequence selected from any one or more of: residues 21-43 of SEQ ID NO: 4, residues 55-69 of SEQ ID NO: 4, residues 77-108 of SEQ ID NO: 4, and/or residues 118-127 of SEQ ID NO: 4.

The isolated antibody or antigen binding fragment thereof may further comprise any one or more of: (a) a heavy chain constant domain sequence as defined by positions 138-461 of SEQ ID NO: 3; (b) a light chain constant domain sequence as defined by positions 128-234 of SEQ ID NO: 4; (c) a hinge region.

The isolated antibody or antigen binding fragment thereof may have binding specificity for an epitope present in glypican-1 heparan sulfate proteoglycan (GPC-1).

The antibody may be an IgG isotype antibody. The antibody may be an IgG1 isotype antibody. The antibody or antigen binding fragment may comprise a detectable label.

The detectable label may be any one or more of a fluorescent label, a radiolabel, biotin, or avidin.

The antibody may be any one or more of a monoclonal antibody, a humanised antibody, a chimeric antibody, a multimeric antibody, and/or a synthetic antibody.

The antibody may be a bi-specific antibody, avibody, diabody, tribody, tetrabody, nanobody, single domain antibody, VHH domain, human antibody, fully humanized antibody, partially humanized antibody, anticalin, adnectin, or affibody.

The antibody may be a chimeric antibody comprising a heavy chain variable region and a light chain variable region, wherein: (a) the heavy chain variable region comprises: a complementarity determining region 1 (CDR1) comprising or consisting of an amino acid sequence defined by positions 50-54 of SEQ ID NO: 9; a complementarity determining region 2 (CDR2) comprising or consisting of an amino acid sequence defined by positions 69-85 of SEQ ID NO: 9; a complementarity determining region 3 (CDR3) comprising or consisting of an amino acid sequence defined by positions 118-126 of SEQ ID NO: 9; and (b) the light chain variable region comprises: a complementarity determining region 1 (CDR1) comprising or consisting of an amino acid sequence defined by positions 44-54 of SEQ ID NO: 10; a complementarity determining region 2 (CDR2) comprising or consisting of an amino acid sequence defined by positions 70-76 of SEQ ID NO: 10; a complementarity determining region 3 (CDR3) comprising or consisting of an amino acid sequence defined by positions 109-117 of SEQ ID NO: 10.

The antibody may be a chimeric antibody comprising a heavy chain variable region and a light chain variable region, wherein: (a) the heavy chain variable region comprises: a complementarity determining region 1 (CDR1) comprising or consisting of an amino acid sequence having at least 80%, at least 85%, at least 90%, or at least 95% sequence homology with an amino acid sequence defined by positions 50-54 of SEQ ID NO: 9; a complementarity determining region 2 (CDR2) comprising or consisting of an amino acid sequence having at least 80%, at least 85%, at least 90%, or at least 95% sequence homology with an amino acid sequence defined by positions 69-85 of SEQ ID NO: 9; a complementarity determining region 3 (CDR3) comprising or consisting of an amino acid sequence having at least 80%, at least 85%, at least 90%, or at least 95% sequence homology with an amino acid sequence defined by positions 118-126 of SEQ ID NO: 9; and (b) the light chain variable region comprises: a complementarity determining region 1 (CDR1) comprising or consisting of an amino acid sequence having at least 80%, at least 85%, at least 90%, or at least 95% sequence homology with an amino acid sequence defined by positions 44-54 of SEQ ID NO: 10; a complementarity determining region 2 (CDR2) comprising or consisting of an amino acid sequence having at least 80%, at least 85%, at least 90%, or at least 95% sequence homology with an amino acid sequence defined by positions 70-76 of SEQ ID NO: 10; a complementarity determining region 3 (CDR3) comprising or consisting of an amino acid sequence having at least 80%, at least 85%, at least 90%, or at least 95% sequence homology with an amino acid sequence defined by positions 109-117 of SEQ ID NO: 10.

The antibody may be a chimeric antibody comprising: (a) a heavy chain comprising or consisting of an amino acid sequence as defined in residues 20-467 of SEQ ID NO: 9; and (b) a light chain comprising or consisting of an amino acid sequence as defined in residues 21-234 of SEQ ID NO: 10.

The antibody may be a chimeric antibody comprising: (a) a heavy chain comprising or consisting of an amino acid sequence having at least 80%, at least 85%, at least 90%, or at least 95% sequence homology with an amino acid sequence as defined in residues 20-467 of SEQ ID NO: 9; and (b) a light chain comprising or consisting of an amino acid sequence having at least 80%, at least 85%, at least 90%, or at least 95% sequence homology with an amino acid sequence as defined in residues 21-234 of SEQ ID NO: 10.

The chimeric antibody may comprise a detectable label. The detectable label may be any one or more of a fluorescent label, a radiolabel, biotin, or avidin.

The antigen binding fragment may be any one or more of a single chain variable fragment (scFv), a variable domain (Fv) fragment, a fragment antigen binding (Fab) fragment, a F(ab)2 fragment, a peptide, or a proteolytic fragment containing an epitope binding region.

The antibody may comprise or consist of a heavy chain sequence as defined by positions 20-461 of SEQ ID NO: 3 and a light chain sequence as defined by positions 21-234 of SEQ ID NO: 4.

In a second embodiment the present invention provides an isolated antigen binding variant or derivative of an antibody as defined in the first embodiment, wherein the variant or derivative and the antibody as defined in the first embodiment are capable of specifically binding to the same antigen.

Any one or more heavy chain CDR1, CDR2, and/or CDR3 amino acid sequence/s of the variant or derivative, and/or any one or more light chain CDR1, CDR2, and/or CDR3 amino acid sequence/s of the variant or derivative, may comprise one, two, three, four or five amino acid deletion/s, insertion/s, and/or substitution/s compared to an otherwise corresponding CDR sequence of amino acids present in an antibody as defined in the first embodiment.

The isolated variant or derivative may comprise a heavy chain variable region and a light chain variable region, wherein: (a) the heavy chain variable region comprises: a complementarity determining region 1 (CDR1) comprising or consisting of an amino acid sequence having at least 80%, at least 85%, at least 90%, or at least 95% sequence homology with an amino acid sequence defined by positions 50-54 of SEQ ID NO: 3; a complementarity determining region 2 (CDR2) comprising or consisting of an amino acid sequence having at least 80%, at least 85%, at least 90%, or at least 95% sequence homology with an amino acid sequence defined by positions 69-85 of SEQ ID NO: 3; a complementarity determining region 3 (CDR3) comprising or consisting of an amino acid sequence having at least 80%, at least 85%, at least 90%, or at least 95% sequence homology with an amino acid sequence defined by positions 118-126 of SEQ ID NO: 3; and (b) the light chain variable region comprises: a complementarity determining region 1 (CDR1) comprising or consisting of an amino acid sequence having at least 80%, at least 85%, at least 90%, or at least 95% sequence homology with an amino acid sequence defined by positions 44-54 of SEQ ID NO: 4; a complementarity determining region 2 (CDR2) comprising or consisting of an amino acid sequence having at least 80%, at least 85%, at least 90%, or at least 95% homology with an amino acid sequence defined by positions 70-76 of SEQ ID NO: 4; a complementarity determining region 3 (CDR3) comprising or consisting of an amino acid sequence having at least 80%, at least 85%, at least 90%, or at least 95% sequence homology with an amino acid sequence defined by positions 109-117 of SEQ ID NO: 4.

The variant or derivative may comprise: (a) at least one heavy chain variable region FR (framework region) selected from a heavy chain variable region FR comprising or consisting of an amino acid sequence: having at least 80%, at least 85%, at least 90%, or at least 95% sequence homology with residues 20-49 of SEQ ID NO: 3, at least 80%, at least 85%, at least 90%, or at least 95% sequence homology with residues 55-68 of SEQ ID NO: 3, at least 80%, at least 85%, at least 90%, or at least 95% sequence homology with residues 86-117 of SEQ ID NO: 3, at least 80%, at least 85%, at least 90%, or at least 95% sequence homology with residues 127-137 of SEQ ID NO: 3; and/or (b) at least one light chain variable region FR (framework region) selected from a light chain variable region FR comprising or consisting of an amino acid sequence: having at least 80%, at least 85%, at least 90%, or at least 95% sequence homology with residues 21-43 of SEQ ID NO: 4, at least 80%, at least 85%, at least 90%, or at least 95% sequence homology with residues 55-69 of SEQ ID NO: 4, at least 80%, at least 85%, at least 90%, or at least 95% sequence homology with residues 77-108 of SEQ ID NO: 4, and/or at least 80%, at least 85%, at least 90%, or at least 95% sequence homology with residues 118-127 of SEQ ID NO: 4.

The variant or derivative may comprise any one or more of: (a) a heavy chain constant domain sequence comprising or consisting of an amino acid sequence having at least 80%, at least 85%, at least 90%, or at least 95% homology with an amino acid sequence as defined by positions 138-461 of SEQ ID NO: 3; (b) a light chain constant domain sequence comprising or consisting of an amino acid sequence having at least 80%, at least 85%, at least 90%, or at least 95% homology with an amino acid sequence as defined by positions 128-234 of SEQ ID NO: 4; (c) a hinge region.

The variant or derivative may have binding specificity for an epitope present in glypican-1 heparan sulfate proteoglycan (GPC-1).

The variant or derivative may be an IgG isotype antibody. The isolated antibody variant or derivative may be an IgG1 isotype antibody.

The variant or derivative may comprise a detectable label. The detectable label may be any one or more of a fluorescent label, a radiolabel, biotin, or avidin.

The variant or derivative may be any one or more of a monoclonal antibody, a humanised antibody, a chimeric antibody, a multimeric antibody, and/or a synthetic antibody.

In a third embodiment, the present invention provides hybridoma cells capable of producing an antibody or antigen binding fragment thereof as defined in the first embodiment, or an antigen binding variant or derivative as defined in the second embodiment.

The hybridoma cells may be those deposited at Cellbank Australia on 22 Aug. 2014 and allocated accession number CBA20140026.

In a fourth embodiment, the present invention provides a cell culture comprising a single species of hybridoma cells capable of producing a single species of antibody or antigen binding fragment thereof as defined in the first embodiment, or a single species of an antigen binding variant or derivative as defined in the second embodiment.

The hybridoma cells may be deposited at Cellbank Australia under accession number CBA20140026.

In a fifth embodiment, the present invention provides a cell culture comprising multiple species of hybridoma cells, wherein: (a) the cell culture comprises hybridoma cells as defined in the third embodiment; and (b) the cell culture does not comprise hybridoma cells that produce an antibody comprising a:
light chain variable region that comprises any one or more of:
  a complementarity determining region 1 (CDR1) comprising or consisting of an amino acid sequence defined by positions 48-58 of SEQ ID NO: 6;
  a complementarity determining region 2 (CDR2) comprising or consisting of an amino acid sequence defined by positions 74-80 of SEQ ID NO: 6;
  a complementarity determining region 3 (CDR3) comprising or consisting of an amino acid sequence defined by positions 113-121 of SEQ ID NO: 6.

The cell culture may not comprise hybridoma cells that produce an antibody comprising one or more light chain variable region FR (framework regions) as defined by a sequence selected from any one or more of: residues 25-47 of SEQ ID NO: 6, residues 59-73 of SEQ ID NO: 6, residues 81-112 of SEQ ID NO: 6, residues 122-131 of SEQ ID NO: 6.

The multiple species of hybridoma cells in the cell culture may be each capable of producing a single species of antibody or antigen binding fragment thereof as defined in the first embodiment, or a single species of an antigen binding variant or derivative as defined in the second embodiment.

In a sixth embodiment, the present invention provides a composition comprising a single species of antibody or antigen binding fragment thereof as defined in the first embodiment, or a single species of an antigen binding variant or derivative as defined in the second embodiment.

In a seventh embodiment, the present invention provides a composition comprising a mixture of different antibody species or antigen binding fragments thereof, wherein: (a) the composition comprises a single species of antibody or antigen binding fragment thereof as defined in the first embodiment, or a single species of an antigen binding variant or derivative as defined in the second embodiment; and (b) the composition does not comprise an antibody comprising a light chain variable region that comprises any one or more of:
  a complementarity determining region 1 (CDR1) comprising or consisting of an amino acid sequence defined by positions 48-58 of SEQ ID NO: 6;
  a complementarity determining region 2 (CDR2) comprising or consisting of an amino acid sequence defined by positions 74-80 of SEQ ID NO: 6;

a complementarity determining region 3 (CDR3) comprising or consisting of an amino acid sequence defined by positions 113-121 of SEQ ID NO: 6.

The mixture of different antibody species or antigen binding fragments thereof may each have binding specificity for an epitope present in glypican-1 heparan sulfate proteoglycan (GPC-1).

In an eighth embodiment, the present invention provides a nucleic acid molecule encoding an antibody or antigen binding fragment thereof as defined in the first embodiment, or an antigen binding variant or derivative as defined in the second embodiment.

The nucleic acid molecule may comprise or consist of a sequence as defined in SEQ ID NO: 1.

The nucleic acid molecule may comprise or consist of a sequence as defined in SEQ ID NO: 2.

The antibody or antigen binding fragment thereof, or antigen binding variant or derivative, may each have binding specificity for an epitope present in glypican-1 heparan sulfate proteoglycan (GPC-1).

In a ninth embodiment, the present invention provides a vector comprising a nucleic acid molecule as defined in the eighth embodiment.

In a tenth embodiment, the present invention provides a host cell comprising a vector as defined in the ninth embodiment.

In an eleventh embodiment, the present invention provides a process for producing an antibody or antigen binding fragment thereof as defined in the first embodiment, or an antigen binding variant or derivative as defined in the second embodiment, wherein the process comprises culturing hybridoma cells as defined in the third embodiment, or a host cell as defined in the tenth embodiment, in a culture medium under suitable conditions to thereby produce the antibody or antigen binding fragment thereof, or the antigen binding variant or derivative.

The process may further comprise isolating the antibody or antigen binding fragment thereof, or the antigen binding variant or derivative, from the culture.

The antibody or antigen binding fragment thereof, or antigen binding variant or derivative, may each have binding specificity for an epitope present in glypican-1 heparan sulfate proteoglycan (GPC-1).

In a twelfth embodiment, the present invention provides a process for producing an antibody or antigen binding fragment thereof as defined in the first embodiment, or an antigen binding variant or derivative as defined in the second embodiment, wherein the process comprises culturing a cell culture as defined in the fourth or fifth embodiment under suitable conditions to thereby produce the antibody or antigen binding fragment thereof, or the antigen binding variant or derivative.

The process may further comprise isolating the antibody or antigen binding fragment thereof, or the antigen binding variant or derivative, from the culture.

The antibody or antigen binding fragment thereof, or antigen binding variant or derivative, may each have binding specificity for an epitope present in glypican-1 heparan sulfate proteoglycan (GPC-1).

In a thirteenth embodiment, the present invention provides an antibody or antigen binding fragment thereof, or an antigen binding variant or derivative, obtained or obtainable from a process as defined in the eleventh or twelfth embodiment.

The antibody or antigen binding fragment thereof, or antigen binding variant or derivative, may comprise a detectable label.

The detectable label may be any one or more of a fluorescent label, a radiolabel, biotin, or avidin.

In a fourteenth embodiment, the present invention provides a process for obtaining hybridoma cells as defined in the third embodiment from a mixed hybridoma population, the process comprising isolating at least a portion of the hybridoma cells from the mixed hybridoma population.

The isolating may comprise cloning individual hybridoma cells of the mixed hybridoma population, and determining that clonal offspring are capable of producing an antibody or antigen binding fragment thereof as defined in the first embodiment, or an antigen binding variant or derivative as defined in the second embodiment.

The mixed hybridoma population may be deposited at the American Tissue Type Culture Collection (ATCC) under accession number HB11785.

In a fifteenth embodiment, the present invention provides a kit comprising any one or more of an antibody or antigen binding fragment thereof, antigen binding variant or derivative, chimeric antibody, or hybridoma cells according to the present invention.

The hybridoma cells may be deposited at Cellbank Australia under accession number CBA20140026.

The kit may be a fragmented kit or a combined kit. The kit may further comprise one or more additional components selected from reagents for cell culture, reference samples, buffers, labels, and written instructions for performing an assay using components of the kit.

In a sixteenth embodiment, the present invention provides a composition comprising any one or more of an antibody or antigen binding fragment thereof, antigen binding variant or derivative, chimeric antibody, or hybridoma cells according to the present invention.

The composition may be a pharmaceutical composition. The pharmaceutical composition may further comprise a pharmaceutically acceptable diluent, excipient and/or carrier.

In a seventeenth embodiment, the present invention provides a method for detecting and/or quantifying the expression of GPC-1 in a subject, the method comprising (a) obtaining cells, a tissue sample, and/or a body fluid sample from the subject; (b) contacting the cells, tissue sample, and/or body fluid sample with an antibody, antibody variant, antibody fragment, antibody variant, antibody derivative, or chimeric antibody, according to the present invention, and (c) determining and/or quantifying binding of said antibody, antibody variant, antibody fragment, antibody derivative, or chimeric antibody to the cells, tissue sample, or body fluid sample of the subject.

The level of GPC-1 expression detected in the cells, tissue and/or body fluid sample obtained from the subject may be compared to a control cell sample or a sample population reference of GPC-1 expression levels. In some embodiments, a determination of increased GPC-1 expression in the subject compared to the control or reference may be diagnostic of a disease, or, an increased likelihood of developing a disease, in the subject. The disease may be prostate cancer.

The GPC-1 for detection may be present on the surface of the cells and/or expressed internally. The body fluid may be urine, blood or components thereof (for example, serum or plasma). The cells or tissue sample may be prostate cells or prostate tissue.

The antibody, antibody variant, antibody fragment, antibody derivative, or chimeric antibody, may be produced by hybridoma cells according to the present invention. The hybridoma cells may be deposited at Cellbank Australia under accession number CBA20140026.

In an eighteenth embodiment, the present invention provides a solution comprising a single species of monoclonal antibody, antibody variant, antibody fragment, antibody derivative, or chimeric antibody, capable of binding specifically to GPC-1 that may be applied to the cells, tissue sample, or body fluid sample that may potentially contain GPC-1. The single species may be produced by hybridoma cells deposited at Cellbank Australia under accession number CBA20140026.

In a nineteenth embodiment, the present invention provides a solution comprising multiple species of antibody, antibody variant, antibody fragment, antibody derivative, or chimeric antibody that may be applied to the cells, tissue sample, or body fluid sample that may potentially contain GPC-1, wherein at least one species of the multiple species in the solution is capable of binding specifically to GPC-1. The species capable of binding specifically to GPC-1 may be produced by hybridoma cells deposited at Cellbank Australia under accession number CBA20140026. The solution comprising multiple species may not comprise an antibody comprising a light chain variable region that comprises any one or more of:
 a complementarity determining region 1 (CDR1) comprising or consisting of an amino acid sequence defined by positions 48-58 of SEQ ID NO: 6;
 a complementarity determining region 2 (CDR2) comprising or consisting of an amino acid sequence defined by positions 74-80 of SEQ ID NO: 6;
 a complementarity determining region 3 (CDR3) comprising or consisting of an amino acid sequence defined by positions 113-121 of SEQ ID NO: 6.

The present invention also relates to the following embodiments:

Embodiment 1

An isolated antibody population comprising:
first antibodies and/or antigen binding fragments thereof, wherein the first antibodies comprise:
 (a) a heavy chain variable region comprising:
 a complementarity determining region 1 (CDR1) comprising or consisting of an amino acid sequence defined by positions 50-54 of SEQ ID NO: 3;
 a complementarity determining region 2 (CDR2) comprising or consisting of an amino acid sequence defined by positions 69-85 of SEQ ID NO: 3;
 a complementarity determining region 3 (CDR3) comprising or consisting of an amino acid sequence defined by positions 118-126 of SEQ ID NO: 3; and
 (b) a light chain variable region comprising:
 a complementarity determining region 1 (CDR1) comprising or consisting of an amino acid sequence defined by positions 44-54 of SEQ ID NO: 4;
 a complementarity determining region 2 (CDR2) comprising or consisting of an amino acid sequence defined by positions 70-76 of SEQ ID NO: 4;
 a complementarity determining region 3 (CDR3) comprising or consisting of an amino acid sequence defined by positions 109-117 of SEQ ID NO: 4;
and wherein the antibody population does not contain second antibodies, comprising a light chain variable region comprising:
 a complementarity determining region 1 (CDR1) comprising or consisting of an amino acid sequence defined by positions 48-58 of SEQ ID NO: 6;
 a complementarity determining region 2 (CDR2) comprising or consisting of an amino acid sequence defined by positions 74-80 of SEQ ID NO: 6;
 a complementarity determining region 3 (CDR3) comprising or consisting of an amino acid sequence defined by positions 113-121 of SEQ ID NO: 6.

Embodiment 2

The antibody population according to embodiment 1, wherein the antibody population does not contain antigen-binding fragments of said second antibodies.

Embodiment 3

The antibody population according to embodiment 1 or embodiment 2, wherein the first antibodies and/or antigen binding fragments thereof have binding specificity for an epitope present in glypican-1 heparan sulfate proteoglycan (GPC-1).

Embodiment 4

The antibody population according to any one of embodiments 1 to 3, wherein the first antibodies and/or antigen binding fragments thereof are IgG1 isotype.

Embodiment 5

The antibody population according to any one of embodiments 1 to 4, wherein the first antibodies and/or antigen binding fragments thereof are any one or more of monoclonal antibodies, humanised antibodies, chimeric antibodies, multimeric antibodies, and/or synthetic antibodies.

Embodiment 6

The antibody population according to any one of embodiments 1 to 5, wherein the antigen binding fragments are any one or more of single chain variable fragments (scFv), variable domain (Fv) fragments, fragment antigen binding (Fab) fragments, F(ab)2 fragments, peptides, or proteolytic fragments containing an epitope binding region.

Embodiment 7

The antibody population according to any one of embodiments 1 to 6, wherein the first antibodies and/or antigen binding fragments thereof further comprise:
 (a) one or more heavy chain variable region FR (framework regions) as defined by a sequence selected from any one or more of: residues 20-49 of SEQ ID NO: 3, residues 55-68 of SEQ ID NO: 3, residues 86-117 of SEQ ID NO: 3, residues 127-137 of SEQ ID NO: 3; and/or
 (b) one or more light chain variable region FR (framework regions) as defined by a sequence selected from any one or more of: residues 21-43 of SEQ ID NO: 4, residues 55-69 of SEQ ID NO: 4, residues 77-108 of SEQ ID NO: 4, residues 118-127 of SEQ ID NO: 4.

Embodiment 8

The antibody population according to any one of embodiments 1 to 7, wherein the first antibodies and/or antigen binding fragments thereof further comprise any one or more of:

(a) a heavy chain constant domain sequence as defined by positions 138-461 of SEQ ID NO: 3;
(b) a light chain constant domain sequence as defined by positions 128-234 of SEQ ID NO: 4;
(c) a hinge region.

Embodiment 9

The antibody population according to any one of embodiments 1 to 8 wherein the first antibodies comprise or consist of a heavy chain sequence as defined by positions 20-461 of SEQ ID NO: 3 and a light chain sequence as defined by positions 21-234 of SEQ ID NO: 4.

Embodiment 10

Hybridoma cells capable of producing the antibody population according to any one of embodiments 1 to 9.

Embodiment 11

A cell culture comprising a single species of hybridoma cells capable of producing an antibody population according to any one of embodiments 1 to 9, wherein the antibody population contains only one species of antibody and/or antigen binding fragments thereof.

Embodiment 12

The hybridoma cells according to embodiment 9, or the cell culture according to embodiment 10, wherein the hybridoma cells are deposited at Cellbank Australia under accession number CBA20140026.

Embodiment 13

A cell culture comprising multiple species of hybridoma cells, wherein:
(a) the cell culture comprises the hybridoma cells according to embodiment 10 or embodiment 12; and
(b) the cell culture does not comprise hybridoma cells that produce an antibody comprising a:
light chain variable region that comprises any one or more of:
  a complementarity determining region 1 (CDR1) comprising or consisting of an amino acid sequence defined by positions 48-58 of SEQ ID NO: 6;
  a complementarity determining region 2 (CDR2) comprising or consisting of an amino acid sequence defined by positions 74-80 of SEQ ID NO: 6;
  a complementarity determining region 3 (CDR3) comprising or consisting of an amino acid sequence defined by positions 113-121 of SEQ ID NO: 6.

Embodiment 14

The cell culture according to embodiment 13, wherein the cell culture does not comprise hybridoma cells that produce an antibody comprising one or more light chain variable region FR (framework regions) as defined by a sequence selected from any one or more of: residues 25-47 of SEQ ID NO: 6, residues 59-73 of SEQ ID NO: 6, residues 81-112 of SEQ ID NO: 6, residues 122-131 of SEQ ID NO: 6.

Embodiment 15

A composition comprising an antibody population according to any one of embodiments 1 to 9, wherein the antibody population contains only one species of antibody and/or antigen binding fragments thereof.

Embodiment 16

A composition comprising an antibody population according to any one of embodiments 1 to 9, wherein the antibody population contains multiple species of antibodies and/or antigen binding fragments thereof.

Embodiment 17

The composition according to embodiment 16, wherein the multiple species of antibodies and/or antigen binding fragments thereof each have binding specificity for an epitope present in glypican-1 heparan sulfate proteoglycan (GPC-1).

Embodiment 18

A nucleic acid molecule encoding at least one of the first antibodies or antigen binding fragments thereof according to any one of embodiments 1 to 9.

Embodiment 19

The nucleic acid molecule according to embodiment 18, wherein the nucleic acid molecule comprises or consists of a sequence as defined in SEQ ID NO: 1.

Embodiment 20

The nucleic acid molecule according to embodiment 18 or embodiment 19, wherein the nucleic acid molecule comprises or consists of a sequence as is defined in SEQ ID NO: 2.

Embodiment 21

A vector comprising the nucleic acid molecule according to any one of embodiments 18 to 20.

Embodiment 22

A host cell comprising the vector according to embodiment 21.

Embodiment 23

A process for producing antibodies or antigen-binding fragments thereof, wherein the process comprises culturing the hybridoma cells according to embodiment 10 or embodiment 12, or the host cell according to embodiment 22, in a culture medium under suitable conditions to thereby produce the antibody or antigen-binding fragment thereof.

Embodiment 24

A process for producing antibodies or antigen-binding fragments thereof, wherein the process comprises culturing the cell culture of any one of embodiments 11 to 14 under suitable conditions to thereby produce the antibodies or antigen-binding fragments thereof.

Embodiment 25

The process according to embodiment 23 or embodiment 24, further comprising isolating the antibodies or antigen-binding fragments thereof from the culture.

Embodiment 26

Antibodies or antigen binding fragments thereof obtained or obtainable from the process according to any one of embodiments 23 to 25.

Embodiment 27

A process for obtaining hybridoma cells according to embodiment 10 or embodiment 12 from a mixed hybridoma population, the process comprising isolating at least a portion of the hybridoma cells from the mixed hybridoma population.

Embodiment 28

The process according to embodiment 27, wherein the isolating comprises cloning individual hybridoma cells of the mixed hybridoma population, and determining that clonal offspring are capable of producing the antibody population according to any one of embodiments 1 to 9.

Embodiment 29

The process according to embodiment 27 or embodiment 28, wherein the mixed hybridoma population is deposited at the American Tissue Type Culture Collection (ATCC) under accession number HB11785.

Embodiment 30

The antibody population according to embodiment 5, wherein the first antibodies and/or antigen binding fragments thereof are chimeric.

Embodiment 31

The antibody population according to embodiment 5 or embodiment 30, wherein the first antibodies and/or antigen binding fragments thereof are chimeric antibodies comprising:

(a) a heavy chain constant region comprising or consisting of an amino acid sequence as defined in residues 138-467 of SEQ ID NO: 9; and (b) a light chain constant region comprising or consisting of an amino acid sequence as defined in residues of 128-234 SEQ ID NO: 10.

Embodiment 32

The antibody population according to any one of embodiments 1 to 9, wherein the first antibodies and/or fragments thereof comprise a detectable label.

Embodiment 33

The antibody population according to embodiments 32, wherein the detectable label is any one or more of a fluorescent label, a radiolabel, biotin, or avidin.

BRIEF DESCRIPTION OF THE DRAWINGS

Preferred embodiments of the present invention will now be described, by way of example only, with reference to the accompanying figures wherein:

FIG. 2 shows a comparison of MIL-38 antibody preparations sourced from in-house hybridoma stocks (AusMAb hybridoma cell clone 1) or cells re-cloned from the original HB11785 hybridoma stock from ATCC (AusMAb hybridoma lines 3, 4 and 5) with those of in-house MIL-38 antibody preparation 33A.

FIG. 3 shows a comparison of various MIL-38 antibody preparations generated and stored in-house (16A, 16B, 16C, 17B, 23A-1, 23A-2, 24A, 25A, 25B, 26B, 30A, 31A, 31B, 31C, 31D, 32B, 32C, 33A, 33B, 33C, 33D, 34A, 34B, 35A, 35C, 35D, 40A, 40B, AM-3, AM-4).

FIG. 4 shows results of MIL-38 antibody population analyses.

FIG. 5 shows images from immunofluorescence assays using various preparations of MIL-38 antibodies. Specifically.

FIG. 6 shows the results of comparative sandwich ELISAs performed using different antibody preparations as capture antibodies.

FIG. 8A-D show combined bright field and DAPI images of the stained cells. FIG. 8E-H show staining of DU-145 cells with MIL-38 prep 33A (8E, positive control), chimeric MIL-38 (8F), Cetuximab (8G, positive control for human IgG1k), and negative control (8H, no 1° antibody);

FIG. 9A shows reactivity of murine MIL-38 with DU-145 MPEK extract, C3 MPEK extract and NS0-produced recombinant GPC-1 antigen. FIG. 9B shows reactivity of chimeric MIL-38 with DU-145 MPEK extract, C3 MPEK extract and NS0-produced recombinant GPC-1 antigen. FIG. 9C shows reactivity of murine MIL-38 with DU-145 MPEK extract, C3 MPEK extract and NS0-produced recombinant GPC-1 antigen under equivalent conditions to FIG. 9B.

DEFINITIONS

Figure 1:
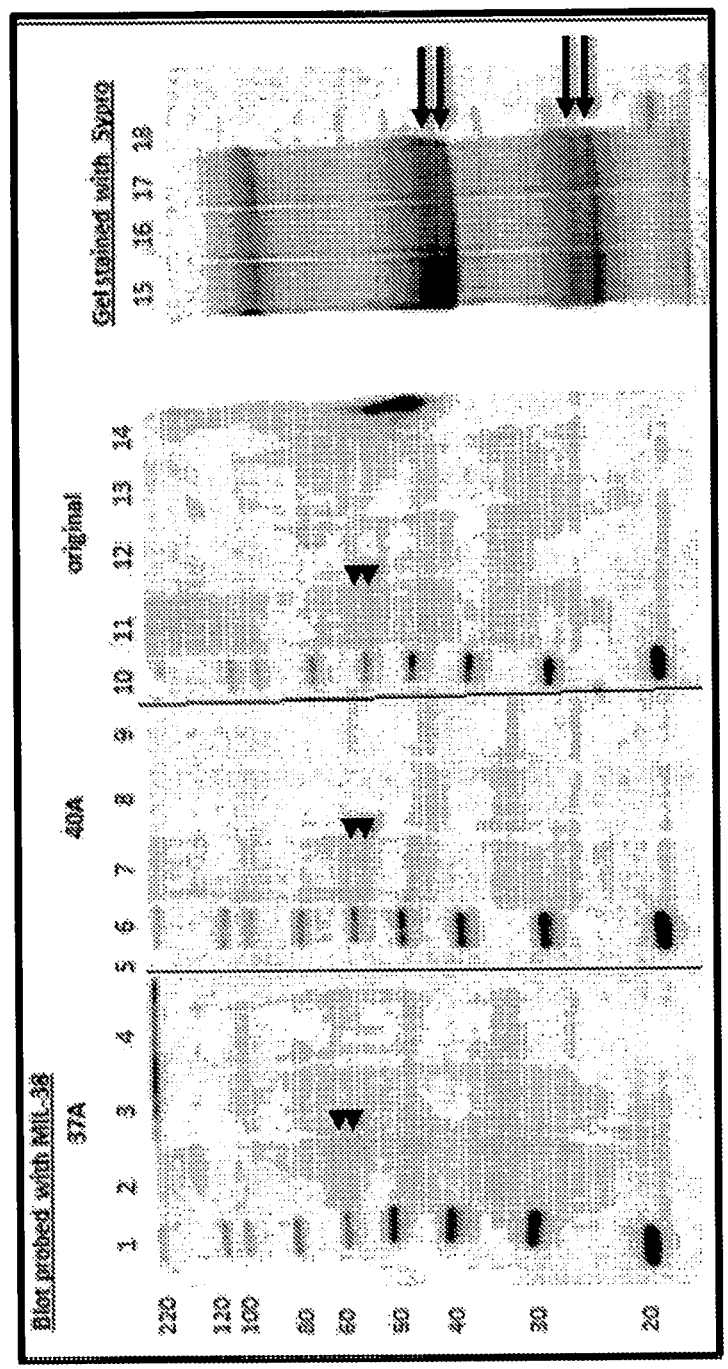
FIG. 1 shows the results of Western blot analyses using MIL-38 antibodies from various sources on extracts from DU-145, C3, and CA-HPV-10 cell lines. Arrowheads indicate equivalent reactivity of the different antibody preparations with the MIL-38 antigen. Arrows indicate the dual bands for the heavy chain and light chains in each of the three preps. Abbreviations: 37A=in-house MIL-38 antibody preparation; "original" (1-0)=MIL-38 antibody preparation from ATCC hybridoma cells (HB11785); 40A=MIL-38 antibody preparation from in-house hybridoma cells; Sypro=Sypro® Ruby Protein Gel Stain. Lanes: 1 (MW marker); 2 (DU145 MPEK 16/7/12); 3 (C3 MPEK 20/4/12); 4 (CA-HPV-10 MPEK 28/3/12); 5 (-); 6 (MW marker); 7 (DU145 MPEK 16/7/12); 8 (C3 MPEK 20/4/12); 9 (CA-HPV-10 MPEK 28/3/12); 10 (MW marker); 11 (DU145 MPEK 16/7/12); 12 (C3 MPEK 20/4/12); 13 (CA-HPV-10 MPEK 28/3/12); 14 (-); 15 (MIL-38 prep 1 "original"); 16 (MIL-38 prep 40A); 17 (MIL-38 prep 37A); 18 (MW marker)

As used in this application, the singular form "a", "an" and "the" include plural references unless the context clearly dictates otherwise. For example, the phrase "an antibody" also includes multiple antibodies.

As used herein, the term "comprising" means "including." Variations of the word "comprising", such as "comprise" and "comprises," have correspondingly varied meanings. Thus, for example, a sample "comprising" antibody A may consist exclusively of antibody A or may include one or more additional components (e.g. antibody B).

As used herein the term "multiple" means more than one. In certain specific aspects or embodiments, multiple may mean 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or more, and any integer derivable therein, and any range derivable therein.

As used herein, the terms "antibody" and "antibodies" include IgG (including IgG1, IgG2, IgG3, and IgG4), IgA (including IgA1 and IgA2), IgD, IgE, IgM, and IgY, whole antibodies, including single-chain whole antibodies, and antigen-binding fragments thereof. Antigen-binding antibody fragments include, but are not limited to, Fv, Fab, Fab' and F(ab')2, Fd, single-chain Fvs (scFv), single-chain antibodies, disulfide-linked Fvs (sdFv) and fragments comprising either a VL or VH domain. The antibodies may be from any animal origin or appropriate production host. Antigen-binding antibody fragments, including single-chain antibodies, may comprise the variable region/s alone or in combination with the entire or partial of the following: hinge region, CH1, CH2, and CH3 domains. Also included are any combinations of variable region/s and hinge region, CH1, CH2, and CH3 domains. Antibodies may be monoclonal, polyclonal, chimeric, multispecific, humanised, and human monoclonal and polyclonal antibodies which specifically bind the biological molecule. The antibody may be a bi-specific antibody, avibody, diabody, tribody, tetrabody, nanobody, single domain antibody, VHH domain, human antibody, fully humanized antibody, partially humanized antibody, anticalin, adnectin, or affibody.

As used herein the term "monoclonal antibody" refers to an antibody that recognises a single antigenic epitope, and that is obtained from a population of substantially homogeneous antibodies which bind specifically to the same antigenic epitope, and are identical with the potential exception of naturally occurring mutation/s that may be present in minor amounts.

As used herein, the term "humanised antibody" refers to forms of antibodies that contain sequences from human antibodies as well as non-human antibodies (e.g. murine antibodies). For example, a humanised antibody can comprise substantially all of at least one and typically two variable domains, in which all/substantially all of the hypervariable loops correspond to those of a non-human immunoglobulin and all/substantially all of the FR regions are from the human immunoglobulin sequence. The humanised antibody may optionally also comprise at least a portion of an immunoglobulin constant region (Fc) which may typically be that of a human immunoglobulin.

As used herein, the term "chimeric antibody" refers to an antibody which exhibits a desired biological activity, and in which a portion of the light chain and/or heavy chain is identical to or homologous with corresponding sequences in antibodies derived from a given/specific species, while the remaining chain/s is/are identical to or homologous with corresponding sequences in antibodies derived from another different species. For example, a chimeric antibody may comprise variable regions that are derived from a first species and comprise constant regions that are derived from a second species. Chimeric antibodies can be constructed for example by genetic engineering from immunoglobulin gene segments belonging to different species.

As used herein, the term "hybridoma" refers to a cell produced by the fusion of an immortal cell (e.g. a multiple myeloma cell) and an antibody-producing cell (e.g. a B lymphocyte), which is capable of producing monoclonal antibodies of a single binding specificity.

As used herein, the terms "binding specifically" and "specifically binding" in reference to an antibody, antibody variant, antibody derivative, antigen binding fragment, and the like refers to its capacity to bind to a given target molecule preferentially over other non-target molecules. For example, if the antibody, antibody variant, antibody derivative, or antigen binding fragment ("molecule A") is capable of "binding specifically" or "specifically binding" to a given target molecule ("molecule B"), molecule A has the capacity to discriminate between molecule B and any other number of potential alternative binding partners. Accordingly, when exposed to a plurality of different but equally accessible molecules as potential binding partners, molecule A will selectively bind to molecule B and other alternative potential binding partners will remain substantially unbound by molecule A. In general, molecule A will preferentially bind to molecule B at least 10-fold, preferably 50-fold, more preferably 100-fold, and most preferably greater than 100-fold more frequently than other potential binding partners. Molecule A may be capable of binding to molecules that are not molecule B at a weak, yet detectable level. This is commonly known as background binding and is readily discernible from molecule B-specific binding, for example, by use of an appropriate control.

As used herein, the term "subject" includes any animal of economic, social or research importance including bovine, equine, ovine, primate, avian and rodent species. Hence, a "subject" may be a mammal such as, for example, a human or a non-human mammal.

As used herein, the term "isolated" in reference to a biological molecule (e.g. an antibody) is a biological molecule that is free from at least some of the components with which it naturally occurs.

As used herein, the terms "protein" and "polypeptide" each refer to a polymer made up of amino acids linked together by peptide bonds and are used interchangeably. For the purposes of the present invention a "polypeptide" may constitute a full length protein or a portion of a full length protein.

As used herein, the term "polynucleotide" refers to a single- or double-stranded polymer of deoxyribonucleotide bases, ribonucleotide bases, known analogues or natural nucleotides, or mixtures thereof.

As used herein, the term "kit" refers to any delivery system for delivering materials. Such delivery systems include systems that allow for the storage, transport, or delivery of reaction reagents (for example labels, reference samples, supporting material, etc. in the appropriate containers) and/or supporting materials (for example, buffers, written instructions for performing an assay etc.) from one location to another. For example, kits may include one or more enclosures, such as boxes, containing the relevant reaction reagents and/or supporting materials. The term "kit" includes both fragmented and combined kits. A "fragmented kit" refers to a delivery system comprising two or more separate containers that each contain a sub portion of the total kit components. The containers may be delivered to the intended recipient together or separately. Any delivery system comprising two or more separate containers that each contain a sub portion of the total kit components are included within the meaning of the term "fragmented kit". A "combined kit" refers to a delivery system containing all of the components of a reaction assay in a single container (e.g. in a single box housing each of the desired components).

It will be understood that use of the term "between" herein when referring to a range of numerical values encompasses the numerical values at each endpoint of the range. For example, a polypeptide of between 10 residues and 20 residues in length is inclusive of a polypeptide of 10 residues in length and a polypeptide of 20 residues in length.

Any description of prior art documents herein, or statements herein derived from or based on those documents, is not an admission that the documents or derived statements are part of the common general knowledge of the relevant art. For the purposes of description all documents referred to herein are hereby incorporated by reference in their entirety unless otherwise stated.

DETAILED DESCRIPTION

A need continues to exist for more effective methods and agents to diagnose and/or treat various forms of cancer such as prostate cancer. Antibodies are useful diagnostic and therapeutic agents for cancer, having become a successful and important tool for diagnosing and treating patients with haematological malignancies and solid tumours. The identification of new relevant antibodies targeting tumour-specific antigens offers one potential means of improving diagnostic and/or therapeutic outcomes for cancer patients. Another means by which these outcomes can be enhanced is through the improvement of existing antibody-based diagnostics and/or therapies.

The "BLCA-38 antibody" has been the subject of previous research in the diagnosis and/or treatment of cancer, including bladder and prostate cancer. In the prior art, the "BLCA-38 antibody" is referred to persistently as a murine monoclonal antibody targeting an unknown antigen of approximately 30 kDa in size[1-5]. The present inventors have surprisingly identified that the BLCA-38 antibody as disclosed and used in the prior art is not a single monoclonal antibody population as previously indicated, but instead a combination of two distinct monoclonal antibodies in a mixed population. This stems from the present inventor's determination that the hybridoma used to generate the BLCA-38 antibody, a representative sample of which was deposited at the American Tissue Type Culture Collection under accession number HB11785, is a biclonal (rather than monoclonal) population of hybridoma cells, which produces a mixture of two discrete antibody species. Only one of these antibody species is capable of binding to the relevant antigen on prostate cancer cells, whilst the second species cannot. Moreover, the antigen bound by this antibody is significantly larger than the 30 kDa indicated in the prior art[3-4].

These unexpected findings have facilitated the generation of a monoclonal hybridoma capable of producing a single population of antibodies with binding specificity only for the target antigen. Apart from circumventing the unnecessary production and application of an ineffectual antibody (i.e. the second monoclonal antibody population present in the mixed population of the prior art), using the monoclonal hybridoma/single antibody according to the present invention provides a stronger signal compared to the mixed population of the prior art when equivalent amounts of antibody are utilised.

Accordingly, certain embodiments of the present invention relate to the provision of a monoclonal antibody population derived from clonal hybridoma cells, each member of the antibody population being capable of binding specifically to an antigen present on certain cancer cells (e.g. bladder and prostate cancer cells). The present invention also provides antigen binding fragments of these antibodies, as well as derivatives and variants of the antibodies which maintain the same binding specificity.

Also provided are hybridomas capable of producing antibodies of the present invention. One example of such a hybridoma was deposited under the terms of the Budapest Treaty at Cellbank Australia at 214 Hawkesbury Road, Westmead, NSW 2145, Australia on 22 Aug. 2014 under accession number CBA20140026.

Further provided are methods for producing and/or isolating antibodies of the present invention, and methods of detection/diagnosis that utilise the antibodies.

Monoclonal Antibodies

The present invention provides monoclonal antibodies, derivatives of such antibodies, and antigen binding fragments thereof.

The monoclonal antibodies, variants, derivatives, and antigen binding fragments are capable of binding specifically to an antigenic epitope present in glypican-1 heparan sulfate proteoglycan (GPC-1). The GPC-1 protein may be a human glypican-1 protein (e.g. as defined by a sequence set forth in any one of: NCBI reference sequence accession no. NP 002072.2, GenBank accession no. AAH51279.1, GenBank accession no. AAA98132.1, GenBank accession no. EAW71184.1, or UniProtKB/Swiss-Prot accession no. P35052.2). In some embodiments the GPC-1 protein may not include a signal peptide and/or a propeptide. Additionally or alternatively, the monoclonal antibodies, derivatives, and antigen binding fragments may be capable of binding specifically to an antigenic epitope present in a GPC-1 variant (e.g. a GPC-1 isoform, splice variant, or allotype).

By way of non-limiting example, the monoclonal antibodies, variants, derivatives, and antigen binding fragments may comprise a heavy chain and/or a light chain, combinations thereof, or component/s thereof.

The heavy chain or component/s thereof may comprise a heavy chain variable region comprising one, two, or three complementarity determining regions (CDR1, CDR2, and/or CDR3), also known in the art as heavy chain hypervariable (HV) regions. The heavy chain CDR1 may comprise or consist of an amino acid sequence as defined by residues 50-54 of SEQ ID NO: 3. The heavy chain CDR2 may comprise or consist of an amino acid sequence as defined by residues 69-85 of SEQ ID NO: 3. The heavy chain CDR3 may comprise or consist of an amino acid sequence as defined by residues 118-126 of SEQ ID NO: 3.

Additionally or alternatively, the heavy chain variable region may comprise one, two, three, or four framework regions (FR1, FR2, FR3, and/or FR4). The heavy chain FR1 may comprise or consist of an amino acid sequence as defined by residues 20-49 of SEQ ID NO: 3. The heavy chain FR2 may comprise or consist of an amino acid sequence as defined by residues 55-68 of SEQ ID NO: 3. The heavy chain FR3 may comprise or consist of an amino acid sequence as defined by residues 86-117 of SEQ ID NO: 3. The heavy chain FR4 may comprise or consist of an amino acid sequence as defined by residues 127-137 of SEQ ID NO: 3.

Additionally or alternatively, the heavy chain variable region may comprise a leader sequence. The heavy chain leader sequence may comprise or consist of an amino acid sequence as defined by residues 1-19 of SEQ ID NO: 3. The skilled person will recognise that the leader sequence is a signal sequence which facilitates the transport of a newly synthesised heavy chain into the endoplasmic reticulum, and is generally not present in the heavy chain of the final assembled form of the monoclonal antibody.

Additionally or alternatively, the light chain or component/s thereof may comprise a light chain variable region comprising one, two, or three complementarity determining regions (CDR1, CDR2, CDR3) also known in the art as light chain hypervariable (HV) regions. The light chain CDR1 may comprise or consist of an amino acid sequence as defined by residues 44-54 of SEQ ID NO: 4. The light chain CDR2 may comprise or consist of an amino acid sequence as defined by residues 70-76 of SEQ ID NO: 4. The light chain CDR3 may comprise or consist of an amino acid sequence as defined by residues 109-117 of SEQ ID NO: 4.

Additionally or alternatively, the light chain variable region may comprise one, two, three, or four framework regions (FR1, FR2, FR3, FR4). The light chain FR1 may comprise or consist of an amino acid sequence as defined by residues 21-43 of SEQ ID NO: 4. The light chain FR2 may comprise or consist of an amino acid sequence as defined by residues 55-69 of SEQ ID NO: 4. The light chain FR3 may comprise or consist of an amino acid sequence as defined by residues 77-108 of SEQ ID NO: 4. The light chain FR4 may comprise or consist of an amino acid sequence as defined by residues 118-127 of SEQ ID NO: 4.

Additionally or alternatively, the light chain variable region may comprise a leader sequence. The light chain leader sequence may comprise or consist of an amino acid sequence as defined by residues 1-20 of SEQ ID NO: 4. The skilled person will recognise that the leader sequence is a signal sequence which facilitates transport of a newly synthesised light chain into the endoplasmic reticulum, and is generally not present in the light chain of the final assembled form of the monoclonal antibody.

Additionally or alternatively, the heavy chain may comprise one, two, or three heavy chain constant regions. The heavy chain constant region may comprise or consist of an amino acid sequence as defined by residues 138-461 of SEQ ID NO: 3.

Additionally or alternatively, the light chain may comprise a light chain constant region. The light chain constant region may comprise or consist of an amino acid sequence as defined by residues 128-234 of SEQ ID NO: 4.

In some embodiments, monoclonal antibodies, variants, derivatives, and antigen binding fragments according to the present invention may comprise a heavy chain variable region which comprises or consists of an amino acid sequence as defined by residues 20-137 of SEQ ID NO: 3. The monoclonal antibodies, variants, derivatives, and antigen binding fragments may comprise one or two of the heavy chain variable regions.

In some embodiments, monoclonal antibodies, variants, derivatives, and antigen binding fragments according to the present invention may comprise a light chain variable region which comprises or consists of an amino acid sequence as defined by residues 21-127 of SEQ ID NO: 4. The monoclonal antibodies, variants, derivatives, and antigen binding fragments may comprise one or two of the light chain variable regions.

In some embodiments, monoclonal antibodies, variants, derivatives, and antigen binding fragments according to the present invention may comprise a heavy chain variable region which comprises or consists of residues 20-137 of SEQ ID NO: 3, and a light chain variable region which comprises or consists of residues 21-127 of SEQ ID NO: 4. The monoclonal antibodies, variants, derivatives, and antigen binding fragments may comprise a combination of two of the heavy chain variable regions and two of the light chain variable regions.

In some embodiments, monoclonal antibodies, variants, derivatives, and antigen binding fragments according to the present invention may comprise a heavy chain comprising or consisting of an amino acid sequence as defined by residues 20-461 of SEQ ID NO: 3. The monoclonal antibodies, variants, derivatives, and antigen binding fragments may comprise one or two of the heavy chains.

In some embodiments, monoclonal antibodies, variants, derivatives, and antigen binding fragments according to the present invention may comprise a light chain comprising or consisting of an amino acid sequence as defined by residues 21-234 of SEQ ID NO: 4. The monoclonal antibodies, variants, derivatives, and antigen binding fragments may comprise one or two of the light chains.

In some embodiments, monoclonal antibodies, variants, derivatives, and antigen binding fragments according to the present invention may comprise a heavy chain comprising or consisting of an amino acid sequence as defined by residues 20-461 of SEQ ID NO: 3, and a light chain comprising or consisting of an amino acid sequence as defined by residues 21-234 of SEQ ID NO: 4. The monoclonal antibodies, variants, derivatives, and antigen binding fragments may comprise or consist of a combination of two of the heavy chains and two of the light chains.

Monoclonal antibodies, variants and derivatives of such antibodies, and antigen binding fragments thereof according to the present invention are not restricted to any particular isotype, and thus may be IgA (IgA1 or IgA2), IgD, IgE, IgG (IgG1, IgG2, IgG3, IgG4), or IgM isotype. In some embodiments, they are IgG1 isotype.

Included within the scope of the present invention are monoclonal antibodies produced by hybridoma cells submitted under the terms of the Budapest Treaty at Cellbank Australia at 214 Hawkesbury Road, Westmead NSW 2145, Australia on 22 Aug. 2014 under accession number CBA20140026. The hybridoma is a clonal population that produces a single antibody species having binding specific for an epitope existing in glypican-1 heparan sulfate proteoglycan (GPC-1).

Antibody Fragments, Derivatives and Variants

Included within the scope of the present invention are "fragments" of the antibodies described herein. In general, the fragments are "antigen binding fragments" in the sense that they are capable of specifically binding to same antigen/epitope (e.g. GPC-1) as the parent antibody from which they are derived or upon which they are based. Typically, an antigen binding fragment retains at least 10% of the antigen/epitope binding capacity of the parent antibody, or, at least 25%, 50%, 60%, 70%, 80%, 90%, 95%, 99% or 100% (or more) of the antigen/epitope binding capacity of the parent antibody. It is also contemplated that an antigen binding fragment of an antibody described herein may include conservative amino acid substitutions that do not substantially alter its antigen/epitope binding specificity/capacity (e.g. at least 70%, 80%, 90%, 95%, 99% or 100% (or more) of its antigen/epitope binding specificity/capacity may be retained).

Non-limiting examples of antigen binding fragments include portions of a full length antibody, peptides and derivatives thereof including, for example, Fab, Fab', F(ab)$_2$, F(ab')$_2$, F(ab)$_3$, Fv, single-chain Fv (scFv), dsFv, Fd fragments, dAB fragments Fse, VH, VL, VhH, and V-NAR domains, paratopes, CDR regions, single-chain antibody molecules (e.g. sc-Fv), minibodies, diabodies, triabodies, tetrabodies, kappa bodies, linear antibodies, multispecific antibodies, domain antibodies formed from antibody fragments, multispecific antibody fragments formed from antibody fragments, and any portion or peptide sequence of the antibody that is capable of specifically binding to the relevant antigen/epitope (e.g. GPC-1).

Also included within the scope of the present invention are "derivatives" of the antibodies described herein. A "derivative" of an antibody of the present invention refers to an antibody described herein that is modified to incorporate additional components or have existing component/s altered, but is still capable of specifically binding to the same antigen/epitope (e.g. GPC-1) as the parent antibody from which it is derived. Typically, an antibody derivative as contemplated herein retains at least 10% of the antigen/epitope binding capacity of the parent antibody, or, at least 25%, 50%, 60%, 70%, 80%, 90%, 95%, 99% or 100% (or more) of the antigen/epitope binding capacity of the parent antibody.

Non-limiting examples of modifications suitable to form antibody derivatives include amidation, glycosylation, phosphorylation, pegylation, linkage to a cellular ligand or other protein, derivatisation by known protecting/blocking groups, acetylation, and the like. Additionally or alternatively, the derivative may contain one or more non-classical amino acids.

The antibody derivatives may include labelled antibodies such as, for example, monoclonal antibodies labelled with radioactive iodine, indium, sulphur, carbon, tritium or the like; monoclonal antibodies conjugated with avidin or biotin, monoclonal antibodies conjugated with enzymes (e.g. horseradish, glucose 6-phosphate dehydrogenase glucose oxidase, beta-D-galactosidase, alkaline phosphatase, glucoamylase, acetylcholine esterase, carboxylic acid anhydrase, malate dehydrogenase, lysozyme, or peroxidase), and monoclonal antibodies conjugated with chemoluminescent agents (e.g. acridine esters), bioluminescent agents (e.g. luciferase), or fluorescent agents (e.g. phycobiliproteins). Further examples of antibody derivatives include bifunctional antibodies, such as bispecific antibodies generated by combining parts of two separate antibodies that recognize two different antigenic groups (e.g. by recombinant techniques or crosslinking).

The antibody derivatives may be formed from covalent modification of the antibodies described herein, for example, by reacting targeted amino acid residues of the antibody with an agent capable of reacting with selected side chains or terminal residues. For example, derivatisation with bifunctional agents is a useful means for cross-linking an antibody or fragment thereof to macromolecular carriers such as water-insoluble support matrices. Antibody derivatives as contemplated herein may have an agent attached to a base antibody or a fragment thereof capable of increasing its half-life in vivo (e.g. extending the length of time before clearance from the blood stream). A non-limiting example of such a technique includes addition of PEG moieties.

In certain embodiments, the antibody derivative may be a multimer, such as, for example, a dimer, comprising one or more monomers, where each monomer includes (i) an antigen-binding region of an anti-GPC-1 antibody as described herein, or a polypeptide region derived therefrom (such as, for example, by conservative substitution of one or more amino acid/s), and (ii) a multimerising (e.g. dimerising) polypeptide region, such that the antibody derivative forms multimers (e.g. homodimers) that specifically bind to GPC-1. For example, an antigen binding region of an anti-GPC-1 antibody as described herein, or a polypeptide region derived therefrom, may be recombinantly or chemically fused with a heterologous protein, wherein the heterologous protein comprises a dimerisation or multimerisation domain. The derivative may be subjected to conditions allowing formation of a homodimer or heterodimer. The heterodimer may comprise identical dimerisation domains but different anti-GPC-1 antigen-binding regions, identical anti-GPC-1 antigen-binding regions but different dimerisation domains, or different anti-GPC-1 antigen-binding regions and different dimerisation domains. Suitable dimerisation domains include those that originate from transcription factors (e.g. a basic region leucine zipper), a basic-region helix-loop-helix protein, and an immunoglobulin constant region (e.g. a heavy chain constant region or a domain thereof such as a CH1 domain, a CH2 domain, or a CH3 domain).

In other embodiments, the antibody derivative may be an anti-GPC1 antibody as described herein conjugated to a second antibody (an "antibody heteroconjugate").

Also contemplated herein are humanised derivatives of the antibodies described herein. A "humanised" antibody as contemplated herein is a human/non-human chimeric antibody that contains a minimal sequence derived from non-human immunoglobulin. For example, a humanised antibody may be a human immunoglobulin (recipient antibody) in which residues from CDR region/s of the recipient are replaced by residues from a CDR region of a non-human species (donor antibody) (e.g. a mouse, rat, rabbit, or non-human primate having the desired specificity and affinity for a GPC-1 antigen/epitope). Framework region (FR) residues of the human immunoglobulin may also (optionally) be replaced by corresponding non-human residues, and in some cases humanised antibodies may comprise residues not present in the recipient antibody or in the donor antibody to enhance antibody performance.

Further contemplated herein are "chimeric" antibody derivatives in which a portion of the heavy and/or light chain is identical with or homologous to corresponding sequences of an antibody described herein derived from a particular species or belonging to a particular antibody class or subclass, while the remainder of the chain/s is/are identical with or homologous to corresponding sequences in antibodies derived from another different species or belonging to another different antibody class or subclass. For example, a chimeric antibody as contemplated herein may comprise variable regions derived from an anti-GPC-1 monoclonal antibody as described herein, and constant regions derived from a second species. Chimeric antibodies may be generated, for example, by genetic engineering of immunoglobulin gene segments belonging to different species.

By way of non-limiting example only, a chimeric antibody according to the present invention may comprise a chimeric Mouse Human CH1-CH3 Chain Sequence Mouse VH-Human CH1-CH3 Chain (heavy chain) and/or a Mouse Human Kappa Chain Sequence Mouse VK-Human CK sequence MIL-38 Mouse VK (light chain). The heavy chain of the chimeric antibody may comprise or consist of an amino acid sequence as set out in residues 20-467 of SEQ ID NO: 9. The light chain of the chimeric antibody may comprise or consist of an amino acid sequence as set out in residues 21-234 of SEQ ID NO: 10. The heavy chain variable region may comprise: a complementarity determining region 1 (CDR1) comprising or consisting of an amino acid sequence defined by positions 50-54 of SEQ ID NO: 9; and/or a complementarity determining region 2 (CDR2) comprising or consisting of an amino acid sequence defined by positions 69-85 of SEQ ID NO: 9; and/or a complementarity determining region 3 (CDR3) comprising or consisting of an amino acid sequence defined by positions 118-126 of SEQ ID NO: 9. Additionally or alternatively, the light chain variable region may comprise: a complementarity determining region 1 (CDR1) comprising or consisting of an amino acid sequence defined by positions 44-54 of SEQ ID NO: 10; and/or a complementarity determining region 2 (CDR2) comprising or consisting of an amino acid sequence defined by positions 70-76 of SEQ ID NO: 10; and/or a complementarity determining region 3 (CDR3) comprising or consisting of an amino acid sequence defined by positions 109-117 of SEQ ID NO: 10. A chimeric antibody according to the present invention may be a "variant" of this chimeric antibody.

Included within the scope of the present invention are "variants" of the antibodies described herein. A "variant" antibody refers to an antibody which differs in amino acid sequence from a "parent" anti-GPC-1 antibody amino acid sequence by virtue of addition, deletion, and/or substitution of one or more amino acid residue/s in the parent antibody sequence. For example, the variant antibody may comprise one or more amino acid substitution/s in one or more CDR and/or framework region/s of the parent antibody (e.g. between 1 and 10, between 2 and 5, or 1, 2, 3, 4, or 5 substitutions in one or more heavy and/or light chain CDR and/or framework regions of the parent antibody). The antibody variant may comprise a heavy chain variable domain sequence and/or a light chain variable domain sequence amino acid sequence having at least 50%, at least 60%, at least 70%, at least 80%, at least 85%, at least 90%, at least 95%, or at least 98% amino acid sequence homology (i.e. sequence identity) with the corresponding variable domain of the parent antibody.

Sequence homology or identity between two sequences is defined herein as the percentage of amino acid residues in the candidate sequence that are identical with the parent antibody residues, after aligning the sequences and introducing gaps, if necessary, to achieve the maximum percent sequence identity. If the two sequences which are to be compared with each other differ in length, sequence identity relates to the percentage of amino acid residues of the shorter sequence which are identical with the amino acid residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711) and/or the program "fasta20u66" (version 2.0u66, September 1998 by William R. Pearson and the University of Virginia; see also W. R. Pearson (1990), Methods in Enzymology 183, 63-98).

In some embodiments, a variant antibody as described herein may differ from a parent antibody by way of conservative amino acid change/s in the sequence of the variable antibody. A "conservative change" refers to an alteration that is substantially antigenically or conformationally neutral, producing minimal changes in the tertiary structure of the variant antibody, or producing minimal changes in the antigenic determinants of the variant antibody, as compared to the parent antibody, and one which does not render the derivative incapable of binding to the same epitope in GPC-1 as the parent antibody. Non-limiting examples of conservative amino acid changes include substitution of hydrophobic amino acids and substitution of physiochemically similar amino acids. Persons of ordinary skill in the art can routinely and without difficulty assess whether a given amino acid substitution can be made while maintaining conformational and antigenic neutrality (see, for example, Berzofsky, (1985) Science 229:932-940; Bowie et al. (1990) Science 247:1306-1310). Alterations in protein conformation may be achieved using well-known assays including, but not limited to, microcomplement fixation methods (see Wasserman et al. (1961) J. Immunol. 87:290-295; Levine et al. (1967) Meth. Enzymol. 11:928-936) and through binding studies using conformation-dependent monoclonal antibodies (see Lewis et al. (1983) Biochem. 22:948-954). The conservative amino acid change/s may occur in one or more CDR and/or framework region/s of the parent antibody (e.g.

between 1 and 10, between 2 and 5, or 1, 2, 3, 4, or 5 conservative substitutions in one or more CDR and/or framework regions of the parent antibody).

In general, humanised, chimeric, derivative, fragment and variant antibodies as contemplated herein are still capable of specifically binding to same antigen/epitope (e.g. GPC-1) as the parent antibody from which they derive or which they contain component/s of. Typically, they may retain at least 10% of the antigen/epitope binding capacity of the parent antibody, or, at least 25%, 50%, 60%, 70%, 80%, 90%, 95%, 99% or 100% (or more) of the antigen/epitope binding capacity of the parent antibody. For example, they may have a stronger binding affinity and/or binding specificity compared to the parent antibody.

The capacity of an antibody fragment, derivative, or variant to bind specifically to an antigen/epitope that is targeted by the parent antibody (i.e. a GPC-1 antigen/epitope) can be tested using known methods in the art including, for example, competitive and non-competitive assay systems using techniques such as Western blots, radioimmunoassays, enzyme linked immunosorbent assay (ELISA), immunoprecipitation assays, "sandwich" immunoassays, immunodiffusion assays, precipitin reactions, protein A immunoassays, fluorescent immunoassays, gel diffusion precipitin reactions, complement-fixation assays, immunoradiometric assays, agglutination assays, and the like (see, for example, Ausubel et al., eds., Short Protocols in Molecular Biology (John Wiley & Sons, Inc., New York, 4th ed. 1999); Harlow & Lane, Using Antibodies: A Laboratory Manual (Cold Spring Harbor Laboratory Press, Cold Spring Harbor, N.Y., 1999)).

Specifically included within the scope of the present invention are variants of any antibody or antigen binding fragment thereof described herein including, but not limited to, antibodies (including chimeric antibodies) and antigen binding fragments defined by specific sequences herein, and antibodies produced by hybridomas described herein including the hybridoma submitted under the terms of the Budapest Treaty at Cellbank Australia at 214 Hawkesbury Road, Westmead NSW 2145, Australia on 22 Aug. 2014 under accession number CBA20140026.

Hybridomas

The present invention provides hybridoma cells capable of producing monoclonal antibodies, derivatives and variants of such antibodies, and antigen binding fragments thereof.

In some embodiments, the hybridomas may produce monoclonal antibodies and/or antigen binding fragments thereof as set out in the section above entitled "Monoclonal antibodies".

In some embodiments, the hybridomas may produce fragments, derivatives and/or variants of the monoclonal antibodies described herein as set out in the section above entitled "Antibody fragments, derivatives and variants".

Techniques for the production of hybridoma cells capable of producing monoclonal antibodies are well known in the art. Non-limiting examples include the hybridoma method (see Kohler and Milstein, (1975) Nature, 256:495-497; Coligan et al. section 2.5.1-2.6.7 in Methods In Molecular Biology (Humana Press 1992); and Harlow and Lane Antibodies: A Laboratory Manual, page 726 (Cold Spring Harbor Pub. 1988)), the EBV-hybridoma method for producing human monoclonal antibodies (see Cole, et al. 1985, in Monoclonal Antibodies and Cancer Therapy, Alan R. Liss, Inc., pp. 77-96), the human B-cell hybridoma technique (see Kozbor et al. 1983, Immunology Today 4:72), and the trioma technique.

In brief, monoclonal antibodies of the present invention can be prepared by administering the immunogen (antigen) of interest (i.e. GPC-1), for example, by intraperitoneal injection, to inbred or wild type mice (e.g. BALB/c or C57BL/6 mice), rabbits, rats, or other animal species, or transgenic mice capable of producing native or human antibodies. To induce an immune response, the immunogen may, for example, be mixed with an adjuvant, administered alone, expressed by a vector, administered as DNA, or administered as a fusion protein. The animal may be boosted, for example, at least twice, and spleen cells may then be harvested from the immunised animal. Hybridomas can be generated by fusing sensitised spleen cells with a myeloma cell line (e.g. murine SP2/O myeloma cells using, for example, the methodology set out in Kohler and Milstein and Harlow and Lane).

A GPC-1 antigenic construct according to the present invention (e.g. a vaccine composition comprising the GPC-1 antigenic construct in a pharmaceutically acceptable form) may be administered to an appropriate animal in repeat dosages (e.g. between 1-15 doses, between 2-10 doses, between 3-7 doses, between 4-6 doses), for an appropriate time interval (e.g. between 1-10 weeks, between 1-6 weeks, between 1-4 weeks, or between 2-3 weeks). The immune response of the animal may be monitored by taking sera samples at a suitable time after boosting (e.g. between 3-10 days after boosting, between 4-8 days after boosting, between 5-6 days after boosting), and then determining the immunogenicity of the antigenic construct using known techniques (e.g. by ELISA). Immunisation in this manner may lead to an immune response in the animals. Animals with therapeutic titres are generally those providing a positive result by ELISA in an appropriate dilution (e.g. between 1:4000 and 1:6000, between 1:4500 and 1:5500, or 1:5000). Those with therapeutic titres can be selected for fusion of their antibody-producing cells (B-lymphocytes) with a continuously reproducing/immortal cell line (e.g. a myeloma cell line). The cells may be induced to fuse using an appropriate agent such as polyethylene glycol. The resulting hybrid cells may then be cloned in a conventional manner (e.g. using limiting dilution) and the clones generated tested for the ability to produce the desired anti-GPC-1 monoclonal antibodies in culture. Hybridomas may be chemically selected by plating the cells in a selection medium containing hypoxanthine, aminopterin and thymidine (HAT). Hybridomas may be screened for the ability to produce monoclonal antibodies and positive hybridomas can then be cloned, expanded and stored.

In preferred embodiments of the present invention, the hybridoma is a monoclonal cell population capable of producing a single antibody species capable of binding specifically to GPC-1. Non-limiting examples of such monoclonal antibodies are set out in the sections above entitled "Monoclonal antibodies" and "Antibody fragments, derivatives and variants".

In some embodiments, a hybridoma according to the present invention may be the hybridoma submitted under the terms of the Budapest Treaty at Cellbank Australia at 214 Hawkesbury Road Westmead NSW 2145 Australia on 22 Aug. 2014 under accession number CBA20140026. Methods for the culture and propagation of these hybridoma cells to produce monoclonal antibodies according to the present invention are well known to those of ordinary skill in the field.

Also contemplated herein are cell cultures comprising hybridoma cells of the present invention.

In some embodiments, the cell cultures comprise a single (monoclonal) species of hybridoma cells capable of producing a single species of antibody or antigen binding fragment thereof that binds specifically to GPC-1. Non-limiting examples of such monoclonal antibodies are set out in the sections above entitled "Monoclonal antibodies" and "Antibody fragments, derivatives and variants". The single (monoclonal) species of hybridoma cells may be deposited under the terms of the Budapest Treaty at Cellbank Australia under accession number CBA20140026.

In some embodiments, the cell cultures comprise multiple species of hybridoma cells (i.e. mixed hybridoma cell populations). The mixed population of hybridoma cells may comprise a single (monoclonal) species of hybridoma cells capable of producing a single species of antibody that binds specifically to GPC-1. Non-limiting examples of such monoclonal antibodies are set out in the sections above entitled "Monoclonal antibodies" and "Antibody fragments, derivatives and variants". The single (monoclonal) species of hybridoma cells may be deposited under the terms of the Budapest Treaty at Cellbank Australia under accession number CBA20140026. The mixed population of hybridoma cells may not comprise hybridoma cells deposited at ATCC under accession number HB11785 and/or hybridoma cells capable of producing an antibody comprising;

a light chain variable region that comprises any one or more of:
   a complementarity determining region 1 (CDR1) comprising or consisting of an amino acid sequence defined by positions 48-58 of SEQ ID NO: 6;
   a complementarity determining region 2 (CDR2) comprising or consisting of an amino acid sequence defined by positions 74-80 of SEQ ID NO: 6;
   a complementarity determining region 3 (CDR3) comprising or consisting of an amino acid sequence defined by positions 113-121 of SEQ ID NO: 6;
   and/or
   one or more light chain variable region FR (framework regions) as defined by a sequence selected from any one or more of: residues 25-47 of SEQ ID NO: 6, residues 59-73 of SEQ ID NO: 6, residues 81-112 of SEQ ID NO: 6, residues 122-131 of SEQ ID NO: 6.

Antibody Production Processes

Processes for the preparation of the monoclonal antibodies, derivatives and variants thereof, and antigen binding fragments thereof are readily available and capable of being performed without difficulty by persons of ordinary skill in the art.

Apart from the hybridoma method of Kohler et al. (1975) and described above in the section entitled "Hybridomas", another non-limiting process that may be utilised is recombinant DNA technology (see, for example, U.S. Pat. No. 4,816,567). For example, the monoclonal antibodies, derivatives and variants thereof, and antigen binding fragments thereof, may be recombinantly produced in any well-established expression system including, but not limited to, baculovirus, yeast (e.g. *Pichia* sp., *Saccharomyces* sp.) *E. coli*, mammalian cells, plants, or transgenic animals (see Breitling and Dubel, 1999, Recombinant Antibodies, John Wiley & Sons, Inc., NY, pp. 119-132).

In some embodiments, nucleic acid sequences encoding monoclonal antibodies, derivatives and variants thereof, and antigen binding fragments thereof in accordance with the present invention may be used in production processes based on recombinant DNA technologies. Non-limiting examples include a heavy chain polynucleotide sequence as defined in SEQ ID NO: 1 or a variant or fragment thereof, and/or a light chain polynucleotide sequence as defined in SEQ ID NO: 2 or a variant or fragment thereof.

A "variant" polynucleotide refers herein to a polynucleotide which differs in sequence from a parent or reference polynucleotide. Polynucleotide sequence divergence may result from mutational changes such as deletions, substitutions, or additions of one or more nucleotides. Each of these changes may occur alone or in combination, one or more times in a given sequence. A "variant" polynucleotide refers to a polynucleotide that has a substantially similar sequence to a parent or reference polynucleotide. In general, two sequences are "substantially similar" if the two sequences have a specified percentage of nucleotides that are the same (percentage of sequence "homology" or sequence "identity"). Sequence homology or identity between two polynucleotide sequences is defined herein as the percentage of nucleotides in the candidate ("variant") sequence that are identical with those of the parent/reference polynucleotide sequence, after aligning the sequences and introducing gaps, if necessary, to achieve the maximum percent sequence identity. If the two sequences which are to be compared with each other differ in length, sequence identity relates to the percentage of the nucleotides of the shorter sequence which are identical with the nucleotides of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711) and/or the program "fasta20u66" (version 2.0u66, September 1998 by William R. Pearson and the University of Virginia; see also W. R. Pearson (1990), Methods in Enzymology 183, 63-98). The degree of sequence homology/identity between the variant polynucleotide and the reference/parent polynucleotide may, for example, be at least 75%, 80%, 83% 85%, 88%, 90%, 93%, 95%, 96%, 97%, 98% or 99%.

A polynucleotide "fragment" is a polynucleotide molecule that encodes a constituent or is a constituent of a large parent/reference polynucleotide. In general, the fragment will encode a fragment of an antibody of the present invention, the fragment being capable of specifically binding to GPC-1.

Monoclonal antibodies, derivatives and variants thereof, and antigen binding fragments thereof produced in accordance with the present invention may be isolated from various sources using appropriate methods including, but not limited to, immunoglobulin-binding molecules (for example, proteins A, L, G or H), tags operatively linked to the antibody or antibody fragment (for example, His-tag, c-myc tag), affinity chromatography, and the like.

Monoclonal antibodies, derivatives and variants thereof, and antigen binding fragments thereof as described herein may be produced by hybridomas and/or cell cultures comprising single or mixed populations of hybridomas including, for example, those described in the section above entitled "Hybridomas", then isolated using known techniques. In some embodiments, the monoclonal antibodies can be produced by culturing a single (monoclonal) species of hybridoma cells deposited under the terms of the Budapest Treaty at Cellbank Australia under accession number CBA20140026, and isolated from the culture.

Processes for the preparation and cultivation of the hybridoma cell lines and isolation of the antibody produced are well known to those of ordinary skill in the art and are standard procedures.

Compositions and Kits

Monoclonal antibodies, derivatives and variants thereof, and antigen binding fragments thereof in accordance with the present invention, including those described in the sections above entitled entitled "Monoclonal antibodies" and "Antibody fragments, derivatives and variants", may be included as components of kits and/or compositions (e.g. pharmaceutical compositions).

By way of non-limiting example the kits of the present invention may comprise any one or more of an antibody, antibody variant, antibody fragment, antibody derivative, chimeric antibody, or hybridoma cells according to the present invention, in any combination. The hybridoma cells may be deposited at Cellbank Australia under accession number CBA20140026.

The kits may additionally include any number of additional components including, for example, reagents for cell culture, reference samples, buffers, labels, and written instructions for performing a detection assay using components of the kit.

The kits may be fragmented or combined kits.

The present invention also provides compositions comprising any one or more of an antibody, antibody variant, antibody fragment, antibody derivative, chimeric antibody, or hybridoma cells according to the present invention.

By way of non-limiting example compositions according to the present invention may comprise any one or more of an antibody, antibody variant, antibody fragment, antibody derivative, chimeric antibody, or hybridoma cells according to the present invention, in any combination. The hybridoma cells may be deposited at Cellbank Australia under accession number CBA20140026.

The compositions may be pharmaceutical compositions. The pharmaceutical compositions may comprise a pharmaceutically acceptable diluent, excipient and/or carrier, as known to those of ordinary skill in the art. To prepare the pharmaceutical compositions, component/s to be included may be mixed with the pharmaceutically acceptable diluent, carrier and/or excipient (see, for example Remington's Pharmaceutical Sciences and U.S. Pharmacopeia: National Formulary, Mack Publishing Company, Easton, Pa. (1984)). Formulations of therapeutic and diagnostic agents may be prepared by mixing with physiologically acceptable carriers, excipients, or stabilisers in the form of, for example, aqueous solutions or suspensions, lyophilized powders, slurries, (see, Gennaro (2000) Remington: The Science and Practice of Pharmacy, Lippincott, Williams, and Wilkins, New York, N.Y.; Weiner and Kotkoskie (2000) Excipient Toxicity and Safety, Marcel Dekker, Inc., New York, N.Y.; Avis et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Hardman, et al. (2001) Goodman and Gilman's The Pharmacological Basis of Therapeutics, McGraw-Hill, New York, N.Y.; Lieberman, et al. (eds.) (1990) Pharmaceutical Dosage Forms: Disperse Systems, Marcel Dekker, NY).

Methods for Detection

The present invention provides methods for detecting and/or quantifying the expression of GPC-1 protein in a subject (e.g. by cells of a subject). The methods comprise obtaining cells, a tissue sample, and/or a body fluid sample from the subject, contacting the cells, tissue and/or body fluid sample with an antibody, antibody variant, antibody fragment, antibody derivative, or chimeric antibody, according to the present invention (for example, those described in the sections above entitled "Monoclonal antibodies" and "Antibody fragments, derivatives and variants"), and determining and/or quantifying binding of said antibody, antibody variant, antibody fragment, antibody derivative, or chimeric antibody to the cells, tissue sample, or body fluid sample, of the subject.

The GPC-1 for detection may be present on the surface of the cells and/or expressed internally. The body fluid may be urine. The cells or tissue sample may be prostate cells or prostate tissue. Detecting and/or quantifying GPC-1 expression may be conducted using any known means in the art including, for example, flow cytometry and/or ELISA.

In some embodiments, the antibodies, antibody variants, antibody fragments, antibody derivatives, or chimeric antibodies, used in the methods are produced by a hybridoma according to the present invention (for example, a hybridoma described in the section above entitled "Hybridomas"). In some embodiments, the antibody is a monoclonal antibody produced by hybridoma cells deposited at Cellbank Australia under accession number CBA20140026.

In some embodiments, a solution comprising a single species of antibodies, antibody variants, antibody fragments, antibody derivatives, or chimeric antibodies, capable of detecting GPC-1 is applied to the cells, tissue and/or body fluid sample that may potentially contain GPC-1. The single species of may be produced by hybridoma cells deposited at Cellbank Australia under accession number CBA20140026. Alternatively, a solution comprising multiple species of antibodies, antibody variants, antibody fragments, antibody derivatives, and/or chimeric antibodies, may be applied to the cells, tissue and/or body fluid sample that may contain GPC-1, wherein at least one species in the solution is capable of detecting GPC-1. The species capable of detecting GPC-1 may be produced by hybridoma cells deposited at Cellbank Australia under accession number CBA20140026. In such embodiments, the solution comprising multiple species does not comprise an antibody produced by hybridoma cells deposited at the American Tissue Type Culture Collection (ATCC) under accession number HB11785 and/or hybridoma cells capable of producing an antibody comprising;

a light chain variable region that comprises any one or more of:
   a complementarity determining region 1 (CDR1) comprising or consisting of an amino acid sequence defined by positions 48-58 of SEQ ID NO: 6;
   a complementarity determining region 2 (CDR2) comprising or consisting of an amino acid sequence defined by positions 74-80 of SEQ ID NO: 6;
   a complementarity determining region 3 (CDR3) comprising or consisting of an amino acid sequence defined by positions 113-121 of SEQ ID NO: 6;
   and/or
   one or more light chain variable region FR (framework regions) as defined by a sequence selected from any one or more of: residues 25-47 of SEQ ID NO: 6, residues 59-73 of SEQ ID NO: 6, residues 81-112 of SEQ ID NO: 6, residues 122-131 of SEQ ID NO: 6.

In some embodiments, the level of GPC-1 expression detected in the cells, tissue and/or body fluid sample obtained from the subject may be compared to a control cell sample or a sample population reference of GPC-1 expression levels. In some embodiments, a determination of increased GPC-1 expression in the subject compared to the control or reference may be diagnostic of a disease, or, an increased likelihood of developing a disease, in the subject. The disease may be prostate cancer.

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

EXAMPLES

The present invention will now be described with reference to specific examples, which should not be construed as in any way limiting.

Example 1: Analysis of Antibodies from MIL-38 Hybridoma Populations 1.1 Materials and Methods
MIL-38 Antibody Preparations
Preparations MIL-38 antibody hybridomas were obtained from the following sources:
(i) In house cell stocks of the BLCA-38 hybridoma were used to generate a series of MIL-38 antibody preparations designated 16A, 16B, 16C, 17B, 23A-1, 23A-2, 24A, 25A, 25B, 26B, 30A, 31A, 31B, 31C, 31D, 32B, 32C, 33A, 33B, 33C, 33D, 34A, 34B, 35A, 35C, 35D, 40A, 40B.
(ii) One batch of cells from the in-house stocks was used to generate MIL-38 hybridoma preparations AusMAb 1 and 2 (AM-1 and AM-2).
(iii) A vial of the original deposit of the BLCA-38 hybridoma was retrieved from the ATCC (accession no. HB11785: murine hybridoma BLCA-38). This was cultured and in-house cell stocks were prepared. Antibody preparations from this original stok were designated "Original" (1-O) and "Original IIA";
(iv) A vial of the "Original" cells was used to generate antibody preparation AusMAb 3 (AM-3) and subsequently antibody preparations AusMAb 4 and 5 (AM-4, AM-5). The cells used to generate AusMAb3 and the cells used to generate AusMAb 4 and 5 were separately frozen down in two batches.
(v) From these frozen cells, a preparation termed "Alfio I" was generated from the cell stock used to prepare AM-4 and AM-5, and a preparation termed "Alfio II" was generated from the cell stock used to generate AM-3.
(vi) An early passage (<6) freezedown of cells from the original deposit of the BLCA-38 hybridoma (HB11785) was used to perform single cell cloning and provide a number of clones to characterize. The MIL-38 1F5 clone was selected and deposited at CellBank Australia under deposit number CBA20140026.

The hybridoma stock used as a basis to generate the preparations described in (i)-(vi) above was prepared as described in U.S. Pat. No. 5,622,836[1] to Walker et al., the entire contents of which are incorporated herein by cross-reference.

For purification of MIL-38 antibody, frozen cell stocks were quickly thawed followed by resuspension in RPMI 1640 medium and allowed to grow at 37° C. with 5% $CO_2$ for 24 h. Cells were expanded, split and scaled up in a sequential process. At each step, cells were resuspended in fresh medium and incubated at 37° C. with 5% $CO_2$. After scale up, cells were transferred to sterile serum free medium and grown till the start of death phase. The supernatant was harvested to collect the MIL-38 antibody and filter sterilised. Antibody supernatant was stored at −80° C. until required.

Antibody was purified using Pierce protein G according to the manufacturer's recommendations.

Cells used to generate AusMab clones AM-1-AM-5 were prepared as follows. Cells were revived in DMEM+10% FCS. Once growing well, they were cloned (see below), expanded and frozen down. Cells were then weaned off the FCS and transferred to Gibco HSFM serum free medium (weaning typically took 5 days).

Prior to seeding cells into a Bioreactor, a modified serial dilution was performed to obtain single cells per well in 96 well plates. Conditioned medium was used to promote single cell growth. Individual wells were observed 3 days after plating and the number of 4-8 cell colonies per well was counted. Only wells that contained a single colony were selected for expansion. Expression of the antibody was confirmed prior to expansion.

Following expansion, a portion of the cells were transferred to an Integra two-compartment Bioreactor while the remaining cells were frozen down. Cells were grown in the Bioreactor according to the maunfacturer's instructions. Following harvest, antibody was purified using standard techniques.

Western Blot and Sypro Gel Analysis
Protein Extraction:
DU-145 (MIL-38 antigen positive) or C3 (MIL-38 antigen negative) cells were cultured according to standard tissue cuture techniques. Cell membrane proteins were enriched using the Merck Millipore ProteoExtract Native Membrane Protein Extraction Kit (MPEK) according to the manufacturer's instructions.

Transfer:
Gels were transferred onto a nitrocellulose membrane for 10 min at 2.5 A and 25V maximum using the Transblot Turbo system (Biorad).

Western Blot:
Briefly, after transfer membranes were blocked with 5% skim milk in PBS-Tween (0.1%) for 2 h at room temperature. Primary antibodies (1 µg/ml in 5% skim milk—PBS-Tween (0.1%) were applied and incubated overnight at 4° C. After washing (3× 10 min PBS-Tween (0.1%)) membranes were incubated with secondary antibody (1:2000 sheep-anti-mouse HRP-labelled in 5% skim milk—PBS-Tween (0.1%)). After washing (3×10 min PBS-Tween (0.1%)) antigen was detected by using ECL detection kit (Biorad) and imaging with LAS4000 mini (GE Life Science).

Sypro Gels:
Gels were fixed in fixing solution (10% Ethanol, 7% acetic acid) for 2 h before being transferred into Sypro®Ruby Protein Stain and incubated overnight at room temperature in the dark. Before imaging gels were rinsed and washed with destaining solution (10% Ethanol, 7% acetic acid) for a minimum of 2 h. Imaging was performed with a Pharos X Scanner.

Immunofluorescence Assay (IFA)
IFA:
Cells were grown on coverslips until 75% confluent and placed in 6 well plates. The cells were washed with PBS followed by fixing with acetone. Cells were washed again with PBS followed by incubation with TBS then blocked with PBS containing 5% skim milk. Cells were then incubated in the dark with MIL-38, chimeric MIL-38 or Cetuximab followed by incubation with a Goat anti-mouse or Goat anti-human antibody labelled with FITC or Alexa488. Both antibodies were prepared in PBS containing 1% skim milk followed. Washing with PBS was performed between the primary and secondary antibody incubations. After secondary incubation, cells were washed with PBS containing DAPI and visualised for green fluorescence (MIL-38 positive).

SDS-PAGE Electrophoresis

SDS-PAGE:

Samples were mixed with non-reducing SDS-containing sample buffer and loaded onto a 4-15% precast polyacrylamide gel (Criterion TGX; Biorad). Gels were run for 10 min at 80V and additional 50 min at 200V in Tris-Glycine running buffer.

1.2 Results

Western Blot

Preparations of MIL-38 antibodies derived from the following sources were compared side by side:
(i) hybridoma cells from the ATCC (preparation 1-O, "original");
(ii) two separate preparations of antibody produced from hybridoma cells maintained by the Applicant company (preparations 37A and 40A);

Equivalent western blot reactivity was observed for all three preparations (FIG. 1). All three preparations provided a double band for both the heavy and light chain suggesting a non-clonal population.

Immunofluorescence Assay (IFA)

Different antibody preparations ("1-Original" (1-O), 40A, and 37A) used on a variety of cell lines provided equivalent IFA reactivity (Table 1).

TABLE 1

IFA reactivity of different antibody MIL-38 preparations on various cell lines

| Sample | 1° Ab (MIL-38) | 2° Ab | Reaction | Comments |
|---|---|---|---|---|
| DU145 | 37A | Goat Anti-mouse-FITC | 3+ | |
| | 40A | | 3+ | |
| | Original | | 4+ | |
| | — | | − | Yellow fluorescence |
| PZHPV7 | 37A | | 2+ | |
| | 40A | | 2+ | |
| | Original | | 2+ | |
| | — | | − | Yellow fluorescence |
| RWPE1 | 37A | | 3+ | |
| | 40A | | 2+ | |
| | Original | | 2+ | |
| | — | | − | |
| T24 | 37A | | 2+ | |
| | 40A | | 2+ | |
| | Original | | 2+ | |
| | — | | − | Some Background |
| C3 | 37A | | + | |
| | 40A | | + | |
| | Original | | + | |
| | — | | − | Yellow fluorescence |

Figure 2A:
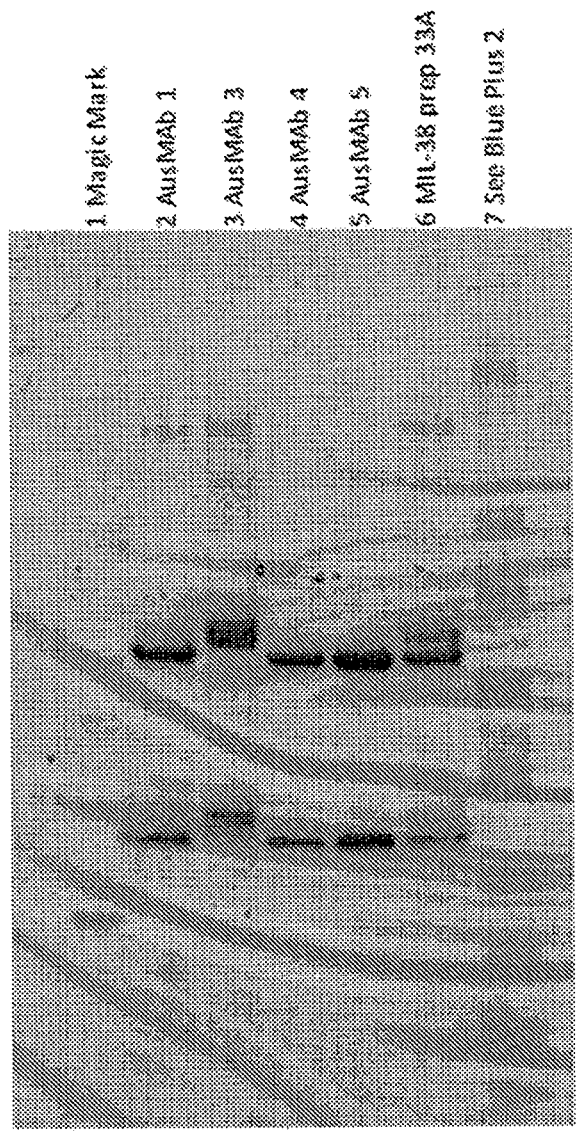
FIG. 2A shows segregation of heavy and light chain components in each antibody preparation by SDS-PAGE electrophoresis; Lanes: 1 (Magic Marker); 2 (AusMab 1); 3 (AusMab 3); 4 (AusMab 4); 5 (AusMab 5); 6 (MIL-38 prep 33A); 7 (See Blue Plus2)
Figure 2B:
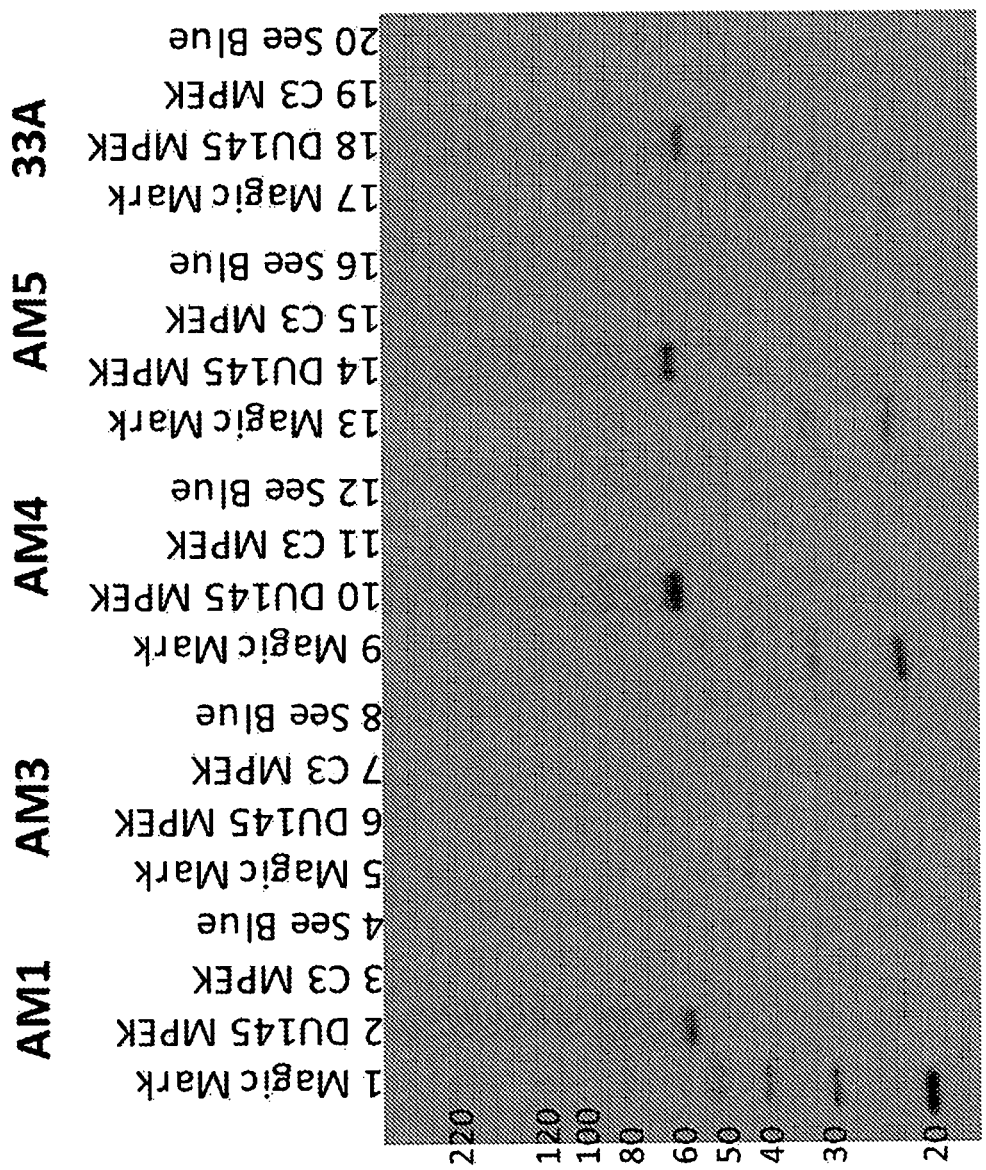
FIG. 2B shows the results of Western blot analyses using MIL-38 antibodies from various preparations on extracts from DU-145 and C3 cell lines.

NB:
antibodies from preps 1-O ("1-Original"), 40A and 37A were used in IFA on a range of cell lines
comparable IFA reactivity was observed for all three preps Analyses of Different MIL-38 Antibody Preparations Size and reactivity of MIL-38 antibody preparations sourced from preparations AM-1-AM-5 (generated by AusMAb Pty Ltd) and in-house MIL-38 antibody preparation 33A were compared by SDS-PAGE (FIG. 2A) and Western Blot (FIG. 2B).

The in-house MIL-38 preparation of antibodies exhibited a double band for both the heavy and light chain suggesting a non-clonal population (see FIG. 2A). AusMAb MIL-38 antibody preparations (AusMab 1, AusMab 3, AusMab 4, AusMab 5) showed single bands for both heavy and light chains. MIL-38 antibody preparation 33A showed a double band for both the heavy and light chain suggesting a non-clonal population. Notably, AusMAb 3 bands exhibited a higher MW than AusMab 1, AusMab 4, AusMab 5, and 33A suggesting the existence of two distinct clonal populations in the source 1-0 stocks.

AusMAb 3 (AM-3) antibodies also did not react with the MIL-38 antigen whereas AusMab 1, AusMab 4, AusMab 5, and preparation 33A antibodies did (FIG. 2B).

Analyses of Additional in-House MIL-38 Preparations

Figure 3A:
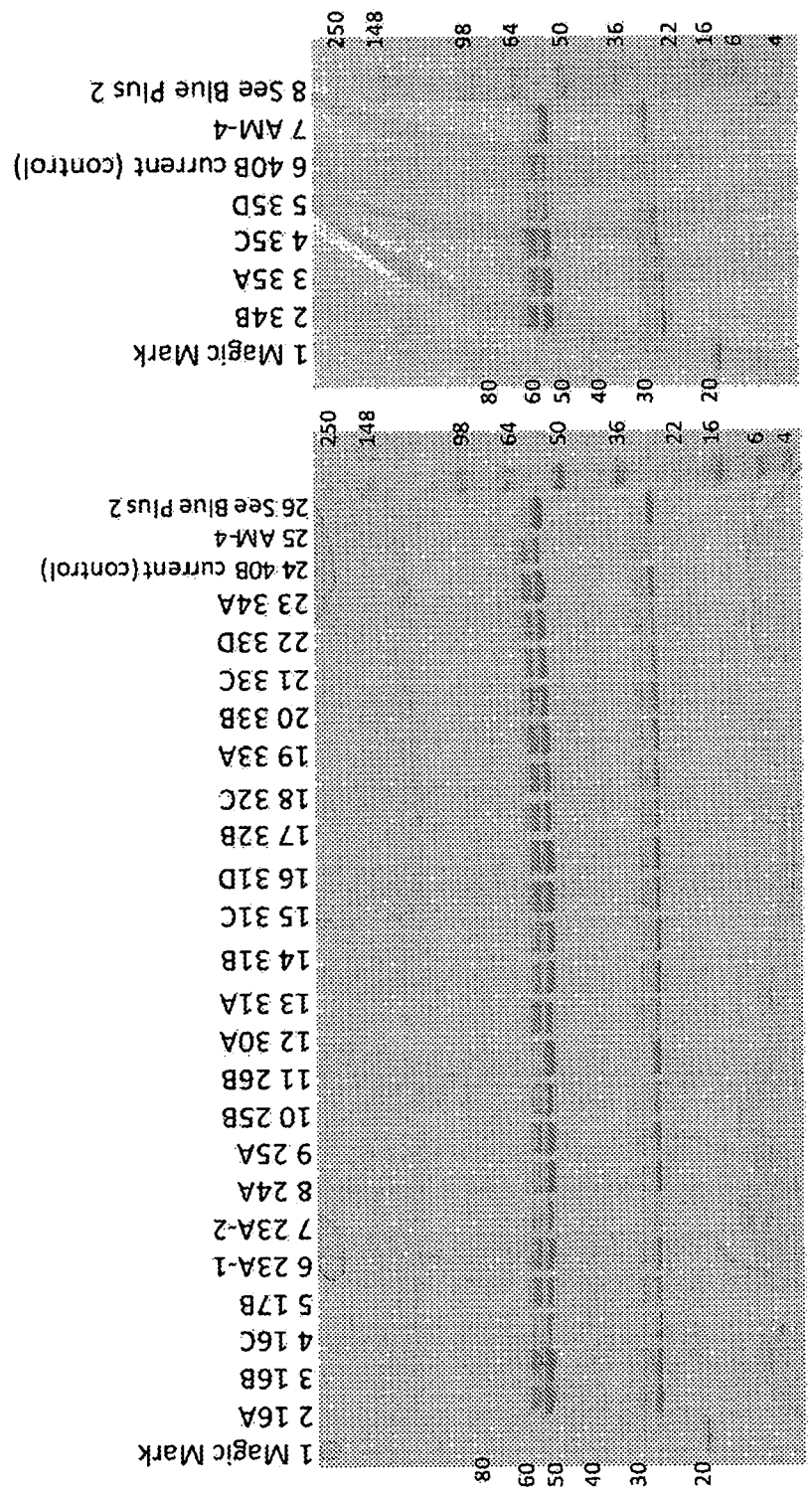
FIG. 3A shows segregation of heavy and light chain components in each MIL-38 antibody preparation by SDS-PAGE electrophoresis.

SDS-PAGE electrophoresis was used to analyse heavy and light chain MW of various other MIL-38 antibody preparations generated from BLCA-38 hybridoma stocks and stored in-house. Double bands for heavy and light chains were observed in all preparations (FIG. 3A). In contrast, the AusMab 4 (AM-4) antibody preparation showed single bands for both heavy and light chains.

Figure 3B:
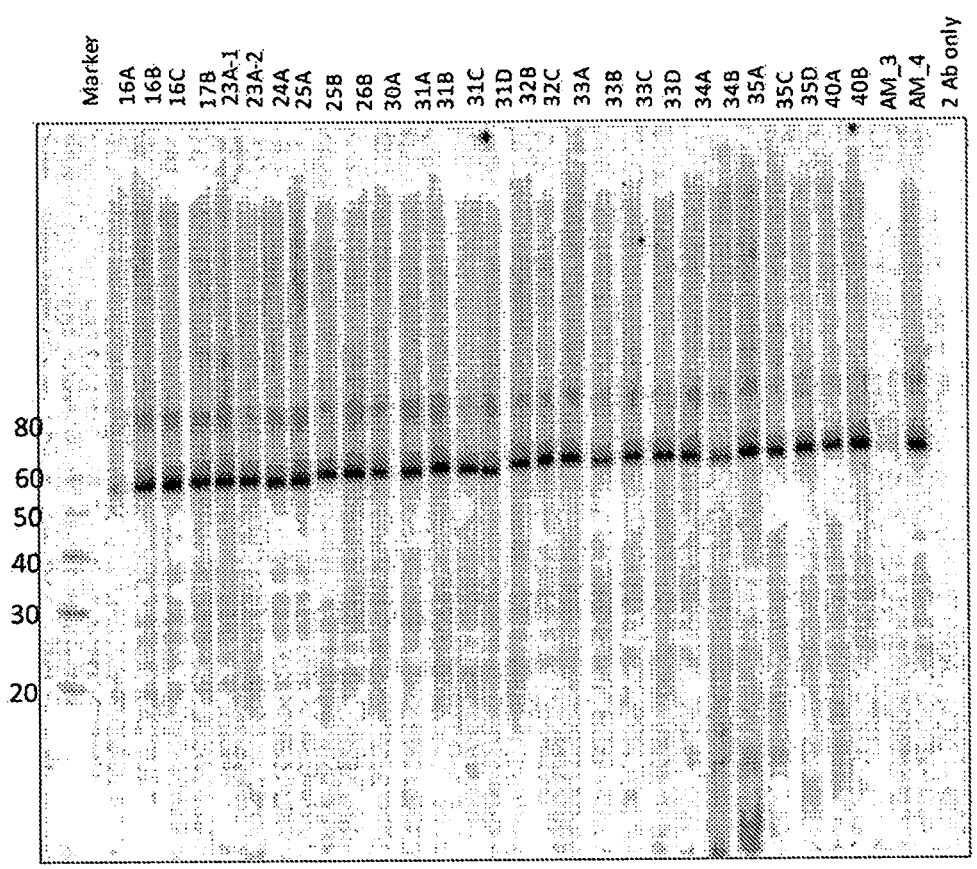
FIG. 3B shows the results of Western blot analyses using MIL-38 antibodies from each preparation on DU-145 cell extracts.

Western blot reactivity of various in-house MIL-38 antibody preparations to DU-145 MPEK extract was consistent across preparations. AusMab 4 (AM-4) reacted to DU-145 MPEK extract whereas AusMab 3 (AM-3) was not reactive to DU-145 MPEK extract (FIG. 3B).

1.2 Discussion

From these results it is evident that MIL-38 hybridoma stocks from both in-house and ATCC stocks contained mixed population of cells. Cloning the two identifiable populations (AusMab populations) gave two antibodies of different molecular weights. One of these two antibody species is non-reactive to the MIL-38 antigen while the other shows equivalent reactivity to MIL-38 produced from the mixed population.

Example 2: Analysis of Additional MIL-38 Antibody Populations 2.1 Materials and Methods Preparation of MIL-38 Antibodies Preparations of frozen hybridoma cell populations derived from AusMab 3 (AM-3) or AusMab 4 (AM-4) and AusMab 5 (AM-5) were used. The cells used in the derivation of AM-3 were termed "Alfio II". Following screening indicating that AM-3 was non-reactive to DU-145 MPEK extracts, earlier passage stocks were investigated to identify a positive clone. These early passage cells were used to derive AM-4 and termed "Alfio I". Both cell stocks were kept for storage and to allow in-house production of MIL-38 antibody.

For MIL-38 batch production of Original IIA, Alfio I and Alfio II, stocks were quickly thawed followed by resuspension in RPMI 1640 medium and allowed to grow at 37° C. with 5% $CO_2$ for 24 h. Cells were expanded, split and scaled up in a sequential process. At each step, cells were resuspended in fresh medium and incubated at 37° C. with 5% $CO_2$. After scale up, cells were transferred to sterile serum free medium and grown till the start of death phase. The supernatant was harvested to collect to MIL-38 antibody and filter sterilised. Antibody supernatant was stored at −80° C. until required. Antibody was purified using Pierce protein G according to the manufacturer's recommendations.

Western Blot and Sypro Gels

Western blot and preparation of Sypro gels were performed essentially according to the methods set out in Example 1 above (see section 1.1)

Western blotting was performed under the following conditions:
4-12% Bis-Tris gel
Blocking: overnight
Western Blot regime: Primary antibody 1 hr, 10 µg per membrane piece, Wash 3×10 mins,
Secondary antibody 1hr, secondary antibody 1/2000 Goat-mouse HRP
Cells: tested against DU-145 and C3 MPEK extracts Immunofluorescence Assays Immunofluorescence assays were performed essentially according to the methods set out in Example 1 above (see section 1.1)

2.2 Results

Western Blots

Western blot reactivity of Alfio I, Alfio II, 36A, AusMAb and "original IIA" (a MIL-38 preparation prepared from hybridoma cells of ATCC HB11785) was tested on DU-145 and C3 MPEK cell extracts.

Figure 4A:
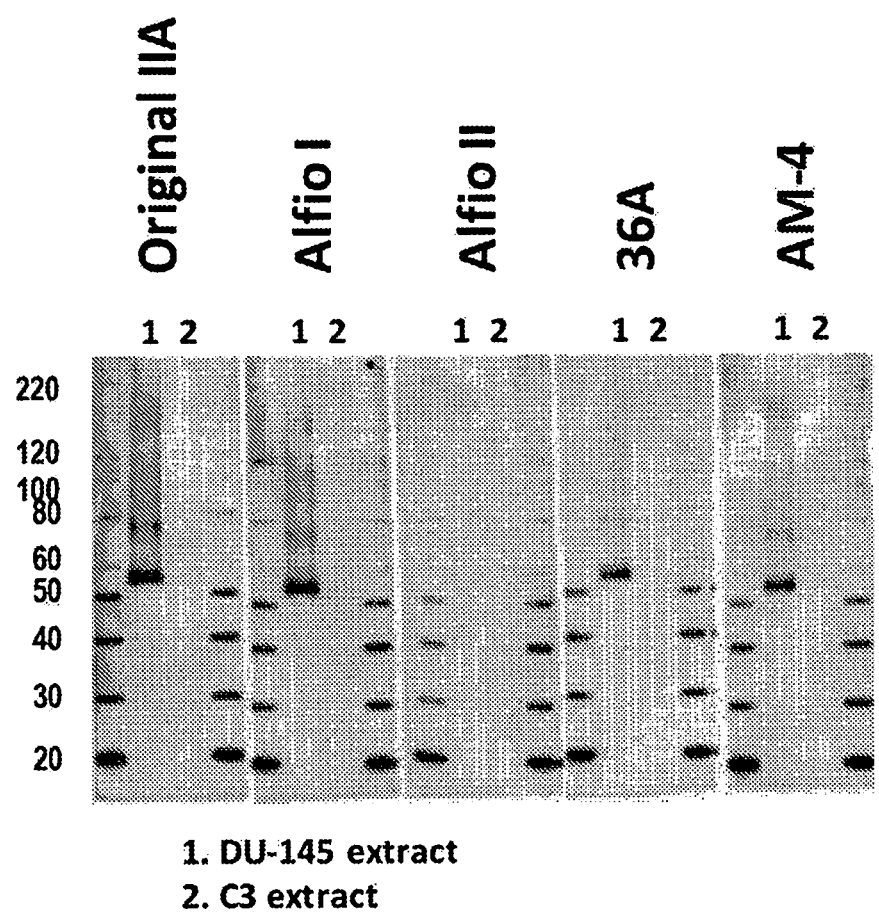
FIG. 4A shows the results of Western blot analyses using original IIA, Alfio I, Alfio II, 36A and AusMAb 4 (AM-4) MIL-38 antibody preparations on extracts from DU-145 and C3 cells.

Western blot reactivity of Alfio II resembled that of preparation AM-3 (FIG. 4A). Original IIA and Alfio I resembled preparation 36A (in-house Biclonal) (FIG. 4A).

Sypro Gel Analysis

Figure 4B:
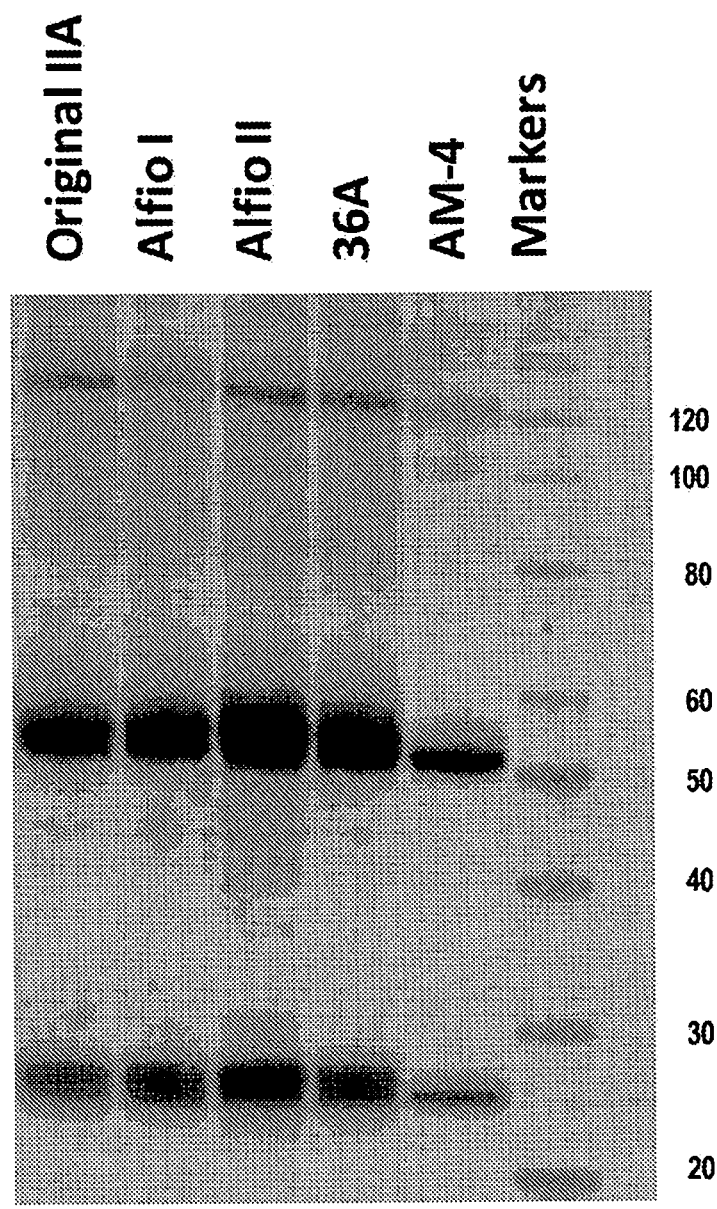
FIG. 4B shows a reducing Syprogel demonstrating segregation of heavy and light chain components of MIL-38 antibody preparations (original IIA, Alfio I, Alfio II, 36A and AusMAb 4 (AM-4)) by SDS-PAGE electrophoresis. Original IIA=in-house preparation derived from stocks of ATCC accession no. HB11785 (murine hybridoma BLCA-38); Alfio I=mixed MIL-38 antibody population derived from ATCC accession no. HB11785; Alfio II=single antibody population derived from the mixed population of ATCC accession no. HB11785.

Dual bands in separated heavy chain fractions were not as clear as previously observed, while dual bands in separated light chain fractions could be clearly distinguished. Separated light chain fractions of the original IIA, Alfio I, and 36A MIL-38 antibody preparations all contained two bands. In contrast, the separated light chain fraction of Alfio II contained a single light chain specie, with higher MW (i.e. like the AM-3 MIL-38 antibody preparation). Note that more Alfio II antibody was loaded onto the gel than for the other antibodies which resulted in a broader band for the light chain specie. Separated heavy and light chain fractions from the AM-4 MIL-38 antibody were clearly distinct from either the biclonal or AM-3-like forms (FIG. 4B).

Immunofluorescence Assays

Figure 5A:
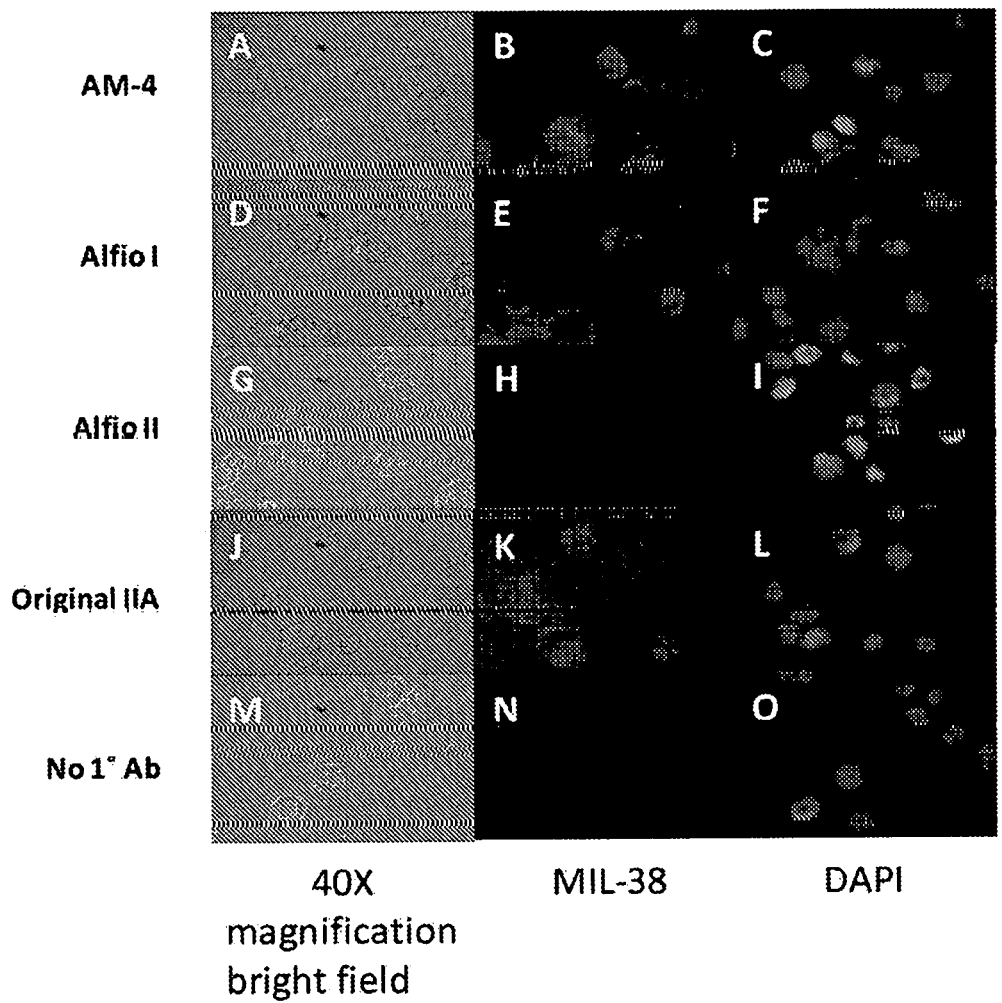
FIG. 5A shows images from immunofluorescence assays using various preparations of MIL-38 antibodies on DU-145 cells. Parts A, D, G, J and M show bright field images of the stained cells; Parts B (AM-4), E (Alfio I), H (Alfio II), and K (Original IIA) show binding of MIL-38 antibody preparations to DU145 cells; Part N shows secondary antibody control for DU-145 cells; Parts C, F, I, L and O show DAPI staining of the cells.
Figure 5B:
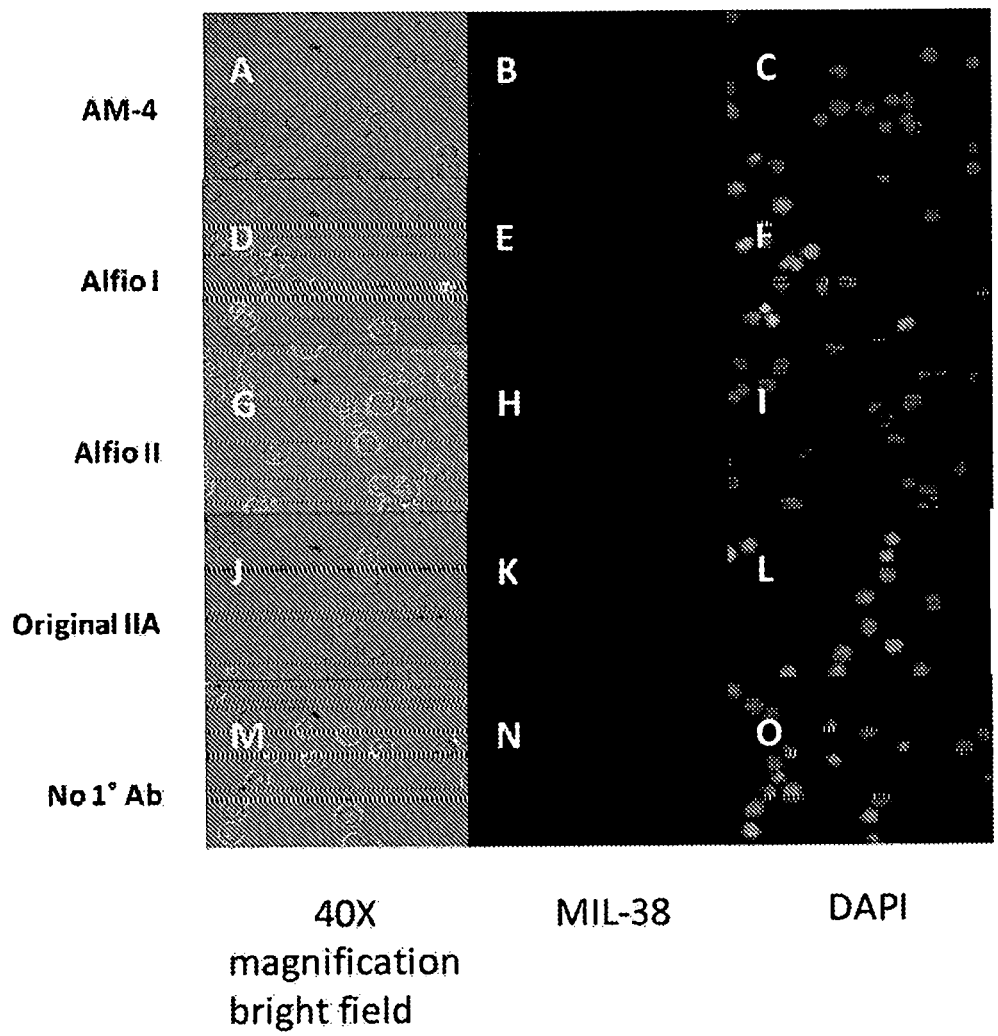
FIG. 5B shows images from immunofluorescence assays using various preparations of MIL-38 antibodies on C3 cells. Parts A, D, G, J and M show bright field images of the stained cells; Parts B (AM-4), E (Alfio I), H (Alfio II), and K (Original IIa) show binding of MIL-38 antibody preparations to C3 cells; Part N shows secondary antibody control for C3 cells; Parts C, F, I, L and O show DAPI staining of the cells.

Consistent with the western blot results, IFA analysis of DU-145 cells showed that AM-4, Alfio I and original IIA gave good IFA reactivity, whereas Alfio II (equivalent to AM-3 in western blot) showed no reactivity in IFA (FIG. 5A). No reactivity of any preparations was observed with the negative control cell line C3 (FIG. 5B).

2.3 Discussion

These analyses indicate that Alfio I is a biclonal MIL-38 antibody population whereas Alfio II is an AM-3-like (monoclonal) antibody population, and further confirm that MIL-38 antibody preparation AM-4 is a monoclonal antibody population.

It is therefore evident that biclonal MIL-38 antibody populations such as Alfio I contain a mixture of the distinct AM-3 and AM-4 monoclonal antibody populations.

Figure 6A:
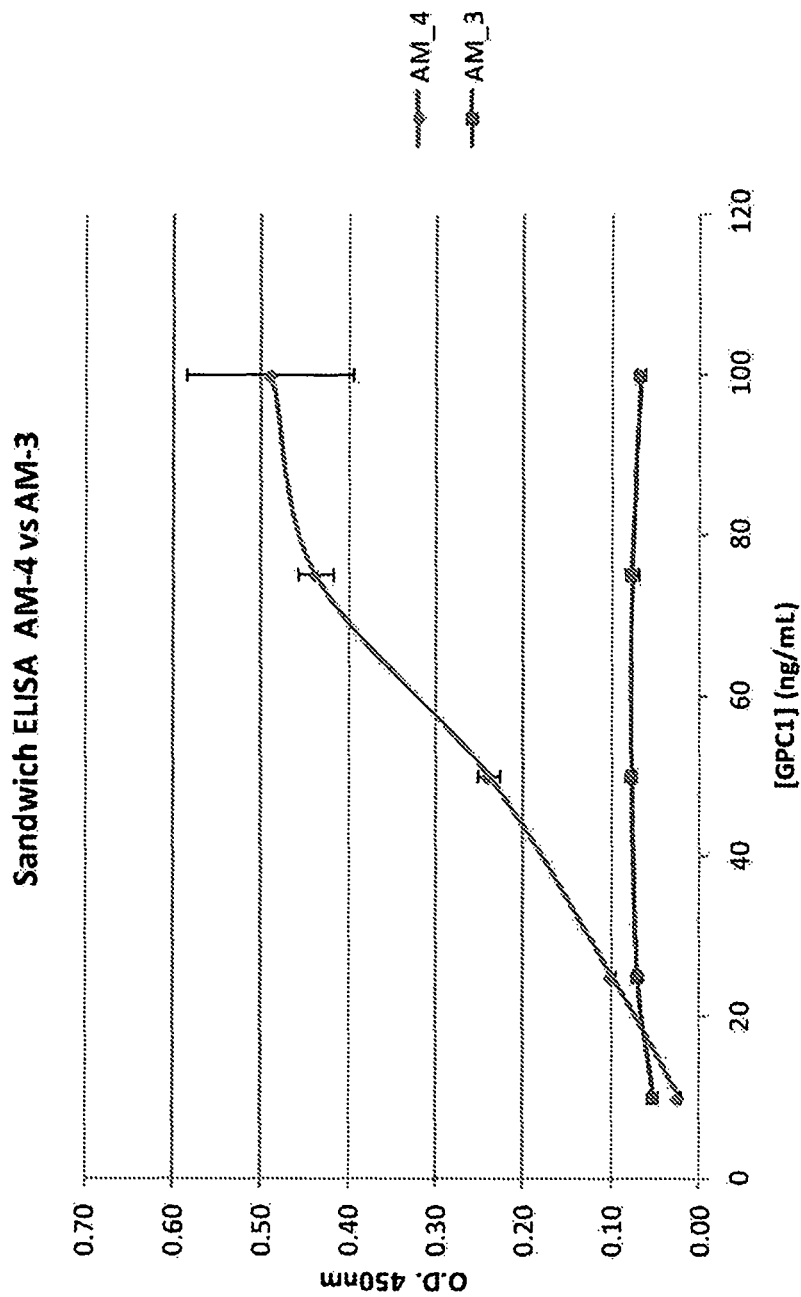
FIG. 6A shows comparative sandwich ELISAs using AM-3 and AM-4 as capture antibodies.

Example 3: Comparison of MIL-38 Antibody Populations for ELISA Assay 3.1 Materials and Methods Ninety-six well plates were coated with MIL-38 preps AM-3 or AM-4 (1 µg/well) in carbonate buffer pH 9.5 overnight. Plates were blocked with PBS-Tween (0.1%) containing 5% skim milk at 37° C. and washed. Antigen (recombinant human GPC-1 produced from NS0 cells) diluted in Buffer II (20 mM HEPES pH 7.5, 0.5 mM EDTA, 0.5% Triton X-100) with the addition of 150 mM NaCl and incubated overnight at 37° C. Detection was performed with biotinylated AM-4 followed by detection with avidin HRP (1 µg/mL). TMB (Sigma cat no T0440) was added and stopped with TMB stop solution (Sigma S5814). Absorbance was read 450 nm. Results are shown in FIG. 6A.

Figure 6B:
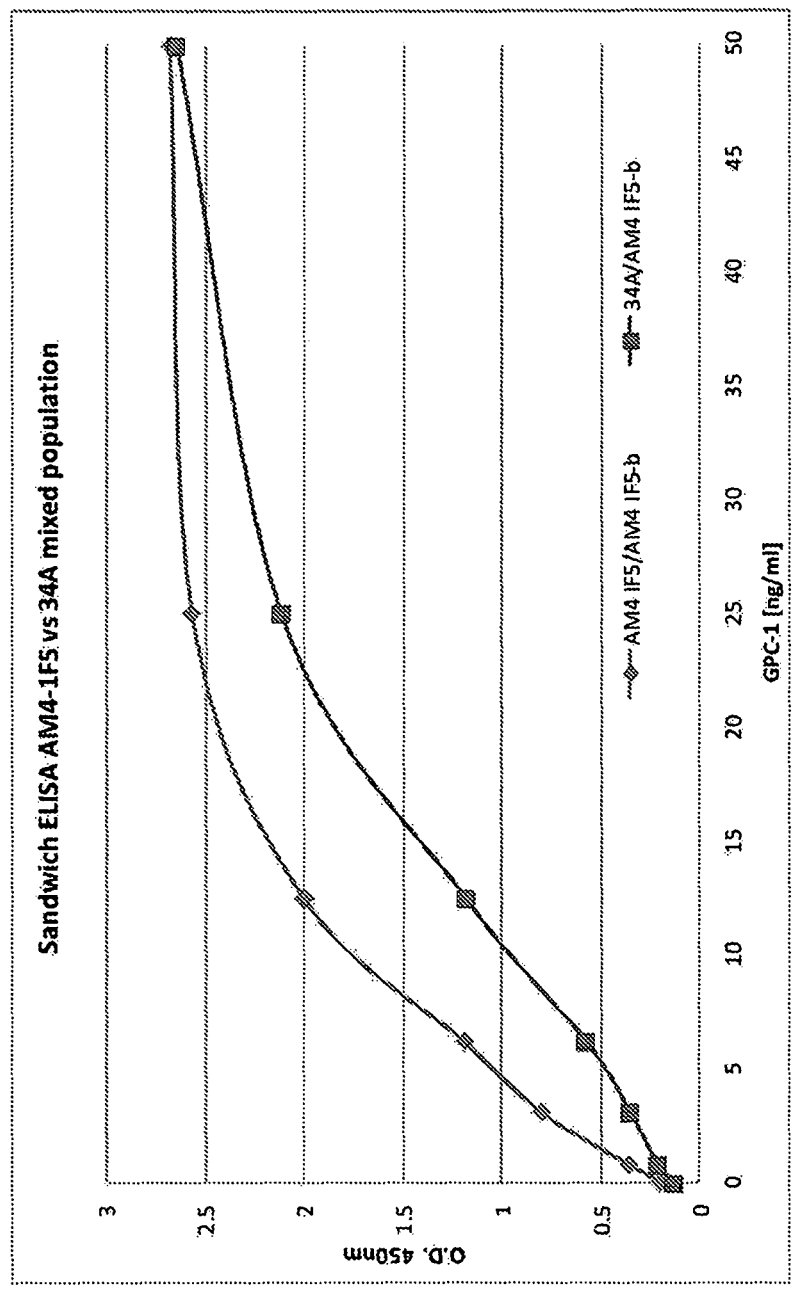
FIG. 6B shows comparative sandwich ELISAs using either a mixed preparation (34A) or a clonal population (AM-4 1F5) as capture antibodies.

In a second experiment, ninety-six well plates were coated with MIL-38 preps 34A or AM-4 (2.5 µg/well) in PBS pH 7.2 for 1 h at room temperature. Plates were blocked with Blocker Casein (Thermo) in PBS-Tween (0.05%) for 1 h at 37° C. Following washing, antigen (GPC-1 NS0) was diluted in TBS pH 7.2 containing 50 mM Tricine and 150 mM NaCl and incubated at 37° C. for 1 h. Detection was performed with biotinylated AM-4 clone 1F5 followed by detection with avidin HRP (1 µg/mL). TMB (Sigma cat no 10440) was added and stopped with TMB stop solution (Sigma S5814). Absorbance was read 450 nm. Results are shown in FIG. 6B.

3.2.1 Results

The first ELISA described above was developed using MIL-38 to capture recombinant NS0-produced GPC-1 (i.e. MIL-38 antigen). This experiment compared monoclonal AM-3 MIL-38 and monoclonal AM-4 MIL-38 for capture. AM-3 did not function as a capture agent in a sandwich ELISA assay (FIG. 6A).

The second ELISA described above compared the ELISA signal obtained when a mixed population of MIL-38 (34A) was compared to that obtained from a monoclonal AM-4-1F5 clone. Using AM-4 1F5 as a capture agent provided a higher ELISA signal than using the mixed 34A antibody population (FIG. 6B).

3.2.2 Discussion

The sandwich ELISA results demonstrate that only the AM-4-like forms of the monoclonal MIL-38 antibody have utility in detecting antigen as a capture reagent and that a capture agent containing a monoclonal population provides a superior ELISA signal to that consisting of a mixed population.

Example 4: Sequence Analysis of MIL-38 Antibody Populations 4.1 Materials and Methods Heavy and Light Chain Sequencing (DNA)

Three separate sequencing runs were performed. The first run (coded 224945) utilised bi-clonal hybridoma cells from the 1-O preparation. The second run (coded 449295-1) utilised cells from Alfio I a hybridoma stock that was used to generate AM-4. The third run (coded 449295-5) utilised cells from Alfio II, a hybridoma stock that was used to generate AM-3.

For sequencing runs 224945 (1-O) and 449295-1 (Alfio I), total RNA was extracted from frozen hybridoma cells and cDNA was synthesized from the RNA. PCR was then performed to amplify the variable regions (heavy and light chains) and constant regions of the antibody, which were then cloned into a standard cloning vector separately and sequenced.

Total RNA was isolated from the hybridoma cells following the technical manual of TRIzol® Plus RNA Purification System. The total RNA was analysed by agarose gel electrophoresis.

Total RNA was reverse transcribed into cDNA using isotype-specific anti-sense primers or universal primers following the technical manual of SuperScript™ III First-Strand Synthesis System. The antibody fragments of $V_H$, $V_L$, $C_H$ and $C_L$ were amplified according to the standard operating procedure of RACE of GenScript.

Amplified antibody fragments were separately cloned into a standard cloning vector using standard molecular cloning procedures.

Colony PCR screening was performed to identify clones with inserts of correct sizes. No less than five single colonies with inserts of correct sizes were sequenced for each antibody fragment.

$V_H$ and $V_L$ plasmids encoded the full-length variable regions of the antibody and a part of $C_H1$ and $C_L$. $C_H$ plasmid encoded a part of $C_H1$ and full-length $C_H2$ and $C_H3$. $C_L$ plasmid encoded a part of $C_L$. In order to get full-length constant regions or heavy/light chain, the part of constant regions encoded by $V_H$ and $V_L$ plasmids and the part of constant regions encoded by $C_H$ and $C_L$ plasmids were amplified by PCR separately, and then overlap extension PCR was employed to obtain full-length DNAs. Five single colonies with correct $V_H$, $V_L$, $C_H$ and $C_L$ insert sizes were sent for sequencing. Sequencing run 449295-5 (Alfio II) encountered difficulty obtaining sequence corresponding to the expected IgG1 heavy chain sequence. Two RNA preparations were performed. For the 1st batch of cells, oligo-dT primer and CDS III primers were used for reverse transcription (RT). $V_H/C_H$ and $V_K/C_K$ were amplified by PCR using IgG1 and IgK specific primers, partial mouse β-actin gene was amplified as positive control. Normal light chain bands were obtained easily while only weak VH could be observed on the gel. Five individual colonies with correct $V_K$ and $C_K$ insert sizes were sent for sequencing. The $V_K$ and $C_K$ genes of five different clones were found to be nearly identical. The consensus light chain sequences from the Alfio II hybridoma is listed below. One unproductive heavy chain sequence was obtained from eight randomly sequenced $V_H$ positive clones, shown as below. Three kinds of heavy chain constant region sequences were obtained from ten randomly sequenced $C_H$ positive clones (one $IgG_1C_H$, one $IgG_{2a}C_H$ and eight $IgG_{2b}C_H$). In order to avoid the influence of potential class switching, amplification of the $C_H$ using IgM specific primer was performed, but no target PCR product was obtained. There was also no target PCR product when full length heavy chain ($V_H$-$C_H$) was amplified using heavy chain FR1 degenerate primers.

As no productive heavy chain could be obtained after several attempts, isolation of heavy chain sequence from the 2nd vial of Alfio II cells was attempted. For the 2nd vial of cells, oligo-dT primer was used for reverse transcription initially. $V_H$ was amplified using IgG1, IgG2b, IgM, IgA specific primers and IgG degenerate primer, respectively, and $V_K$ was amplified using IgK specific primers. Productive light chain and unproductive heavy chain, which were identical with previous results, were obtained. Reverse transcription using Random 6 mers primer was also attempted without success.

In summary, multiple attempts to isolate light chain and heavy chain sequence were made. One rearranged light chain sequence was consistently obtained after different attempts on two batches of cells. However, only weak $V_H$ target PCR products were observed and sequencing did not result in any consistent heavy chain sequence.

Results

Sequence Summary Table

Table 2 below provides an overview of heavy and light chain nucleic acid and protein sequences of the antibodies studied, indicating the positions of various internal regions.

TABLE 2

Overview of antibody sequences and internal regions

| DNA Seq ID# | | Leader | HFR1 | HCDR1 | HFR2 | HCDR2 | HFR3 | HCDR3 | HFR4 | CH1-CH3 | Hinge |
|---|---|---|---|---|---|---|---|---|---|---|---|
| 1 | AM4 Heavy | 1-57 | 58-147 | 148-162 | 163-204 | 205-255 | 256-351 | 352-378 | 379-411 | 412-1383 | 703-741 |
| 7 | Chimeric heavy | 1-57 | 58-147 | 148-162 | 163-204 | 205-255 | 256-351 | 352-378 | 379-411 | 412-1401 | 706-750 |
| | | Leader | LFR1 | LCDR1 | LFR2 | LCDR2 | LFR3 | LCDR3 | LFR4 | CL | |
| 2 | AM4 Light | 1-60 | 61-129 | 130-162 | 163-207 | 208-228 | 229-324 | 325-351 | 352-381 | 382-702 | |
| 5 | AM3 light | 1-72 | 73-141 | 142-174 | 175-219 | 220-240 | 241-336 | 337-363 | 364-393 | 394-714 | |
| 8 | Chimeric light | 1-60 | 61-129 | 130-162 | 163-207 | 208-228 | 229-324 | 325-351 | 352-381 | 382-702 | |
| AA Seq ID# | | Leader | HFR1 | HCDR1 | HFR2 | HCDR2 | HFR3 | HCDR3 | HFR4 | CH | Hinge |
| 3 | AM4 heavy | 1-19 | 20-49 | 50-54 | 55-68 | 69-85 | 86-117 | 118-126 | 127-137 | 138-461 | 235-247 |
| 9 | Chimeric heavy | 1-19 | 20-49 | 50-54 | 55-68 | 69-85 | 86-117 | 118-126 | 127-137 | 138-467 | 236-250 |
| | | Leader | LFR1 | LCDR1 | LFR2 | LCDR2 | LFR3 | LCDR3 | LFR4 | CL | |
| 4 | AM4 light | 1-20 | 21-43 | 44-54 | 55-69 | 70-76 | 77-108 | 109-117 | 118-127 | 128-234 | |
| 6 | AM3 light | 1-24 | 25-47 | 48-58 | 59-73 | 74-80 | 81-112 | 113-121 | 122-131 | 132-238 | |
| 10 | Chimeric light | 1-20 | 21-43 | 44-54 | 55-69 | 70-76 | 77-108 | 109-117 | 118-127 | 128-234 | |

Notes:
HFR = heavy chain framework region; HCDR = heavy chain complementarily determining region; CH = heavy chain constant region; LFR = light chain framework region; LCDR = light chain complementarily determining region; CL = light chain constant region
Sequences provided in columns 3-12 are indicative of positions within sequence defined in column 1 by SEQ ID NO.

Sequencing (DNA)

The isolated total RNA of the sample was run alongside a DNA marker (Marker III-TIANGEN, Cat. No.: MD103) on a 1.5% agarose/GelRed™ gel.

Four microliters of PCR products of each sample were run alongside the DNA marker (Marker III) on a 1.5% agarose/GelRed™ gel. The PCR products were purified and stored at −20° C. until further use.

The $V_H$, $V_L$, $C_H$ and $C_L$ genes of five different clones were nearly identical. The consensus sequence, listed below, was determined to be the sequence of the antibody produced by the monoclonal hybridoma population (AM-4).

AM-4 MIL-38 Mouse $IgG_1$ Heavy Chain DNA Consensus Sequence (SEQ ID NO: 1)
ATGGCTTGGGTGTGGACCTTGCTATTCCTGATGGCTGCTGCCCAAAGTAT

CCAAGCACAGATCCAGTTGGTGCAGTCTGGACCTGAGCTGAAGAAGCCTG

GAGAGACAGTCAAGATCTCCTGCAAGGCTTCTGGTTATGCCTTCACAGAC

TATTCAATGAACTGGGTGAAGCAGGCTCCAGGAAAGGGTTTAAGGTGGAT

GGGCTGGATAAACACTGAGACTGGTGAGCCAACATATACAGATGACTTCA

AGGGACGGTTTGCCTTCTCTTTGGAAACCTCTGCCAGCACTGCCTTTTG

CAGATCAACAACCTCAGAAATGAAGACACGGCTACATATTTCTGTGCTAG

ACACTATGATTACGGGGGGTTTCCTTACTGGGGCCAAGGGACTCTGGTCA

CTGTCTCTGCAGCCAAAACGACACCCCCATCTGTCTATCCACTGGCCCT

GGATCTGCTGCCCAAACTAACTCCATGGTGACCCTGGGATGCCTGGTCAA

GGGCTATTTCCCTGAGCCAGTGACAGTGACCTGGAACTCTGGATCCCTGT

CCAGCGGTGTGCACACCTTCCCAGCTGTCCTGCAGTCTGACCTCTACACT

CTGAGCAGCTCAGTGACTGTCCCCTCCAGCACCTGGCCCAGCGAGACCGT

CACCTGCAACGTTGCCCACCCGGCCAGCAGCACCAAGGTGGACAAGAAAA

TT*GTGCCCAGGGATTGTGGTTGTAAGCCTTGCATATGTAC*AGTCCCAGA

AGTATCATCTGTCTTCATCTTCCCCCCAAAGCCCAAGGATGTGCTCACCA

TTACTCTGACTCCTAAGGTCACGTGTGTTGTGGTAGACATCAGCAAGGAT

GATCCCGAGGTCCAGTTCAGCTGGTTTGTAGATGATGTGGAGGTGCACAC

AGCTCAGACGCAACCCCGGGAGGAGCAGTTCAACAGCACTTTCCGCTCAG

TCAGTGAACTTCCCATCATGCACCAGGACTGGCTCAATGGCAAGGAGTTC

AAATGCAGGGTCAACAGTGCAGCTTTCCCTGCCCCCATCGAGAAAACCAT

CTCCAAAACCAAAGGCAGACCGAAGGCTCCACAGGTGTACACCATTCCAC

CTCCCAAGGAGCAGATGGCCAAGGATAAAGTCAGTCTGACCTGCATGATA

ACAGACTTCTTCCCTGAAGACATTACTGTGGAGTGGCAGTGGAATGGGCA

GCCAGCGGAGAACTACAAGAACACTCAGCCCATCATGGACACAGATGGCT

CTTACTTCGTCTACAGCAAGCTCAATGTGCAGAAGAGCAACTGGGAGGCA

GGAAATACTTTCACCTGCTCTGTGTTACATGAGGGCCTGCACAACCACCA

TACTGAGAAGAGCCTCTCCCACTCTCCTGGTAAATGA

Individual regions of mouse heavy chain encoded sequence are highlighted with alternating bolded/unbolded text. Positions: 1-57=leader sequence; 58-147=framework region (HFR1); 148-162=complementarity determining region (HCDR1); 163-204=HFR2; 205-255=HCDR2; 256-351=HFR3; 352-378=HCDR3; 379-411=HFR4; 412-1383=constant regions (CH1-CH3); 703-741=hinge region (italicized); 1384-1386=stop codon.

AM-4 MIL-38 Mouse Kappa Light Chain DNA Consensus Sequence
(SEQ ID NO: 2)
ATGAGTGTGCTCACTCAGGTCCTGGCGTTGCTGCTGCTGTGGCTTACAGG

TGCCAGATGTGACATCCAGATGACTCAGTCTCCAGCCTCCCTATCTGCAT

CTGTGGGAGAAACTGTCACCATCACATGTCGAGCAAGTGGGAATGTTCAC

AATTATTTAGCATGGTATCAGCAGAAACAGGGAAAATCTCCTCAACTCCT

GGTCTATACTGCAAAAACCTTAGCAGATGGTGTGCCATCAAGGTTCAGTG

GCAGTGGATCAGGAACACAATATTCTCTCAAGATCAATAGCCTGCAGCCT

GAAGATTTTGGGACTTATTACTGTCAACATTTTTGGAGTAATCCGTGGAC

GTTCGGTGGAGGCACCAAGCTGGAAATCAAACGGGCTGATGCTGCACCAA

CTGTATCCATCTTCCCACCATCCAGTGAGCAGTTAACATCTGGAGGTGCC

TCAGTCGTGTGCTTCTTGAACAACTTCTACCCCAAAGACATCAATGTCAA

GTGGAAGATTGATGGCAGTGAACGACAAAATGGCGTCCTGAACAGTTGGA

CTGATCAGGACAGCAAAGACAGCACCTACAGCATGAGCAGCACCCTCACG

TTGACCAAGGACGAGTATGAACGACATAACAGCTATACCTGTGAGGCCAC

TCACAAGACATCAACTTCACCCATTGTCAAGAGCTTCAACAGGAATGAGT

GTTAG

Individual regions of mouse light chain encoded sequence are highlighted with alternating bolded/unbolded text. Positions: 1-60=leader sequence; 61-129=framework region (LFR1); 130-162=complementarity determining region (LCDR1); 163-207=LFR2; 208-228=LCDR2; 229-324=LFR3; 325-351=LCDR3; 352-381 LFR4; 382-702=constant regions (CK); 703-705=stop codon.

The heavy and light chain AM-4 MIL-38 consensus DNA sequences above translate to the following heavy chain and light chain amino acid sequences:

AM-4 MIL-38 Mouse IgG1 Heavy Chain Amino Acid Consensus Sequence
(SEQ ID NO: 3)
MAWVWTLLFLMAAAQSIQAQIQLVQSGPELKKPGETVKISCKASGYAFTD

YSMNWVKQAPGKGLRWMGWINTETGEPTYTDDFKGRFAFSLETSASTAFL

QINNLRNEDTATYFCARHYDYGGFPYWGQGTLVTVSAAKTTPPSVYPLAP

GSAAQTNSMVTLGCLVKGYFPEPVTVTWNSGSLSSGVHTFPAVLQSDLYT

LSSSVTVPSSTWPSETVTCNVAHPASSTKVDKKI*VPRDCGCKPCICT*VPE

VSSVFIFPPKPKDVLTITLTPKVTCVVVDISKDDPEVQFSWFVDDVEVHT

AQTQPREEQFNSTFRSVSELPIMHQDWLNGKEFKCRVNSAAFPAPIEKTI

SKTKGRPKAPQVYTIPPPKEQMAKDKVSLTCMITDFFPEDITVEWQWNGQ

PAENYKNTQPIMDTDGSYFVYSKLNVQKSNWEAGNTFTCSVLHEGLHNHH

TEKSLSHSPGK*

Individual regions of mouse IgG1 heavy chain sequence are indicated in the amino acid sequence above. Positions 1-19=leader sequence; 20-49=framework region (HFR1); 50-54=complementarily determining region 1 (HCD1); 55-68=HFR2; 69-85=HCDR2; 86-117=HFR3; 118-126=HCDR3; 127-137=HFR4 (also called the joining region or J-region); 138-461=IgG1 chain constant regions (CH1-CH3) & stop codon (*). Hinge region—is italicized in the sequence above.

AM-4 consensus MIL-38 Light Chain Amino Acid Consensus Sequence
(SEQ ID NO: 4)
MSVLTQVLALLLLWLTGARCDIQMTQSPASLSASVGETVTITCRASGNVH

NYLAWYQQKQGKSPQLLVYTAKTLADGVPSRFSGSGSGTQYSLKINSLQP

EDEGTYYCQHFWSNPWTEGGGTKLEIKRADAAPTVSTEETSSEQLTSGGA

SVVCFLNNFYPKDINVKWKIDGSERQNGVLNSWTDQDSKDSTYSMSSTLT

LTKDEYERHNSYTCEATHKTSTSPIVKSFNRNEC*

Individual regions of light chain amino acid sequence are indicated as labelled: Positions 1-20=Leader sequence;

21-43=framework region (LFR1); 44-54=complementarily determining region 1 (LCDR1); 55-69=LFR2; 70-76=LCDR2; 77-108=LFR3; 109-117=LCDR3; 118-127=LFR4; 128-234=kappa constant region (CK) & stop codon(*)

Comparison of the consensus sequence between sequencing runs 224945 (1-O) and 449295-1 (Alfio I) showed that the sequences for the light chain and the heavy chain were identical (see sequence alignments below). As these sequences are consistent between the bi-clonal population (1-O) and the AM-4-like Alfio I population, they are termed "AM-4 consensus sequences" as above.

1. Light Chain Alignment: Biclonal vs AM-4 (Alfio I) vs AM-3 (Alfio II) alignment
Light chain alignment results of 224945 and 449295.apr

```
                                              Section 1

1       10        20        30        40        50        60        74
(SEQ ID NO: 4)  224945-1: Original 1-O Light Chain   (1)  ---MSVLTQVLALLLLWLTGARCDIQMTQSPASLSASVGETVTITCRASGNVHNYLAWYQQKGKSPQLLVYT
(SEQ ID NO: 4)  449295-1: Alfio I Light Chain        (1)  ---MSVLTQVLALLLLWLTGARCDIQMTQSPASLSASVGETVTITCRASGNVHNYLAWYQQKGKSPQLLVYT
(SEQ ID NO: 6)  449295-5: Alfio II Light Chain       (1)  MGIKMESQTQVFVFMLLWLSGVDGDIVMTQSQKFMSTSIGDRVSVTCKASQNVGSHVAWFQQKPGQSPKALIYS Section 2

75      80        90       100       110       120       130       148
(SEQ ID NO: 4)  224945-1: Original 1-O Light Chain  (75)  AKTLADGVPSRFSGSGSGTQYSLKINSLQPEDFGTYYCQHFWSNPWTFGGGTKLEIKRADAAPTVSIFPPSSEQ
(SEQ ID NO: 4)  449295-1: Alfio I Light Chain       (71)  AKTLADGVPSRFSGSGSGTQYSLKINSLQPEDFGTYYCQHFWSNPWTFGGGTKLEIKRADAAPTVSIFPPSSEQ
(SEQ ID NO: 6)  449295-5: Alfio II Light Chain      (75)  ASYRYSGVTDRFTGSGSGTFFTLTINNVQSEDLAEYFCQQYNSFPFTFGSGTKLEIKRADAAPTVSIFPPSSEQ Section 3

149      160       170       180       190       200       210       222
(SEQ ID NO: 4)  224945-1: Original 1-O Light Chain (149)  LTSGGASVVCFLNNFYPKDINVKWKIDGSERQNGVLNSWTDQDSKDSTYSMSSTLTLTKDEYERHNSYTCEATH
(SEQ ID NO: 4)  449295-1: Alfio I Light Chain      (145)  LTSGGASVVCFLNNFYPKDINVKWKIDGSERQNGVLNSWTDQDSKDSTYSMSSTLTLTKDEYERHNSYTCEATH
(SEQ ID NO: 6)  449295-5: Alfio II Light Chain     (149)  LTSGGASVVCFLNNEYPKDINVKWKIDGSERQNGVLNSWTDQDSKDSTYSMSSTLTLTKDEYERHNSYTCEATH Section 4

223      238
(SEQ ID NO: 4)  224945-1: Original 1-O Light Chain (223)  KTSTSPIVKSFNRNEC
(SEQ ID NO: 4)  449295-1: Alfio I Light Chain      (219)  KTSTSPIVKSFNRNEC
(SEQ ID NO: 6)  449295-5: Alfio II Light Chain     (223)  KTSTSPIVKSFNRNEC
```

2. Heavy Chain Alignment: Biclonal vs AM-4 (Alfio 1). Translated sequence of AM-3 (Alfio 2,) could not be determined.
Heavy chain alignment results of 224945 and 449295.apr

```
                                              Section 1

1       10        20        30        40        50        60        74
(SEQ ID NO: 3)  224945-1: Original 1-O Heavy Chain   (1)  MAWVWTLLFLMAAAQSIQAQIQLVQSGPELKKPGETVKISCKASGYAFTDYSMNWVKQAPGKGLRWMGWINTET
(SEQ ID NO: 3)  449295-1: Alfio I Heavy Chain        (1)  MAWVWTLLFLMAAAQSIQAQIQLVQSGPELKKPGETVKISCKASGYAFTDYSMNWVKQAPGKGLRWMGWINTET
```

-continued

Section 2

```
                      75          80         90        100       110        120       130         148
(SEQ ID NO: 3) 224945-1: Original 1-O Heavy Chain  (75) GEPTYTDDFKGRFAFSLETSASTAFLQINNLRNEDTATYFCARHYDYGGFPYWGQGTLVTVSAAKTTPPSVYPL
(SEQ ID NO: 3) 449295-1: Alfio I Heavy Chain       (75) GEPTYTDDFKGRFAFSLETSASTAFLQINNLRNEDTATYFCARHYDYGGFPYWGQGTLVTVSAAKTTPPSVYPL
```

Section 3

```
                      149         160       170       180       190       200       210         222
(SEQ ID NO: 3) 224945-1: Original 1-O Heavy Chain  (149) APGSAAQTNSMVTLGCLVKGYFPEPVTVTWNSGSLSSGVHTFPAVLQSDLYTLSSSVTVPSSTWPSETVTCNVA
(SEQ ID NO: 3) 449295-1: Alfio I Heavy Chain       (149) APGSAAQTNSMVTLGCLVKGYFPEPVTVTWNSGSLSSGVHTFPAVLQSDLYTLSSSVTVPSSTWPSETVTCNVA
```

Section 4

```
                      223        230       240       250       260       270        280          296
(SEQ ID NO: 3) 224945-1: Original 1-O Heavy Chain  (223) HPASSTKVDKKIVPRDCGCKPCICTVPEVSSVFIFPPKPKDVLTITLTPKVTCVVVDISKDDPEVQFSWFVDDV
(SEQ ID NO: 3) 449295-1: Alfio I Heavy Chain       (223) HPASSTKVDKKIVPRDCGCKPCICTVPEVSSVFIFPPKPKDVLTITLTPKVTCVVVDISKDDPEVQFSWFVDDV
```

Section 5

```
                      297        310       320        330       340        350       360         370
(SEQ ID NO: 3) 224945-1: Original 1-O Heavy Chain  (297) EVHTAQTQPREEQFNSTFRSVSELPIMHQDWLNGKEFKCRVNSAAFPAPIEKTISKTKGRPKAPQVYTIPPPKE
(SEQ ID NO: 3) 449295-1: Alfio I Heavy Chain       (297) EVHTAQTQPREEQFNSTFRSVSELPIMHQDWLNGKEFKCRVNSAAFPAPIEKTISKTKGRPKAPQVYTIPPPKE
```

Section 6

```
                      371        380       390       400       410       420       430          444
(SEQ ID NO: 3) 224945-1: Original 1-O Heavy Chain  (371) QMAKDKVSLTCMITDFFPEDITVEWQWNGQPAENYKNTQPIMDTDGSYFVYSKLNVQKSNWEAGNTFTCSVLHE
(SEQ ID NO: 3) 449295-1: Alfio I Heavy Chain       (371) QMAKDKVSLTCMITDFFPEDITVEWQWNGQPAENYKNTQPIMDTDGSYFVYSKLNVQKSNWEAGNTFTCSVLHE
```

Section 7

```
                      445   450          461
(SEQ ID NO: 3) 224945-1: Original 1-O Heavy Chain  (445) GLHNHHTEKSLSHSPGK
(SEQ ID NO: 3) 449295-1: Alfio I Heavy Chain       (445) GLHNHHTEKSLSHSPGK
```

AM-3 Consensus Sequences

No consistent heavy chain sequence could be obtained from the AM-3-like Alfio II cells. The light chain sequence obtained from sequencing run 449295-5 (Alfio II) was consistently obtained and showed clear differences in both the framework regions and the complementarity-determining regions compared to the sequence for the other two sequencing runs as shown in the alignment above (see "1. Light chain alignment" above).

AM-3 MIL-38 Kappa Light Chain DNA Consensus Sequence
(SEQ ID NO: 5)
ATGGGCATCAAGATGGAGTCACAGACTCAGGTCTTTGTATACATGTTGCT

GTGGTTGTCTGGTGTTGATGGAGACATTGTGATGACCCAGTCTCAAAAGT

TCATGTCCACATCAATAGGAGACAGGGTCAGCGTCACCTGCAAGGCCAGT

CAGAATGTGGGTTCTCATGTAGCCTGGTTTCAGCAGAAACCAGGGCAATC

TCCTAAAGCACTGATTTACTCGGCATCCTACCGGTACAGCGGAGTCACTG

ATCGCTTCACAGGCAGTGGATCTGGGACAGATTTCACTCTCACCATCAAC

AATGTGCAGTCTGAAGACTTGGCAGAGTATTTCTGTCAGCAATATAACAG

TTTTCCATTCACGTTCGGTTCGGGGACAAAGTTGGAAATAAAACGGGCTG

ATGCTGCACCAACTGTATCCATCTTCCCACCATCCAGTGAGCAGTTAACA

TCTGGAGGTGCCTCAGTCGTGTGCTTCTTGAACAACTTCTACCCCAAAGA

CATCAATGTCAAGTGGAAGATTGATGGCAGTGAACGACAAAATGGCGTCC

TGAACAGTTGGACTGATCAGGACAGCAAAGACAGCACCTACAGCATGAGC

AGCACCCTCACGTTGACCAAGGACGAGTATGAACGACATAACAGCTATAC

CTGTGAGGCCACTCACAAGACATCAACTTCACCCATTGTCAAGAGCTTCA

ACAGGAATGAGTGTTAG

* Individual regions of light chain encoded sequence are highlighted with alternating bolded/unbolded text. Positions: 1-72=leader sequence; 73-141=framework region (LFR1); 142-174=complementarity determining region (LCDR1); 175-219=LFR2; 220-240=LCDR2; 241-336=LFR3; 337-363=LCDR3; 364-393=LFR4; 394-714=constant region (CK); 715-717=stop codon AM-3 MIL-38 Light Chain Amino Acid Consensus Sequence
(SEQ ID NO: 6)
MGIKMESQTQVFVYMLLWLSGVDGDIVMTQSQKFMSTSIGDRVSVTCKAS

AQNVGSHVAWFQQKPGQSPKALIYSSYRYSGVTDRFTGSGSGTDFTLTIN

NVQSEDLAEYFCQQYNSFPFTFGSGTKLEIKRADAAPTVSIFPPSSEQLT

SGGASVVCFLNNFYPKDINVKWKIDGSERQNGVLNSWTDQDSKDSTYSMS

STLTLTKDEYERHNSYTCEATHKTSTSPIVKSFNRNEC*

Individual regions of light chain amino acid sequence are indicated as labelled: Positions 1-24=Leader sequence; 25-47=framework region (LFR1); 48-58=complementarity determining region 1 (LCDR1); 59-73=LFR2; 74-80=LCDR2; 81-112=LFR3; 113-121=LCDR3; 122-131=LFR4; 132-238=kappa constant region (CK) & stop codon(*)

Example 5: Preparation and Testing of Chimeric MIL-38 Antibodies 5.1 Materials and Methods
Preparation of Chimeric Antibodies Two optimised cDNA sequences were developed for cloning purposes. These were based on the AM-4 Heavy chain and Light chain consensus sequences identified above in Example 4.

The first optimised cDNA sequence was used in the generation of a mouse-human chimeric heavy chain sequence:

CHO codon Optimized cDNA Sequence #1 -
mouse-human chimeric heavy chain 1404 bp
(SEQ ID NO: 7)
ATGGCTTGGGTGTGGACACTGCTGTTCCTGATGGCTGCTGCCCAGAGTAT

TCAGGCTCAGATTCAGCTGGTCCAGAGCGGTCCCGAGCTGAAGAAGCCAG

GCGAGACCGTGAAGATCTCCTGCAAGGCCAGCGGCTACGCTTTCACAGAC

TATTCTATGAACTGGGTGAAGCAGGCCCCAGGCAAGGGCCTGAGGTGGAT

GGGCTGGATCAATACCGAGACAGGCGAGCCCACCTACACAGACGATTTCA

AGGGCCGGTTCGCTTTTTCCCTGGAGACCTCTGCCTCCACAGCTTTTCTG

CAGATCAACAATCTGAGAAACGAGGACACCGCCACATACTTCTGCGCTAG

GCACTACGATTATGGCGGCTTTCCTTATTGGGGCCAGGGCACCCTGGTGA

CAGTGTCCAGCGCCTCTACCAAGGGCCCATCCGTGTTTCCACTGGCTCCC

TCTTCCAAGAGCACCTCTGGCGGCACAGCCGCTCTGGGCTGTCTGGTGAA

GGATTACTTCCCAGAGCCCGTGACAGTGTCTTGGAACTCCGGCGCCCTGA

CCTCCGGAGTGCATACATTTCCCGCTGTGCTGCAGAGCTCTGGCCTGTAC

AGCCTGTCCAGCGTGGTGACCGTGCCTTCTTCCAGCCTGGGCACCCAGAC

ATATATCTGCAACGTGAATCACAAGCCATCCAATACAAAGGTGGACAAGA

AGGTG*GAGCCCAAGAGCTGTGATAAGACCCATACATGCCCCCCTTGTCCT*

GCTCCAGAGCTGCTGGGAGGACCTAGCGTGTTCCTGTTTCCACCCAAGCC

TAAGGACACCCTGATGATCTCTAGGACCCCCGAGGTGACATGCGTGGTGG

TGGACGTGTCCCACGAGGATCCTGAGGTGAAGTTCAACTGGTACGTGGAT

GGCGTGGAGGTGCATAATGCTAAGACCAAGCCTAGGGAGGAGCAGTACAA

CAGCACCTATCGGGTGGTGTCTGTGCTGACAGTGCTGCACCAGGACTGGC

TGAACGGCAAGGAGTATAAGTGCAAGGTGAGCAATAAGGCCCTGCCCGCT

CCTATCGAGAAGACCATCTCTAAGGCCAAGGGCCAGCCTCGGGAGCCACA

GGTGTACACACTGCCTCCAAGCAGAGACGAGCTGACCAPGAACCAGGTGT

CTCTGACATGTCTGGTGAAGGGCTTCTATCCTTCTGATATCGCTGTGGAG

TGGGAGTCCAATGGCCAGCCAGAGAACAATTACAAGACCACACCCCCTGT

GCTGGACAGCGATGGCTCTTTCTTTCTGTATTCCAAGCTGACCGTGGATA

AGAGCAGGTGGCAGCAGGGCAACGTGTTCTCCTGTAGCGTGATGCACGAG

GCACTGCACAACCACTACACTCAGAAATCCCTGTCCCTGTCACCTGGCAA

ATGA

Individual regions of mouse-human chimeric heavy chain encoded sequence are highlighted with alternating bolded/unbolded text. Positions: 1-57=leader sequence; 58-147=framework region (FR1); 148-162=complementarity determining region (CDR1); 163-204=FR2; 205-255=CDR2; 256-351=FR3; 352-378=CDR3; 379-411=FR4; 412-1401=human constant regions (CH1-CH3); 706-750=hinge region (italicized); 1402-1405=stop codon.

The second optimised cDNA sequence generated was used in the generation of a mouse-human chimeric light chain sequence:

```
CHO Codon Optimized cDNA Sequence #2 -
mouse-human chimeric light chain 705 bp
                                        (SEQ ID NO: 8)
ATGAGCGTGCTGACCCAGGTGCTGGCCCTGCTGCTGCTGTGGCTGACCGG

AGCCCGTTGCGACATCCAGATGACCCAGTCCCCTGCCTCTCTGTCCGCCA

GCGTGGGCGAGACCGTGACAATCACCTGCAGAGCCTCTGGCAACGTGCAC

AATTACCTGGCTTGGTATCAGCAGAAGCAGGGCAAGTCCCCACAGCTGCT

GGTGTACACAGCCAAGACCCTGGCTGACGGCGTGCCCAGCAGGTTCTCTG

GCTCCGGCAGCGGCACACAGTATAGCCTGAAGATCAACTCTCTGCAGCCT

GAGGATTTTGGCACCTACTATTGCCAGCATTTCTGGTCTAATCCATGGAC

ATTTGGCGGCGGCACCAAGCTGGAGATCAAGAGGACAGTGGCCGCTCCCT

CCGTGTTCATCTTTCCCCCTAGCGACGAGCAGCTGAAGTCTGGCACCGCT

TCCGTGGTGTGCCTGCTGAACAATTTCTACCCTCGGGAGGCCAAGGTGCA

GTGGAAGGTGGATAACGCTCTGCAGTCTGGCAATTCCCAGGAGAGCGTGA

CAGAGCAGGACTCTAAGGATTCCACCTATAGCCTGTCCAGCACACTGACC

CTGTCCAAGGCCGACTACGAGAAGCACAAGGTGTATGCTTGTGAGGTCAC

TCACCAGGGGCTGTCAAGTCCAGTCACAAAGTCCTTCAATAGGGGGGAAT

GCTGA
```

Individual regions of mouse-human chimeric light chain encoded sequence are highlighted with alternating bolded/unbolded text. Positions: 1-60=leader sequence; 61-129=framework region (LFR1); 130-162=complementarily determining region (LCDR1); 163-207=LFR2; 208-228=LCDR2; 229-324=LFR3; 325-351=LCDR3; 352-381=LFR4; 382-702=human constant region (CK); 703-705=stop codon.

Chimeric MIL-38 Mouse Human CH1-CH3 Chain were transiently expressed in suspension CHO-3E7 cells using serum free medium, followed by one-step purification.

CHO-3E7 cells were grown in serum free FreeStyle™ CHO Expression Medium (Life Technologies, Carlsbad, Calif., USA). The cells were maintained in Erlenmeyer Flasks (Corning Inc., Acton, Mass.) at 37° C. with 5% $CO_2$ on an orbital shaker (VWR Scientific, Chester, Pa.). On the day of transfection, DNA and PEI (Polysciences, Eppelheim, Germany) were mixed at an optimal ratio and then added into the flask with cells ready for transfection. The supernatant collected on day 6 was used for further purification.

Cell culture broth was centrifuged and followed by filtration. Filtered supernatant was loaded onto a 5 ml Protein A CIP column (GenScript, Cat.No.L00433) at 3.0 ml/min. After washing and elution with appropriate buffer, the fractions were collected and neutralized with 1M Tris-HCl, pH 9.0. The purified protein was analyzed by SDS-PAGE, Western blot by using standard protocols for molecular weight, yield and purity measurements.

Chimeric MIL-38 Antibody Assays (Slide Immunoflourescence)

The MIL-38 chimeric antibody was used in immunofluorescence assays with DU-145 cells. The murine MIL-38 prep 33A was used as a positive control for GPC-1 antigen staining, while Cetuximab (a chimeric antibody targeting the EGFR) was used as a positive control for staining of human IgG constant regions. A slide with no primary antibody was used as a negative control. Staining was performed essentially as described in Section 1.1 with the exceptions that secondary antibodies were labeled with Alexafluor 488 and that anti-human antibodies were used to stain the chimeric and cetuximab samples.

Chimeric MIL-38 Western Blots

Figure 9:
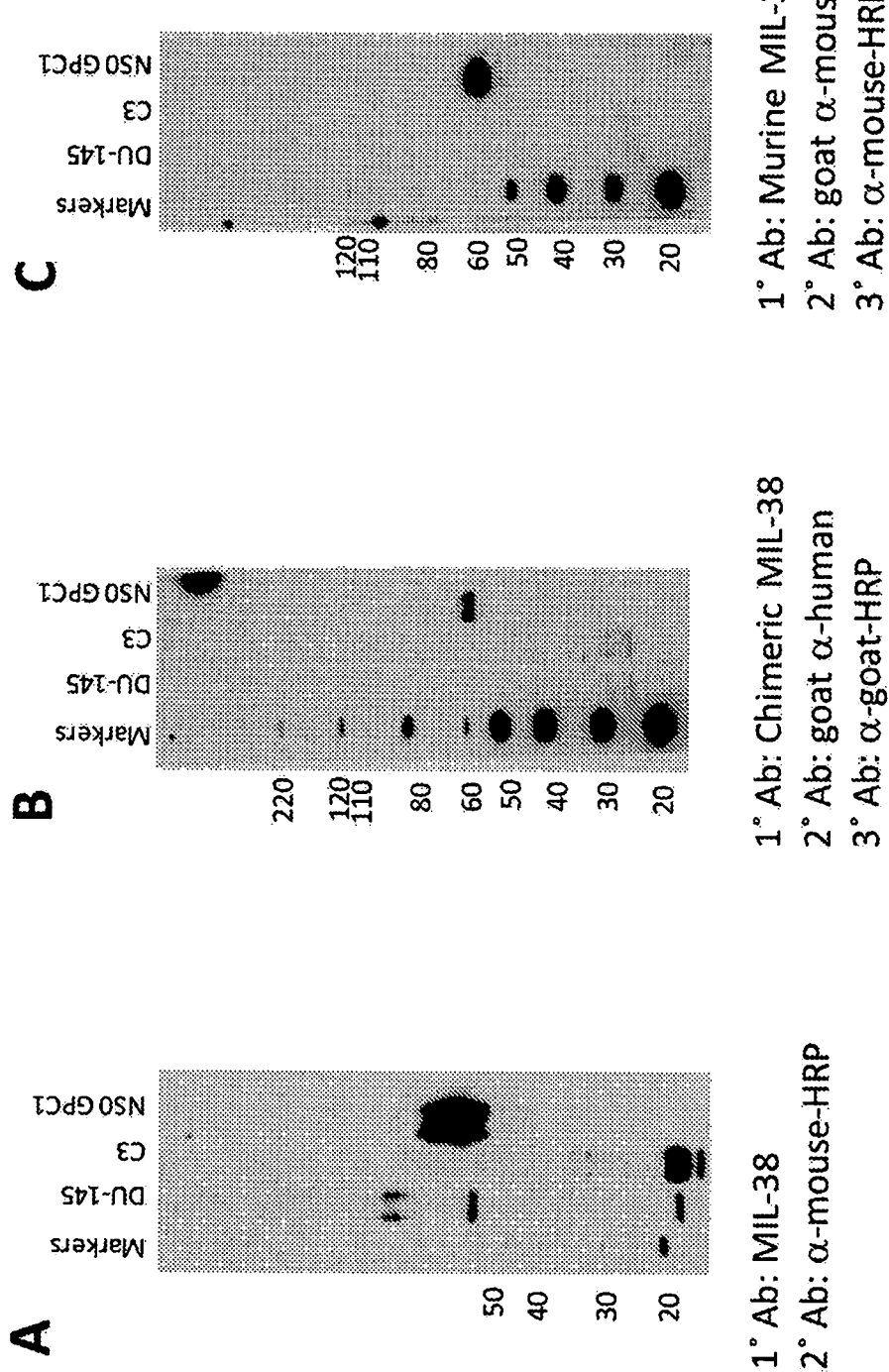
FIG. 9 shows western blot analysis of chimeric MIL-38 antibody.

The reactivity of the chimeric MIL-38 and murine MIL-38 towards DU-145 and C3 MPEK extracts as well as to recombinant NS0-produced GPC-1 antigen was tested by Western blot. Western blots were probed either by murine MIL-38 or chimeric MIL-38. Chimeric MIL-38 was detected by goat anti-human secondary antibody followed by a sheep-anti-goat HRP antibody. As a control, murine MIL-38 was detected by goat anti-mouse secondary antibody followed by a sheep-anti-goat HRP antibody. Equivalent reactivity was observed for chimeric MIL-38 and murine MIL-38 when detected under equivalent conditions. FIG. 9A shows a western blot probed with murine MIL-38, followed by anti-mouse HRP secondary antibody. FIG. 9B shows a western blot probed with chimeric MIL-38, followed by goat anti-human secondary antibody. The complex was detected using a sheep-anti-goat HRP antibody. FIG. 9C shows a western blot probed with murine MIL-38, followed by goat anti-human mouse antibody. The complex was detected using a sheep-anti-mouse HRP antibody.

5.2 Results

Expression of Chimeric Antibody Sequences

Figure 7:
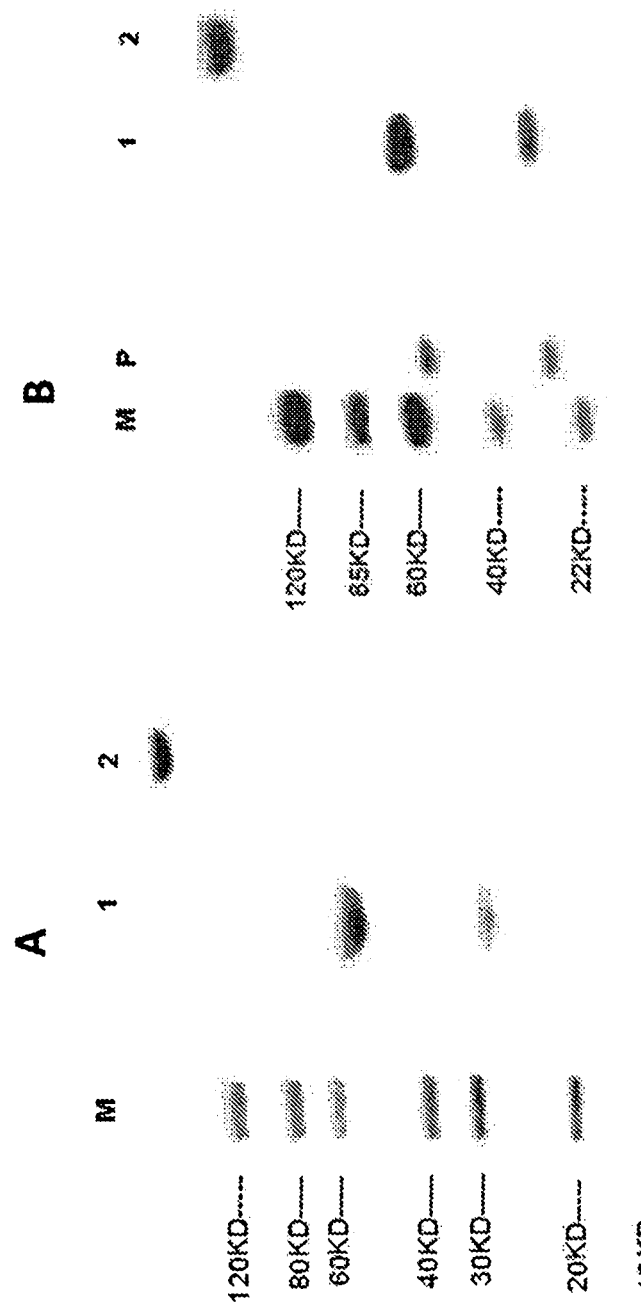
FIG. 7 shows SDS-PAGE (FIG. 7A) and Western blot (FIG. 7B) analyses of a chimeric MIL-38 antibody. Lane M=protein marker; Lane 1=reducing conditions; Lane 2=non-reducing conditions; Lane P=Human IgG1, Kappa (Sigma, Cat. No 15154) as positive control.
Figure 8:
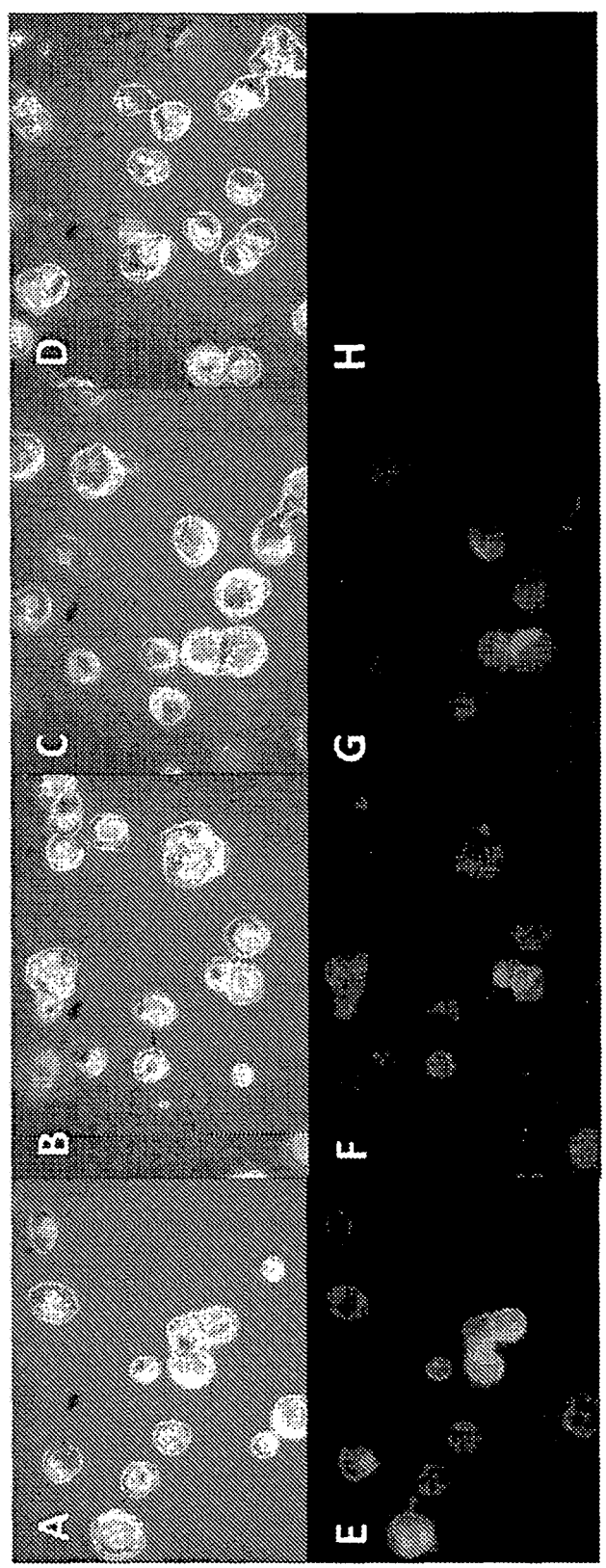
FIG. 8 shows images from immunofluorescence assays using chimeric MIL-38 antibody and controls on DU-145 cells.

The recombinant plasmids encoding heavy chain and light chain of Chimeric MIL-38 Mouse Human CH1-CH3 Chain were transiently transfected into suspension CHO-3E7 cell cultures. The target protein was captured from the cell culture supernatant by Protein A CIP 5 ml column and followed by buffer exchange. The purified protein was analyzed by SDS-PAGE and Western blot as shown in FIGS. 7A and 7B. 3 µg of sample was loaded on SDS-PAGE and 0.3 µg of total protein was loaded on Western blot. The primary antibody for Western blot was Goat Anti-Human IgG-HRP (GenScript, Cat.No.A00166).

Chimeric Antibody Sequences

Optimised cDNA sequence #1 (SEQ ID NO: 7) was used to generate a chimeric MIL-38 antibody heavy chain with the following amino acid sequence:

```
Chimeric MIL-38 Mouse Human CH1-CH3 Chain Sequence
Mouse VH-Human CH1-CH3 Chain (heavy chain)
                                        (SEQ ID NO: 9)
MAWVWTLLFLMAAAQSIQAQIQLVQSGPELKKPGETVKISCKASGYAFTD

YSMNWVKQAPGKGLRWMGWINTETGEPTYTDDFKGRFAFSLETSASTAFL

QINNLRNEDTATYFCARHYDYGGFPYWGQGTLVTVSSASTKGPSVFPLAP

SSKSTSGGTAALGCLVKDYFPEPVTVSWNSGALTSGVHTFPAVLQSSGLY

SLSSVVTVPSSSLGTQTYICNVNHKPSNTKVDKKVEPKSCDKTHTCPPC

PAPELLGGPSVFLFPPKPKDTLMISRTPEVTCVVVDVSHEDPEVKFNWYV
```

```
-continued
DGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMH

EALHNHYTQKSLSLSPGK*
```

Individual regions of mouse-human chimeric heavy chain sequence are indicated in the amino acid sequence above: Positions 1-19=leader sequence; 20-49=framework region (HFR1); 50-54=complementarity determining region 1 (HCD1); 55-68=HFR2; 69-85=HCDR2; 86-117=HFR3; 118-126=HCDR3; 127-137=HFR4 (also called the joining region or J-region); 138-467=IgG1 chain constant regions (CH1-CH3), & stop codon (*). Hinge sequence—human IgG1 heavy chain hinge sequence is italicized above.

Optimised cDNA sequence #2 (SEQ ID NO: 8) was used to generate a chimeric MIL-38 antibody light chain with the following amino acid sequence:

```
Chimeric MIL-38 Mouse-Human Kappa Light Chain
Sequence: Mouse VK-Human CK sequence
                                  (SEQ ID NO: 10)
MSVLTQVIALLLLWLTGARCDIQMTQSPASLSASVGETVTITCRASGNVH

NYLAWYQQKQGKSPQLLVYTAKTLADGVPSRFSGSGSGTQYSLKINSLQP

EDFGTYYCQHFWSNPWTFGGGTKLEIKRTVAAPSVFIFPPSDEQLKSGTA

SVVCLLNNFYPREAKVQWKVDNALQSGNSQESVTEQDSKDSTYSLSSTLT

LSKADYEKHKVYACEVTHQGLSSPVTKSFNRGEC*
```

Individual regions of mouse-human chimeric light chain amino acid sequence are indicated as labelled: Positions 1-20=Leader sequence; 21-43=framework region (LFR1); 44-54=complementarity determining region 1 (LCDR1); 55-69=LFR2; 70-76=LCDR2; 77-108=LFR3; 109-117=LCDR3; 118-127=LFR4; 128-234=kappa constant region (CK) & stop codon(*)

Chimeric MIL-38 Antibody Assays (Slide Immuno-flourescence)

FIGS. 8A-D show bright field images of cells. FIG. 8E shows staining of the 33A positive control. FIG. 8F shows staining of the chimeric MIL-38 antibody. FIG. 8G shows staining of using a commercial chimeric (mouse/human) monoclonal antibody (Cetuximab) positive control, and FIG. 8H shows the no primary antibody negative control staining. Strong staining was observed in FIGS. 8E, F and G and no staining was observed in FIG. 8H. These results demonstrate that the chimeric MIL-38 antibody successfully binds DU-145 cells in IFA, indicating that the binding specificity of the parental murine MIL-38 antibody has been maintained.

Chimeric MIL-38 Antibody Assays (Western Blots)

FIG. 9A shows a western blot probed with murine MIL-38, followed by anti-mouse HRP secondary antibody. Exposure time for the Western blot shown in FIG. 9A was 30 seconds. FIG. 9B shows a western blot probed with chimeric MIL-38, followed by goat anti-human secondary antibody. The complex was detected using a sheep-anti-goat HRP antibody. Exposure time for the Western blot shown in FIG. 9B was 30 minutes. FIG. 9C shows a western blot probed with murine MIL-38, followed by goat anti-mouse antibody. The complex was detected using a sheep-anti-goat HRP antibody. Exposure time for the Western blot shown in FIG. 9C was 30 minutes.

The murine MIL-38 anti-mouse recognises the antigen in DU-145 lysates and recombinant GPC-1 NS0. Reactivity was not observed in C3 lysates as expected (FIG. 9A).

A three-antibody detection method was required to test reactivity of the chimeric MIL-38 with DU-145 and C3 extracts as well as recombinant NS0 GPC-1 (FIG. 9B). A control western blot using a three antibody detection method was also performed with murine MIL-38 (FIG. 9C). When a three antibody detection method was used, detection was far less sensitive than using the standard two antibody method (for the Western blots shown in FIGS. 9A and C, exposure time used for FIG. 9A was 30 seconds, whereas that used for FIG. 9C was 30 minutes).

As shown in FIG. 9B, the Chimeric MIL-38 recognises the recombinant GPC-1 NS0 antigen and shows comparable reactivity to murine MIL-38 when detected using this method (compare FIGS. 9B and C).

5.3 Discussion

The Chimeric MIL-38 antibody was successfully expressed and purified in suspension CHO-3E7 cells. The H and L chains of target antibody were detected with estimated molecular weights of ~55 kDa (Cal.M.W. ~52 kDa) and 28 kDa (Cal.M.W. ~26 kDa) based on SDS-PAGE and Western blot analysis.

Equivalent reactivity between the chimeric MIL-38 and the murine parent was observed in IFA and western blotting, indicating that binding specificity has been maintained in the construction of the chimeric antibody.

The invention claimed is:

1. A composition comprising: first antibodies and/or antigen binding fragments thereof, wherein the first antibodies comprise:
   (a) a heavy chain variable region comprising:
      a complementarity determining region 1 (CDR1) comprising or consisting of an amino acid sequence defined by positions 50-54 of SEQ ID NO: 3;
      a complementarity determining region 2 (CDR2) comprising or consisting of an amino acid sequence defined by positions 69-85 of SEQ ID NO: 3; and
      a complementarity determining region 3 (CDR3) comprising or consisting of an amino acid sequence defined by positions 118-126 of SEQ ID NO: 3; and
   (b) a light chain variable region comprising:
      a complementarity determining region 1 (CDR1) comprising or consisting of an amino acid sequence defined by positions 44-54 of SEQ ID NO: 4;
      a complementarity determining region 2 (CDR2) comprising or consisting of an amino acid sequence defined by positions 70-76 of SEQ ID NO: 4; and
      a complementarity determining region 3 (CDR3) comprising or consisting of an amino acid sequence defined by positions 109-117 of SEQ ID NO: 4;
   and wherein the composition does not contain second antibodies comprising a light chain variable region comprising:
      a complementarity determining region 1 (CDR1) comprising or consisting of an amino acid sequence defined by positions 48-58 of SEQ ID NO: 6;
      a complementarity determining region 2 (CDR2) comprising or consisting of an amino acid sequence defined by positions 74-80 of SEQ ID NO: 6; and
      a complementarity determining region 3 (CDR3) comprising or consisting of an amino acid sequence defined by positions 113-121 of SEQ ID NO: 6.

2. The composition according to claim 1, wherein the first antibodies and/or antigen binding fragments thereof have binding specificity for an epitope present in glypican-1 heparan sulfate proteoglycan (GPC-1).

3. The composition according to claim 1, wherein the first antibodies and/or antigen binding fragments thereof are isotype IgG1.

4. The composition according 1, wherein the first antibodies and/or antigen binding fragments thereof are any one or more of monoclonal antibodies, humanised antibodies, chimeric antibodies, multimeric antibodies, and/or synthetic antibodies.

5. The composition according to claim 1, wherein the antigen binding fragments are any one or more of single chain variable fragments (scFv), variable domain (Fv) fragments, fragment antigen binding (Fab) fragments, F(ab)2 fragments, peptides, or proteolytic fragments containing an epitope binding region.

6. The composition according to claim 1, wherein the first antibodies and/or antigen binding fragments thereof further comprise:
   (a) one or more heavy chain variable region FR (framework regions) as defined by a sequence selected from any one or more of: residues 20-49 of SEQ ID NO: 3, residues 55-68 of SEQ ID NO: 3, residues 86-117 of SEQ ID NO: 3, and residues 127-137 of SEQ ID NO: 3; and/or
   (b) one or more light chain variable region FR (framework regions) as defined by a sequence selected from any one or more of: residues 21-43 of SEQ ID NO: 4, residues 55-69 of SEQ ID NO: 4, residues 77-108 of SEQ ID NO: 4, and residues 118-127 of SEQ ID NO: 4.

7. The composition according to claim 1, wherein the first antibodies and/or antigen binding fragments thereof further comprise any one or more of:
   (a) a heavy chain constant domain sequence as defined by positions 138-461 of SEQ ID NO: 3;
   (b) a light chain constant domain sequence as defined by positions 128-234 of SEQ ID NO: 4; and
   (c) a hinge region.

8. The composition according to claim 1, wherein the first antibodies comprise or consist of a heavy chain sequence as defined by positions 20-461 of SEQ ID NO: 3 and a light chain sequence as defined by positions 21-234 of SEQ ID NO: 4.

9. The hybridoma cells deposited at Cellbank Australia under accession number CBA20140026.

10. A cell culture composition, wherein:
   (a) the cell culture composition comprises the hybridoma cells according to claim 9; and
   (b) the cell culture composition does not comprise hybridoma cells that produce an antibody comprising:
      a light chain variable region that comprises any one or more of:
      a complementarity determining region 1 (CDR1) comprising or consisting of an amino acid sequence defined by positions 48-58 of SEQ ID NO: 6;
      a complementarity determining region 2 (CDR2) comprising or consisting of an amino acid sequence defined by positions 74-80 of SEQ ID NO: 6; and
      a complementarity determining region 3 (CDR3) comprising or consisting of an amino acid sequence defined by positions 113-121 of SEQ ID NO: 6.

11. The cell culture composition according to claim 10, wherein the cell culture composition does not comprise hybridoma cells that produce an antibody comprising one or more light chain variable region FR (framework regions) as defined by a sequence selected from any one or more of: residues 25-47 of SEQ ID NO: 6, residues 59-73 of SEQ ID NO: 6, residues 81-112 of SEQ ID NO: 6, or residues 122-131 of SEQ ID NO: 6.

12. The composition according to claim 4, wherein the first antibodies and/or antigen binding fragments thereof are chimeric.

13. The composition according to claim 12, wherein the first antibodies and/or antigen binding fragments thereof are chimeric antibodies comprising:
   (a) a heavy chain constant region comprising or consisting of an amino acid sequence as defined in residues 138-467 of SEQ ID NO: 9; and
   (b) a light chain constant region comprising or consisting of an amino acid sequence as defined in residues of 128-234 SEQ ID NO: 10.

* * * * *

UNITED STATES PATENT AND TRADEMARK OFFICE
CERTIFICATE OF CORRECTION

PATENT NO. : 10,577,418 B2
APPLICATION NO. : 15/520722
DATED : March 3, 2020
INVENTOR(S) : Douglas Campbell et al.

It is certified that error appears in the above-identified patent and that said Letters Patent is hereby corrected as shown below:

In the Claims

Column 67, Line 44, Claim 4, please delete "The composition according 1" and insert -- The composition according to claim 1 -- therefor.

Signed and Sealed this
Sixteenth Day of June, 2020

Andrei Iancu
*Director of the United States Patent and Trademark Office*